US012637425B2

(12) United States Patent
Lopez et al.

(10) Patent No.: US 12,637,425 B2
(45) Date of Patent: May 26, 2026

(54) COMPOUNDS AND FORMULATIONS FOR TREATING OPHTHALMIC DISEASES

(71) Applicant: Visus Therapeutics, Inc., Seattle, WA (US)

(72) Inventors: Michael S. Lopez, South San Francisco, CA (US); Bryan M. Dunyak, South San Francisco, CA (US)

(73) Assignee: VISUS THERAPEUTICS, INC., Seattle, WA (US)

( * ) Notice: Subject to any disclaimer, the term of this patent is extended or adjusted under 35 U.S.C. 154(b) by 435 days.

(21) Appl. No.: 18/043,146

(22) PCT Filed: Aug. 30, 2021

(86) PCT No.: PCT/US2021/048250

§ 371 (c)(1),
(2) Date: Feb. 27, 2023

(87) PCT Pub. No.: WO2022/047315

PCT Pub. Date: Mar. 3, 2022

(65) Prior Publication Data

US 2023/0322672 A1 Oct. 12, 2023

Related U.S. Application Data

(60) Provisional application No. 63/072,724, filed on Aug. 31, 2020.

(51) Int. Cl.

| | |
|---|---|
| *C07D 209/14* | (2006.01) |
| *A61P 27/10* | (2006.01) |
| *C07D 401/12* | (2006.01) |
| *C07D 401/14* | (2006.01) |
| *C07D 403/12* | (2006.01) |
| *C07D 403/14* | (2006.01) |
| *C07D 405/14* | (2006.01) |
| *C07D 417/12* | (2006.01) |
| *C07D 417/14* | (2006.01) |
| *C07D 471/04* | (2006.01) |
| *C07D 491/048* | (2006.01) |

(52) U.S. Cl.

CPC ............ *C07D 209/14* (2013.01); *A61P 27/10* (2018.01); *C07D 401/12* (2013.01); *C07D 401/14* (2013.01); *C07D 403/12* (2013.01); *C07D 403/14* (2013.01); *C07D 405/14* (2013.01); *C07D 417/12* (2013.01); *C07D 417/14* (2013.01); *C07D 471/04* (2013.01); *C07D 491/048* (2013.01)

(58) Field of Classification Search

None

See application file for complete search history.

(56) References Cited

U.S. PATENT DOCUMENTS

| | | | | |
|---|---|---|---|---|
| 6,403,590 B1 * | 6/2002 | Hellberg | ................. A61P 27/06 514/913 |
| 2010/0146881 A1 | 6/2010 | Framer et al. | |
| 2012/0035159 A1 | 2/2012 | Hidaka et al. | |
| 2013/0274269 A1 | 10/2013 | Hidaka et al. | |

FOREIGN PATENT DOCUMENTS

| | | | | |
|---|---|---|---|---|
| EP | 3482797 A1 | | 5/2019 | |
| JP | 2006504681 A | | 2/2006 | |
| JP | 2015529646 A | | 10/2015 | |
| JP | 2015535239 A | | 12/2015 | |
| WO | WO-2010146881 A1 | * | 12/2010 | ................ A61P 9/00 |
| WO | WO-2012086727 A1 | * | 6/2012 | ................ A61P 9/12 |
| WO | WO-2016071293 A2 | | 5/2016 | |
| WO | WO-2019080882 A1 | * | 5/2019 | ........... C07D 333/70 |

OTHER PUBLICATIONS

File Registry on STN, RN 1011678-08-2, Entered STN: Apr. 2, 2008.
File Registry on STN, RN 1011678-28-6, Entered STN: Apr. 2, 2008.
File Registry on STN, RN 1011678-43-5, Entered STN: Apr. 2, 2008.
File Registry on STN, RN 1011858-20-0, Entered STN: Apr. 3, 2008.
File Registry on STN, RN 1011858-32-4, Entered STN: Apr. 3, 2008.
File Registry on STN, RN 1011858-43-7, Entered STN: Apr. 3, 2008.
File Registry on STN, RN 1011863-17-4, Entered STN: Apr. 3, 2008.
File Registry on STN, RN 1011863-33-4, Entered STN: Apr. 3, 2008.
File Registry on STN, RN 1011863-45-8, Entered STN: Apr. 3, 2008.
File Registry on STN, RN 1011936-81-4, Entered STN: Apr. 3, 2008.
File Registry on STN, RN 1011936-93-8, Entered STN: Apr. 3, 2008.
File Registry on STN, RN 1091392-98-1, Entered STN: Dec. 29, 2008.
File Registry on STN, RN 1091416-54-4, Entered STN: Dec. 29, 2008.
File Registry on STN, RN 1091438-91-3, Entered STN: Dec. 29, 2008.
File Registry on STN, RN 1091440-84-4, Entered STN: Dec. 29, 2008.
File Registry on STN, RN 1091471-97-4, Entered STN: Dec. 29, 2008.
File Registry on STN, RN 1208417-82-6, Entered STN: Mar. 10, 2010.

(Continued)

*Primary Examiner* — Clinton A Brooks
*Assistant Examiner* — Nicola Maria Bauer
(74) *Attorney, Agent, or Firm* — Sterne, Kessler, Goldstein & Fox PLLC

(57) ABSTRACT

The present disclosure is directed to compounds, compositions, formulations and methods of use thereof in the treatment and prevention of ocular conditions including cataract and presbyopia.

20 Claims, No Drawings

(56) References Cited

OTHER PUBLICATIONS

File Registry on STN, RN 1208952-27-5, Entered STN: Mar. 11, 2010.
File Registry on STN, RN 1209706-50-2, Entered STN: Mar. 14, 2010.
File Registry on STN, RN 1209942-10-8, Entered STN: Mar. 15, 2010.
File Registry on STN, RN 1210019-51-4, Entered STN: Mar. 15, 2010.
File Registry on STN, RN 1210217-24-5, Entered STN: Mar. 16, 2010.
File Registry on STN, RN 1210378-60-1, Entered STN: Mar. 16, 2010.
File Registry on STN, RN 1210420-09-9, Entered STN: Mar. 16, 2010.
File Registry on STN, RN 1210877-13-6, Entered STN: Mar. 17, 2010.
File Registry on STN, RN 1210978-67-8, Entered STN: Mar. 17, 2010.
File Registry on STN, RN 1211284-73-9, Entered STN: Mar. 18, 2010.
File Registry on STN, RN 1211309-26-0, Entered STN: Mar. 18, 2010.
File Registry on STN, RN 1211322-61-0, Entered STN: Mar. 18, 2010.
File Registry on STN, RN 1211345-59-3, Entered STN: Mar. 18, 2010.
File Registry on STN, RN 1211396-04-1, Entered STN: Mar. 18, 2010.
File Registry on STN, RN 1211751-80-2, Entered STN: Mar. 19, 2010.
File Registry on STN, RN 1211775-02-8, Entered STN: Mar. 19, 2010.
File Registry on STN, RN 1211854-65-7, Entered STN: Mar. 19, 2010.
File Registry on STN, RN 1705501-63-8, Entered STN: May 15, 2015.
File Registry on STN, RN 2034300-49-5, Entered STN: Nov. 18, 2016.
File Registry on STN, RN 2034311-43-6, Entered STN: Nov. 18, 2016.
File Registry on STN, RN 2034465-33-1, Entered STN: Nov. 18, 2016.
File Registry on STN, RN 2034466-81-2, Entered STN: Nov. 18, 2016.
File Registry on STN, RN 2034570-03-9, Entered STN: Nov. 18, 2016.
File Registry on STN, RN 2331089-84-8, Entered STN: Jun. 12, 2019.
File Registry on STN, RN 2332279-84-0, Entered STN: Jun. 13, 2019.
File Registry on STN, RN 2332778-49-9, Entered STN: Jun. 13, 2019.
File Registry on STN, RN 2334347-40-7, Entered STN: Jun. 14, 2019.
File Registry on STN, RN 2336297-17-5, Entered STN: Jun. 17, 2019.
File Registry on STN, RN 2336299-17-1, Entered STN: Jun. 17, 2019.
File Registry on STN, RN 2338143-18-1, Entered STN: Jun. 18, 2019.
File Registry on STN, RN 2339112-83-1, Entered STN: Jun. 19, 2019.
File Registry on STN, RN 2339220-84-5, Entered STN: Jun. 19, 2019.
File Registry on STN, RN 2339221-04-2, Entered STN: Jun. 19, 2019.
File Registry on STN, RN 2339221-92-8, Entered STN: Jun. 19, 2019.
File Registry on STN, RN 2339445-19-9, Entered STN: Jun. 19, 2019.
File Registry on STN, RN 2339704-11-7, Entered STN: Jun. 19, 2019.
File Registry on STN, RN 2341558-16-3, Entered STN: Jun. 20, 2019.
File Registry on STN, RN 2343928-26-5, Entered STN: Jun. 23, 2019.
File Registry on STN, RN 2343928-35-6, Entered STN: Jun. 23, 2019.
File Registry on STN, RN 2344608-85-9, Entered STN: Jun. 24, 2019.
File Registry on STN, RN 2346521-23-9, Entered STN: Jun. 26, 2019.
File Registry on STN, RN 946347-36-0, Entered STN: Sep. 7, 2007.
File Registry on STN, RN 946347-84-8, Entered STN: Sep. 7, 2007.
File Registry on STN, RN 953911-92-7, Entered STN: Nov. 15, 2007.
File Registry on STN, RN 953964-41-5, Entered STN: Nov. 15, 2007.
File Registry on STN, RN 953965-37-2, Entered STN: Nov. 15, 2007.
File Registry on STN, RN 954241-59-9, Entered STN: Nov. 16, 2007.
File Registry on STN, RN 958562-25-9, Entered STN: Dec. 18, 2007.
File Registry on STN, RN 958589-31-6, Entered STN: Dec. 18, 2007.
File Registry on STN, RN 958589-37-2, Entered STN: Dec. 18, 2007.
International Search Report and Written Opinion for International Application No. PCT/US2021/048250, Korean Intellectual Property Office, Republic of Korea, mailed on Dec. 20, 2021, 13 pages.
File Registry on STN, RN 1211827-80-3, Entered STN: Mar. 19, 2010.
File Registry on STN, RN 1211644-58-4, Entered STN: Mar. 19, 2010.

* cited by examiner

COMPOUNDS AND FORMULATIONS FOR TREATING OPHTHALMIC DISEASES

CROSS-REFERENCE TO RELATED APPLICATIONS

This application claims benefit of U.S. Provisional Patent Application No. 63/072,724, filed on Aug. 31, 2020, which is incorporated herein by reference in its entirety.

BACKGROUND OF THE INVENTION

Cataract affects more than 24 million Americans age 40 and older and by age 75, half of all Americans have cataract. Cataract is a clouding of the lens in the eye that affects vision. The conventional treatment for cataract is surgical replacement with an artificial intraocular lens. Surgical treatment of cataract, however, is costly and an artificial lens does not have the same overall optical qualities as a normal lens.

It is estimated that approximately 112 million Americans currently suffer from presbyopia. Presbyopia is age-related far-sightedness that commonly manifests begins between the ages of 40 and 50, initially causing blurred vision, difficulty seeing in dim light, and eye strain. In healthy eyes, the lens is able to focus light from objects at different distances by a process called accommodation—a slight change in lens shape by the surrounding muscles to change the way light passes through the interior of the lens and onto the retina where the image is formed. During accommodation, muscles surrounding the lens contract, causing the lens to change shape and increasing the focusing power of the eye. This allows focus and clear vision at near and far distances. With increasing age, the lens becomes stiffer as its structural crystallin proteins become misfolded. This increased lens stiffness limits the eye's ability to focus for reading or other tasks that require clear vision at near distances. Reading glasses or glasses with progressive lenses are the most common correction for presbyopia although surgical options are available as well.

As cataract and presbyopia affect billions of people worldwide, there exists a significant need for new methods for treating and preventing these diseases.

SUMMARY OF THE INVENTION

Provided herein are compounds of Formula (I), or a pharmaceutically acceptable salt thereof, and pharmaceutical compositions comprising said compounds. The subject compounds and compositions are useful for the treatment of ophthalmic disease, such as cataract and presbyopia.

Provided herein is a compound, and pharmaceutical compositions comprising said compound, represented by Formula (I):

Formula (I)

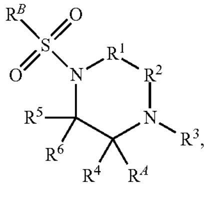

or a pharmaceutically acceptable salt thereof, wherein:

$R^A$ is an optionally substituted bicyclic heteroaryl, wherein substituents on $R^A$ are independently selected from $R^a$;

each $R^a$ is independently selected from:

halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$NR^{12}SO_2R^{12}$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_{10}$ carbocycle and 3- to 10-membered heterocycle, each of which is optionally substituted with one or more substituents independently selected from $R^9$;

$R^B$ is an optionally substituted bicyclic heteroaryl, wherein substituents on $R^B$ are independently selected from $R^b$;

each $R^b$ is independently selected from:

halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$SR^{12}$, —$S(=O)R^{13}$, —$SO_2R^{13}$, —$SO_2N(R^{12})_2$, —$NR^{12}SO_2R^{13}$, —$NO_2$;

$C_1$-$C_6$ alkyl, $C_2$-$C_6$ alkenyl, and $C_2$-$C_6$ alkynyl; each of which is optionally substituted with one or more substituents independently selected from $R^9$; and $C_3$-$C_{10}$ carbocycle and 3- to 10-membered heterocycle, each of which is optionally substituted with one or more substituents independently selected from $R^9$;

$R^1$ is selected from hydrogen; and $C_1$-$C_6$ alkyl, $C_2$-$C_6$ alkenyl, $C_2$-$C_6$ alkynyl, each of which is optionally substituted with one or more substituents independently selected from $R^9$;

$R^2$ and $R^3$ are independently selected from hydrogen; and $C_1$-$C_6$ alkyl, $C_2$-$C_6$ alkenyl, $C_2$-$C_6$ alkynyl, $C_3$-$C_6$ carbocycle, and 3- to 6-membered heterocycle, each of which is optionally substituted with one or more substituents independently selected from $R^9$;

or $R^1$ and $R^2$ are taken together with the intervening atoms to which they are attached to form a 5- to 8-membered heterocycle, which is optionally substituted with one or more substituents independently selected from $R^9$;

or $R^2$ and $R^3$ are taken together with the intervening atoms to which they are attached to form a 4- to 10-membered heterocycle, which is optionally substituted with one or more substituents independently selected from $R^9$;

$R^4$, $R^5$, and $R^6$ are independently selected from:

hydrogen, halogen, —CN, —OH, —$OR^{11}$, —$C(=O)N(R^{10})_2$, and —$N(R^{10})_2$; and $C_1$-$C_6$ alkyl, $C_2$-$C_6$ alkenyl, and $C_2$-$C_6$ alkynyl, each of which is optionally substituted with one or more substituents independently selected from $R^9$;

each $R^9$ is independently selected from halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$SR^{12}$, —$S(=O)R^{13}$, —$SO_2R^{13}$, —$SO_2N(R^{12})_2$, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, and 3- to 6-membered heterocycle;

each $R^{10}$ is independently selected from hydrogen; and $C_1$-$C_6$ alkyl, $C_3$-$C_6$ carbocycle, and 3- to 6-membered heterocycle, each of which is optionally substituted with one or more substituents independently selected from $R^9$;

each $R^{11}$ is independently selected from $C_1$-$C_6$ alkyl, $C_3$-$C_6$ carbocycle, and 3- to 6-membered heterocycle, each of which is optionally substituted with one or more substituents independently selected from $R^9$;

each $R^{12}$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; and each $R^{13}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle.

In some embodiments, $R^A$ is an optionally substituted 9- or 10-membered bicyclic heteroaryl, wherein substituents on $R^A$ are independently selected from $R^a$. In some embodiments, $R^A$ is an optionally substituted indolyl, optionally substituted isoindolyl, optionally substituted indazolyl, optionally substituted benzimidazolyl, optionally substituted azaindolyl, optionally substituted pyrrolopyridinyl, optionally substituted pyrazolopyrimidinyl, optionally substituted imidazolopyrimidinyl, optionally substituted benzisoxazolyl, optionally substituted benzoxazolyl, optionally substituted benzoisoxazolyl, optionally substituted benzothiazolyl, optionally substituted benzoxadiazolyl, optionally substituted benzothiadiazolyl, optionally substituted quinolinyl, optionally substituted isoquinolinyl, optionally substituted quinoxalinyl, or optionally substituted quinazolinyl, wherein substituents on $R^A$ are independently selected from $R^a$. In some embodiments, $R^A$ is an optionally substituted indolyl, optionally substituted indazolyl, optionally substituted azaindolyl, optionally substituted pyrrolopyridinyl, optionally substituted pyrazolopyrimidinyl, optionally substituted quinolinyl, or optionally substituted imidazolopyrimidinyl, wherein substituents on $R^A$ are independently selected from $R^a$. In some embodiments, $R^A$ is

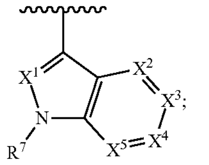

$X^1$, $X^2$, $X^3$, $X^4$, and $X^5$ are independently selected from $CR^8$ and N, wherein 0, 1, or 2 of $X^1$, $X^2$, $X^3$, $X^4$, and $X^5$ are N; $R^7$ is selected from: hydrogen; $C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from: hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$; $C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (I) is represented by Formula (II):

Formula (II)

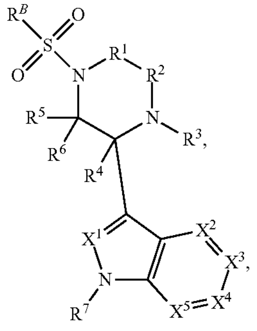

or a pharmaceutically acceptable salt thereof, wherein:

$X^1$, $X^2$, $X^3$, $X^4$, and $X^5$ are independently selected from $CR^8$ and N, wherein 0 or 1 of $X^1$, $X^2$, $X^3$, $X^4$, and $X^5$ are N;

$R^7$ is selected from:

hydrogen; and $C_1$-$C_6$ alkyl, $C_2$-$C_6$ alkenyl, and $C_2$-$C_6$ alkynyl, each of which is optionally substituted with one or more substituents independently selected from $R^9$;

each $R^8$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, $R^B$ is an optionally substituted 9- or 10-membered bicyclic heteroaryl, wherein substituents on $R^B$ are independently selected from $R^b$. In some embodiments, $R^B$ is an optionally substituted indolyl, optionally substituted isoindolyl, optionally substituted indazolyl, optionally substituted benzimidazolyl, optionally substituted azaindolyl, optionally substituted pyrazolopyrimidinyl, optionally substituted imidazolopyrimidinyl, optionally substituted benzisoxazolyl, optionally substituted benzoxazolyl, optionally substituted benzoisoxazolyl, optionally substituted benzothiazolyl, optionally substituted benzoxadiazolyl, optionally substituted benzothiadiazolyl, optionally substituted quinolinyl, optionally substituted isoquinolinyl, optionally substituted quinoxalinyl, or optionally substituted quinazolinyl, wherein substituents on $R^B$ are independently selected from $R^b$. In some embodiments, $R^B$ is an optionally substituted indolyl, optionally substituted benzimidazolyl, optionally substituted benzothiazolyl, optionally substituted quinolinyl, optionally substituted isoquinolinyl, or optionally substituted indazolyl, wherein substituents on $R^B$ are independently selected from $R^b$. In some embodiments, $R^B$ is

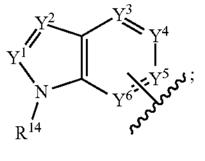

$Y^1$, $Y^2$, $Y^3$, $Y^4$, $Y^5$ and $Y^6$ are independently selected from $CR^{15}$ and N, wherein 0, 1, 2, or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule; $R^{14}$ is selected from: hydrogen; $C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^{15}$ is independently selected from: hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$; $C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (I) or Formula (II) is represented by Formula (III):

Formula (III)

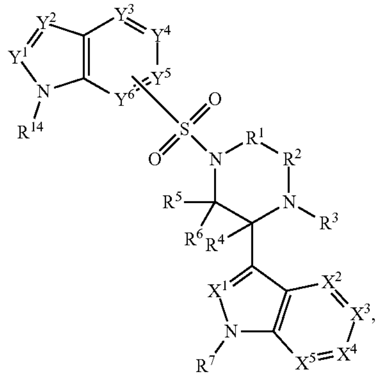

or a pharmaceutically acceptable salt thereof, wherein:

$Y^1$, $Y^2$, $Y^3$, $Y^4$, $Y^5$ and $Y^6$ are independently selected from $CR^{15}$ and N, wherein 0 or 1 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, the compounds of Formula (III) is represented by Formula (IIIa-3):

Formula (IIIa-3)

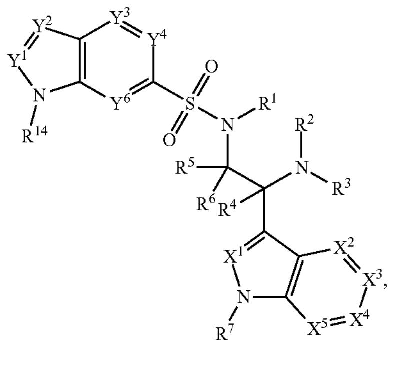

or a pharmaceutically acceptable salt thereof.

In some embodiments, the compounds of Formula (III) is represented by Formula (IIIb-3):

Formula (IIIb-3)

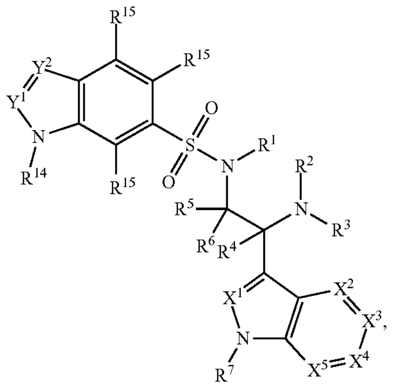

or a pharmaceutically acceptable salt thereof, wherein: 0 or 1 of $Y^1$ and $Y^2$ is N.

In some embodiments, the compounds of Formula (III) is represented by Formula (IIIc-3):

Formula (IIIc-3)

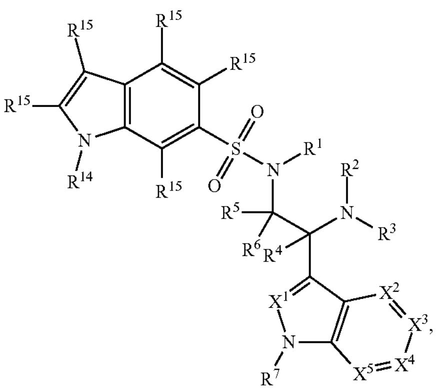

or a pharmaceutically acceptable salt thereof.

In some embodiments, $R^2$ and $R^3$ are independently selected from hydrogen; and $C_1$-$C_6$ alkyl, each of which is optionally substituted with one or more substituents independently selected from $R^9$. In some embodiments, $R^2$ and $R^3$ are independently selected from hydrogen; and $C_1$-$C_6$ alkyl. In some embodiments, $R^2$ and $R^3$ are independently selected from $C_1$-$C_6$ alkyl.

In some embodiments, $R^2$ and $R^3$ are taken together with the intervening atoms to which they are attached to form a 4- to 8-membered heterocycle, which is optionally substituted with one or more substituents independently selected from $R^9$. In some embodiments, $R^2$ and $R^3$ are taken together with the intervening atoms to which they are attached to form a 4- to 8-membered heterocycloalkyl, which is optionally substituted with one or more substituents independently selected from $R^9$. In some embodiments, $R^2$ and $R^3$ are taken together with the intervening atoms to which they are attached to form an optionally substituted azetidinyl, optionally substituted pyrrolidinyl, optionally substituted piperidinyl, optionally substituted morpholinyl, or optionally substituted tetrahydrofuropyrrolyl, which is optionally substituted with one or more substituents independently selected from $R^9$.

In some embodiments, $R^1$ is selected from hydrogen; and $C_1$-$C_6$ alkyl, which is optionally substituted with one or more substituents independently selected from $R^9$. In some embodiments, $R^1$ is selected from hydrogen; and $C_1$-$C_6$ alkyl. In some embodiments, $R^1$ is hydrogen.

In some embodiments, $R^1$ and $R^2$ are taken together with the intervening atoms to which they are attached to form a 5- to 8-membered heterocycloalkyl, which is optionally substituted with one or more substituents independently selected from $R^9$.

In some embodiments, the compounds of Formula (III) is represented by Formula (IIId-3):

Formula (IIId-3)

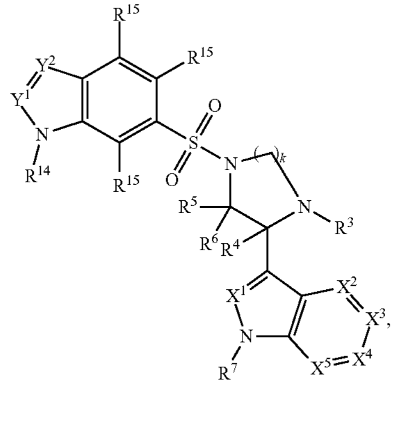

or a pharmaceutically acceptable salt thereof, wherein:

0 or 1 of $Y^1$ and $Y^2$ is N; and k is 1, 2, 3, or 4.

In some embodiments, k is 1 or 2.

In some embodiments, $R^4$, $R^5$, and $R^6$ are independently selected from: hydrogen, —$OR^{11}$, and —$N(R^{10})_2$; and $C_1$-$C_6$ alkyl, which is optionally substituted with one or more substituents independently selected from $R^9$. In some embodiments, $R^4$, $R^5$, and $R^6$ are each hydrogen.

In some embodiments, the compound of Formula (I) or Formula (II) is represented by Formula (IV):

Formula (IV)

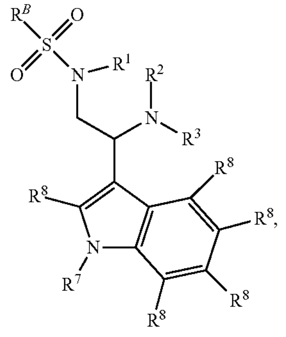

or a pharmaceutically acceptable salt thereof.

In some embodiments, the compound of Formula (IV) is represented by Formula (IVa):

Formula (IVa)

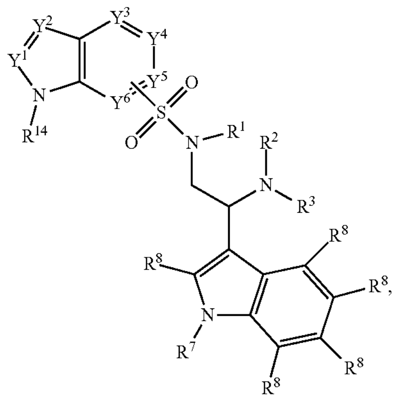

or a pharmaceutically acceptable salt thereof, wherein:

$Y^1$, $Y^2$, $Y^3$, $Y^4$, and $Y^5$ are independently selected from $CR^{15}$ and N, wherein 0, 1, 2 or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl which is optionally substituted with one or more substituents independently selected from $R^9$; and $C_3$-$C_6$ cycloalkyl and 3- to 6-membered heterocycloalkyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (IVa) is represented by Formula (IVb):

Formula (IVb)

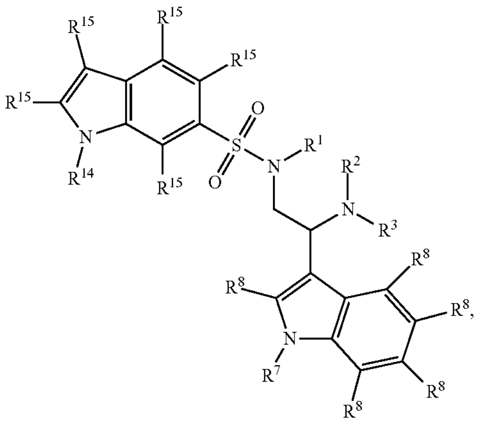

or a pharmaceutically acceptable salt thereof.

In some embodiments, $R^7$ is selected from: hydrogen; and $C_1$-$C_6$ alkyl which is optionally substituted with one or more substituents independently selected from $R^9$. In some embodiments, $R^7$ is selected from: hydrogen and $C_1$-$C_6$ alkyl. In some embodiments, $R^7$ is selected from hydrogen, methyl, ethyl, n-propyl, isopropyl, n-butyl, isobutyl, sec-butyl, tert-butyl, pentyl, and hexyl. In some embodiments, $R^7$ is selected from hydrogen and methyl.

In some embodiments, each $R^8$ is independently selected from: hydrogen, halogen, —CN, and —$OR^{13}$; and $C_1$-$C_6$ alkyl which is optionally substituted with one or more substituents independently selected from $R^9$. In some embodiments, each $R^8$ is independently selected from hydrogen, halogen, —CN, —$OR^{13}$, $C_1$-$C_6$ alkyl, $C_1$-$C_6$ fluoroalkyl, and $C_1$-$C_6$ hydroxyalkyl. In some embodiments, each $R^8$ is independently selected from hydrogen, halogen, —CN, —$OR^{13}$, and $C_1$-$C_6$ alkyl.

In some embodiments, each $R^{15}$ is independently selected from: hydrogen, halogen, —CN, —OH, —$OR^{13}$, —$N(R^{12})_2$, —C(=O)$OR^{12}$, and —$NR^{12}SO_2R^{13}$; and $C_1$-$C_6$ alkyl which is optionally substituted with one or more substituents independently selected from $R^9$. In some embodiments, each $R^{15}$ is independently selected from hydrogen, halogen, —CN, —OH, —$OR^{13}$, —$N(R^{12})_2$, $C_1$-$C_6$ alkyl, and $C_1$-$C_6$ fluoroalkyl.

In some embodiments, $R^{14}$ is selected from: hydrogen; and $C_1$-$C_3$ alkyl which is optionally substituted with one or more substituents independently selected from $R^9$. In some embodiments, $R^{14}$ is selected from hydrogen and $C_1$-$C_3$ alkyl. In some embodiments, $R^{14}$ is selected from hydrogen and methyl. In some embodiments, $R^{14}$ is hydrogen.

Any combination of the groups described above or below for the various variables is contemplated herein. Throughout the specification, groups and substituents thereof are chosen by one skilled in the field to provide stable moieties and compounds.

Also disclosed herein are pharmaceutical compositions comprising a compound described herein, or a pharmaceutically acceptable salt, solvate, or stereoisomer thereof, and a pharmaceutically acceptable excipient.

Also disclosed herein are methods for treating an ophthalmic disease comprising administering a compound or composition disclosed herein to the eye of a subject in need thereof. In some embodiments, the compound or composition is administered topically, by intravitreal injection or intracameral injection. In some embodiments, the ophthalmic disease is cataract. In some embodiments, the ophthalmic disease is presbyopia.

Also disclosed herein are methods of reducing aggregation of an α-crystallin protein by at least 5% in a subject in need thereof comprising administering a compound or composition disclosed herein to the eye of a subject in need thereof. In some embodiments, aggregation of an α-crystallin protein is reduced by at least 10%. In some embodiments, aggregation of an α-crystallin protein is reduced by at least 20%.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Definitions

Unless defined otherwise, all technical and scientific terms used herein have the same meaning as is commonly understood by one of skill in the art to which this invention belongs.

All patents and publications referred to herein are incorporated by reference.

As used in the specification and claims, the singular form "a", "an" and "the" includes plural references unless the context clearly dictates otherwise.

"Alkyl" refers to a straight or branched hydrocarbon chain radical consisting solely of carbon and hydrogen atoms, containing no unsaturation, and preferably having from one to fifteen carbon atoms (i.e., $C_1$-$C_{15}$ alkyl). In certain embodiments, an alkyl comprises one to thirteen carbon atoms (i.e., $C_1$-$C_{13}$ alkyl). In certain embodiments, an alkyl comprises one to eight carbon atoms (i.e., $C_1$-$C_8$ alkyl). In other embodiments, an alkyl comprises one to five carbon atoms (i.e., $C_1$-$C_5$ alkyl). In other embodiments, an alkyl comprises one to four carbon atoms (i.e., $C_1$-$C_4$ alkyl). In other embodiments, an alkyl comprises one to three carbon atoms (i.e., $C_1$-$C_3$ alkyl). In other embodiments, an alkyl comprises one to two carbon atoms (i.e., $C_1$-$C_2$ alkyl). In other embodiments, an alkyl comprises one carbon atom (i.e., $C_1$ alkyl). In other embodiments, an alkyl comprises five to fifteen carbon atoms (i.e., $C_5$-$C_{15}$ alkyl). In other embodiments, an alkyl comprises five to eight carbon atoms (i.e., $C_5$-$C_8$ alkyl). In other embodiments, an alkyl comprises two to five carbon atoms (i.e., $C_2$-$C_5$ alkyl). In other embodiments, an alkyl comprises three to five carbon atoms (i.e., $C_3$-$C_5$ alkyl). In certain embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more substituents such as those substituents described herein.

"Alkenyl" refers to a straight or branched hydrocarbon chain radical group consisting solely of carbon and hydrogen atoms, containing at least one carbon-carbon double bond, and preferably having from two to twelve carbon atoms (i.e., $C_2$-$C_{12}$ alkenyl). In certain embodiments, an alkenyl comprises two to ten carbon atoms (i.e., $C_2$-$C_{10}$ alkenyl). In certain embodiments, an alkenyl comprises two to eight carbon atoms (i.e., $C_2$-$C_8$ alkenyl). In other embodiments, an alkenyl comprises two to six carbon atoms (i.e., $C_2$-$C_6$ alkenyl). The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to a straight or branched hydrocarbon chain radical group consisting solely of carbon and hydrogen atoms, containing at least one carbon-carbon triple bond, and preferably having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl comprises two to six carbon atoms (i.e., $C_2$-$C_6$ alkynyl). In other embodiments, an alkynyl comprises two to four carbon atoms (i.e., $C_2$-$C_4$ alkynyl). The alkynyl may be attached to the rest of the molecule by a single bond, for example, ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to a straight or branched divalent hydrocarbon chain linking the rest of the molecule to a radical group, consisting solely of carbon and hydrogen, containing no unsaturation, and preferably having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group may be through any two carbons within the chain. In certain embodiments, an alkylene comprises one to ten carbon atoms (i.e., $C_1$-$C_8$ alkylene). In certain embodiments, an alkylene comprises one to eight carbon atoms (i.e., $C_1$-$C_8$ alkylene). In other embodiments, an alkylene comprises one to five carbon atoms (i.e., $C_1$-$C_5$ alkylene). In other embodiments, an alkylene comprises one to four carbon atoms (i.e., $C_1$-$C_4$ alkylene). In other embodiments, an alkylene comprises one to three carbon atoms (i.e., $C_1$-$C_3$ alkylene). In other embodiments, an alkylene comprises one to two carbon atoms (i.e., $C_1$-$C_2$ alkylene). In other embodiments, an alkylene comprises one carbon atom (i.e., $C_1$ alkylene). In other embodiments, an alkylene comprises five to eight carbon atoms (i.e., $C_5$-$C_8$ alkylene). In other embodiments, an alkylene comprises two to five carbon atoms (i.e., $C_2$-$C_5$ alkylene). In other embodiments, an alkylene comprises three to five carbon atoms (i.e., $C_3$-$C_5$ alkylene). Unless stated otherwise specifically in the specification, an alkylene chain is optionally substituted by one or more substituents such as those substituents described herein.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and preferably having from two to twelve carbon atoms. The alkenylene chain is attached to the rest of the molecule through a single bond and to the radical group through a single bond. The points of attachment of the alkenylene chain to the rest of the molecule and to the radical group may be through any two carbons within the chain. In certain embodiments, an alkenylene comprises two to ten carbon atoms (i.e., $C_2$-$C_{10}$ alkenylene). In certain embodiments, an alkenylene comprises two to eight carbon atoms (i.e., $C_2$-$C_8$ alkenylene). In other embodiments, an alkenylene comprises two to five carbon atoms (i.e., $C_2$-$C_5$ alkenylene). In other embodiments, an alkenylene comprises two to four carbon atoms (i.e., $C_2$-$C_4$ alkenylene). In other embodiments, an alkenylene comprises two to three carbon atoms (i.e., $C_2$-$C_3$ alkenylene). In other embodiments, an alkenylene comprises two carbon atom (i.e., $C_2$ alkenylene). In other embodiments, an alkenylene comprises five to eight carbon atoms (i.e., $C_5$-$C_8$ alkenylene). In other embodiments, an alkenylene comprises three to five carbon atoms (i.e., $C_3$-$C_5$ alkenylene). Unless stated otherwise specifically in the specification, an alkenylene chain is optionally substituted by one or more substituents such as those substituents described herein.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and preferably having from two to twelve carbon atoms. The alkynylene chain is attached to the rest of the molecule through a single bond and to the radical group through a single bond. The points of attachment of the alkynylene chain to the rest of the molecule and to the radical group may be through any two carbons within the chain. In certain embodiments, an alkynylene comprises two to ten carbon atoms (i.e., $C_2$-$C_{10}$ alkynylene). In certain embodiments, an alkynylene comprises two to eight carbon atoms (i.e., $C_2$-$C_8$ alkynylene). In other embodiments, an alkynylene comprises two to five carbon atoms (i.e., $C_2$-$C_5$ alkynylene). In other embodiments, an alkynylene comprises two to four carbon atoms (i.e., $C_2$-$C_4$ alkynylene). In other embodiments, an alkynylene comprises two to three carbon atoms (i.e., $C_2$-$C_3$ alkynylene). In other embodiments, an alkynylene comprises two carbon atom (i.e., $C_2$ alkynylene). In other embodiments, an alkynylene comprises five to eight carbon atoms (i.e., $C_5$-$C_8$ alkynylene). In other embodiments, an alkynylene comprises three to five carbon atoms (i.e., $C_3$-$C_5$ alkynylene). Unless stated otherwise specifically in the specification, an alkynylene chain is optionally substituted by one or more substituents such as those substituents described herein.

"Aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents such as those substituents described herein.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as described above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as described above for an alkynylene chain.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain. The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond respectively.

"Carbocycle" refers to a saturated, unsaturated or aromatic rings in which each atom of the ring is carbon. Carbocycle may be monocyclic or polycyclic and may include 3- to 10-membered monocyclic rings, 6- to 12-membered bicyclic rings, and 6- to 12-membered bridged rings. Each ring of a bicyclic carbocycle may be selected from saturated, unsaturated, and aromatic rings. In some embodiments, the carbocycle is an aryl. In some embodiments, the carbocycle is a cycloalkyl. In some embodiments, the carbocycle is a cycloalkenyl. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, are included in the definition of carbocyclic. Exemplary carbocycles include cyclopentyl, cyclohexyl, cyclohexenyl, adamantyl, phenyl, indanyl, and naphthyl. Unless stated otherwise specifically in the specification, a carbocycle is optionally substituted by one or more substituents such as those substituents described herein.

"Cycloalkyl" refers to a saturated ring in which each atom of the ring is carbon. Cycloalkyl may include monocyclic and polycyclic rings such as 3- to 10-membered monocyclic rings, 6- to 12-membered bicyclic rings, and 6- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals that are optionally substituted by one or more substituents such as those substituents described herein.

"Cycloalkenyl" refers to a saturated ring in which each atom of the ring is carbon and there is at least one double bond between two ring carbons. Cycloalkenyl may include monocyclic and polycyclic rings such as 3- to 10-membered monocyclic rings, 6- to 12-membered bicyclic rings, and 6- to 12-membered bridged rings. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl. Unless otherwise stated specifically in the specification, the term "cycloalkenyl" is meant to include cycloalkenyl radicals that are optionally substituted by one or more substituents such as those substituents described herein.

"Halo" or, alternatively, "halogen" or "halide," means fluoro, chloro, bromo or iodo. In some embodiments, halo is fluoro, chloro, or bromo.

"Haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally substituted as described herein.

"Hydroxyalkyl" refers to an alkyl radical, as defined above, that is substituted by one or more hydroxy radicals, for example, hydroxymethyl, 2-hydroxyethyl, 2-hydroxypropyl, 3-hydroxypropyl, and the like. In some embodiments, the alkyl part of the hydroxyalkyl radical is optionally substituted as described herein.

"Heterocycle" refers to a saturated, unsaturated or aromatic ring comprising carbon atoms and one or more heteroatoms. Exemplary heteroatoms include N, O, Si, P, B, and S atoms.

Heterocycle may be monocyclic or polycyclic and may include 3- to 10-membered monocyclic rings, 6- to 12-membered bicyclic rings, and 6- to 12-membered bridged rings. Each ring of a bicyclic heterocycle may be selected from saturated, unsaturated, and aromatic rings. In some embodiments, the heterocycle is a heteroaryl. In some embodiments, the heterocycle is a heterocycloalkyl. In an exemplary embodiment, a heterocycle, e.g., pyridyl, may be fused to a saturated or unsaturated ring, e.g., cyclohexane, cyclopentane, or cyclohexene.

"Heterocycloalkyl" refers to a saturated ring with carbon atoms and at least one heteroatom. Exemplary heteroatoms include N, O, Si, P, B, and S atoms. Heterocycloalkyl may include monocyclic and polycyclic rings such as 3- to 10-membered monocyclic rings, 6- to 12-membered bicyclic rings, and 6- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents such as those substituents described herein.

"Heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N, O, Si, P, B, and S atoms.

Heterocycloalkenyl may include monocyclic and polycyclic rings such as 3- to 10-membered monocyclic rings, 6- to 12-membered bicyclic rings, and 6- to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazole), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydrooxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazine, and dihydrothiazine. Unless otherwise stated specifically in the specification, the term “heterocycloalkenyl” is meant to include heterocycloalkenyl radicals that are optionally substituted by one or more substituents such as those substituents described herein.

“Heteroaryl” refers to an aromatic ring comprising carbon atoms and one or more heteroatoms. Exemplary heteroatoms include N, O, Si, P, B, and S atoms. As used herein, the heteroaryl ring may be selected from monocyclic or bicyclic and fused or bridged ring systems rings wherein at least one of the rings in the ring system is aromatic, i.e., it contains a cyclic, delocalized (4n+2) π-electron system in accordance with the Hückel theory. The heteroatom(s) in the heteroaryl radical may be optionally oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term “heteroaryl” is meant to include heteroaryl radicals as defined above which are optionally substituted by one or more substituents such as those substituents described herein.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term “geometric isomer” refers to E or Z geometric isomers (e.g., cis or trans) of an alkene double bond. The term “positional isomer” refers to structural isomers around a central ring, such as ortho-, meta-, and para-isomers around a phenyl ring.

A “tautomer” refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. Unless otherwise stated, chemical structures depicted herein are intended to include structures which are different tautomers of the structures depicted. For example, the chemical structure depicted with an enol moiety also includes the keto tautomer form of the enol moiety. The exact ratio of the tautomers depends on several factors, including physical state, temperature, solvent, and pH. Some examples of tautomeric equilibrium include:

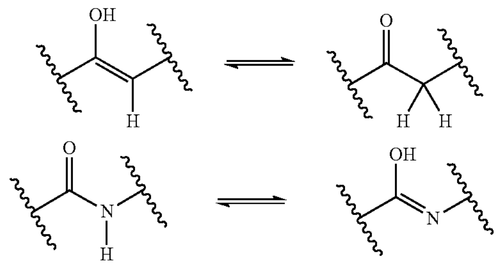

-continued

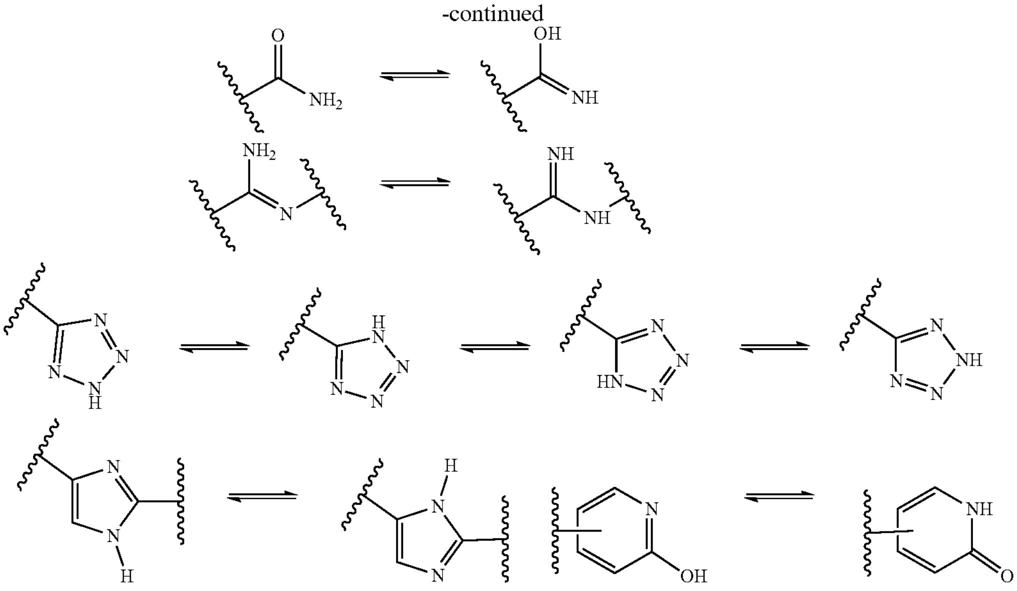

The compounds disclosed herein, in some embodiments, are used in different enriched isotopic forms, e.g., enriched in the content of $^{2}H$, $^{3}H$, $^{11}C$, $^{13}C$ and/or $^{14}C$. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of the present disclosure.

The compounds of the present disclosure optionally contain unnatural proportions of atomic isotopes at one or more atoms that constitute such compounds. For example, the compounds may be labeled with isotopes, such as deuterium ($^{2}H$), tritium ($^{3}H$), iodine-125 ($^{125}I$) or carbon-14 ($^{14}C$). Isotopic substitution with $^{2}H$, $^{11}C$, $^{13}C$, $^{14}C$, $^{15}C$, $^{12}N$, $^{13}N$, $^{15}N$, $^{16}N$, $^{16}O$, $^{17}O$, $^{14}F$, $^{15}F$, $^{16}F$, $^{17}F$, $^{18}F$, $^{33}S$, $^{34}S$, $^{35}S$, $^{36}S$, $^{35}Cl$, $^{37}Cl$, $^{79}Br$, $^{81}Br$, $^{125}I$ are all contemplated. All isotopic variations of the compounds of the present invention, whether radioactive or not, are encompassed within the scope of the present invention.

In certain embodiments, the compounds disclosed herein have some or all of the $^{1}H$ atoms replaced with $^{2}H$ atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Deuterium-transfer reagents suitable for use in nucleophilic substitution reactions, such as iodomethane-$d_3$ ($CD_3I$), are readily available and may be employed to transfer a deuterium-substituted carbon atom under nucleophilic substitution reaction conditions to the reaction substrate. The use of $CD_3I$ is illustrated, by way of example only, in the reaction schemes below.

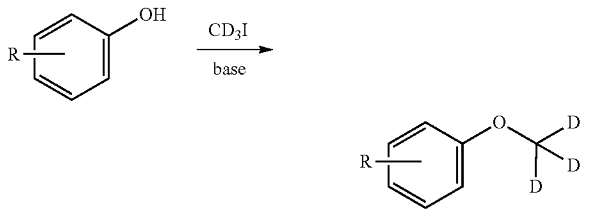

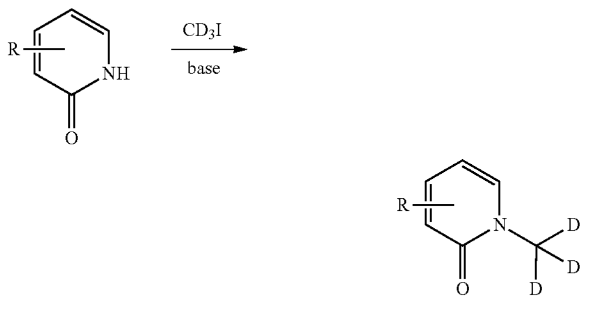

Deuterium-transfer reagents, such as lithium aluminum deuteride ($LiAlD_4$), are employed to transfer deuterium under reducing conditions to the reaction substrate. The use of $LiAlD_4$ is illustrated, by way of example only, in the reaction schemes below.

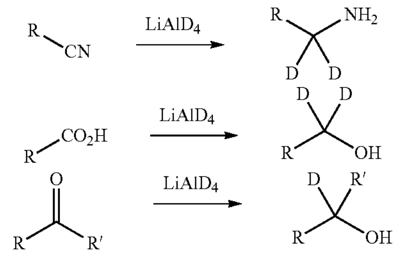

Deuterium gas and palladium catalyst are employed to reduce unsaturated carbon-carbon linkages and to perform a reductive substitution of aryl carbon-halogen bonds as illustrated, by way of example only, in the reaction schemes below.

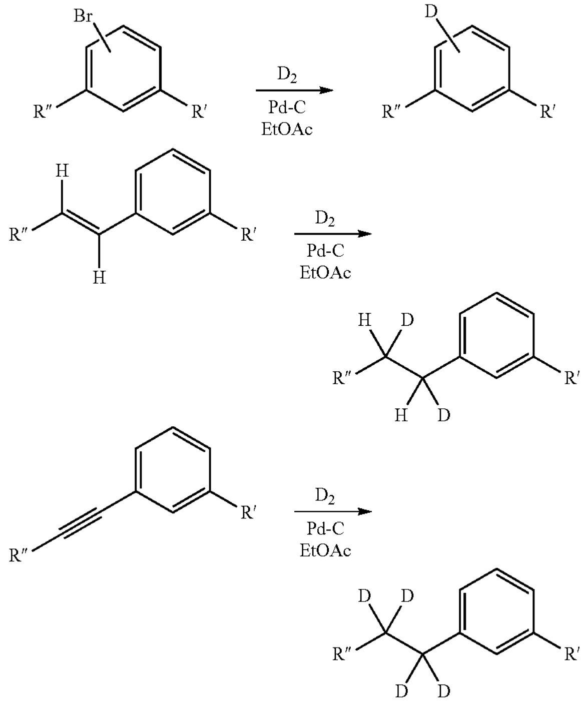

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

In some embodiments, the pharmaceutically acceptable base addition salt is chosen from ammonium, potassium, sodium, calcium, and magnesium salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier is "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

For purposes of this disclosure, the heteroatoms such as nitrogen may have hydrogen substituents and/or any permissible substituents of organic compounds described herein which satisfy the valences of the heteroatoms.

Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, a carbocycle, a heterocycle, a cycloalkyl, a heterocycloalkyl, an aromatic and heteroaromatic moiety. In some embodiments, substituents may include any substituents described herein, for example: halogen, hydroxy, oxo (═O), thioxo (═S), cyano (—CN), nitro (—$NO_2$), imino (═N—H), oximo (═N—OH), hydrazino (═N—$NH_2$), —$R^b$—$OR^a$, —$R^b$—OC(O)—$R^a$, —$R^b$—OC(O)—$OR^a$, —$R^b$—OC(O)—$N(R^a)_2$, —$R^b$—N$(R^a)_2$, —$R^b$—C(O)$R^a$, —$R^b$—C(O)$OR^a$, —$R^b$—C(O)N$(R^a)_2$, —$R^b$—O—$R^c$—C(O)N$(R^a)_2$, —$R^b$—N($R^a$)C(O)$OR^a$, —$R^b$—N($R^a$)C(O)$R^a$, —$R^b$—N($R^a$)S$(O)_tR^a$ (where t is 1 or 2), —$R^b$—S$(O)_tR^a$ (where t is 1 or 2), —$R^b$—S$(O)_t$$OR^a$ (where t is 1 or 2), and —$R^b$—S$(O)_t$N$(R^a)_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl any of which may be optionally substituted by alkyl, alkenyl, alkynyl, halogen, hydroxy, haloalkyl, haloalkenyl, haloalkynyl, oxo (═O), thioxo (═S), cyano (—CN), nitro (—$NO_2$), imino (═N—H), oximo (═N—OH), hydrazine (═N—$NH_2$), —$R^b$—$OR^a$, —$R^b$—OC(O)—$R^a$, —$R^b$—OC(O)—$OR^a$, —$R^b$—OC(O)—N$(R^a)_2$, —$R^b$—N$(R^a)_2$, —$R^b$—C(O)$R^a$, —$R^b$—C(O)$OR^a$, —$R^b$—C(O)N$(R^a)_2$, —$R^b$—O—$R^c$—C(O)N$(R^a)_2$, —$R^b$—N($R^a$)C(O)$OR^a$, —$R^b$—N($R^a$)C(O)$R^a$, —$R^b$—N($R^a$)S$(O)_tR^a$ (where t is 1 or 2), —$R^b$—S$(O)_tR^a$ (where t is 1 or 2), —$R^b$—S$(O)_t$$OR^a$ (where t is 1 or 2) and —$R^b$—S$(O)_t$N$(R^a)_2$ (where t is 1 or 2); wherein each $R^a$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^a$, valence permitting, may be optionally substituted with alkyl, alkenyl, alkynyl, halogen, haloalkyl, haloalkenyl, haloalkynyl, oxo (═O), thioxo (═S), cyano (—CN), nitro (—$NO_2$), imino (═N—H), oximo (═N—OH), hydrazine (═N—$NH_2$), —$R^b$—$OR^a$, —$R^b$—OC(O)—$R^a$, —$R^b$—OC(O)—$OR^a$, —$R^b$—OC(O)—N$(R^a)_2$, —$R^b$—N$(R^a)_2$, —$R^b$—C(O)$R^a$, —$R^b$—C(O)$OR^a$, —$R^b$—C(O)N$(R^a)_2$, —$R^b$—O—$R^c$—C(O)N$(R^a)_2$, —$R^b$—N($R^a$)C(O)$OR^a$, —$R^b$—N($R^a$)C(O)$R^a$, —$R^b$—N($R^a$)S$(O)_tR^a$ (where t is 1 or 2), —$R^b$—S$(O)_tR^a$ (where t is 1 or 2), —$R^b$—S$(O)_t$$OR^a$ (where t is 1 or 2) and —$R^b$—S$(O)_t$N$(R^a)_2$ (where t is 1 or 2); and wherein each $R^b$ is independently selected from a direct bond or a straight or branched alkylene, alkenylene, or alkynylene chain, and each $R^c$ is a straight or branched alkylene, alkenylene or alkynylene chain.

The terms "treat," "treating" or "treatment," as used herein, may include alleviating, abating or ameliorating a disease or condition symptoms, preventing additional symptoms, ameliorating or preventing the underlying causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Compounds of the present invention also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Introduction

Alpha-crystallin is a major structural protein found in the eye and can maintain the refractive index and transparency of the lens. Alpha-crystallin is composed of two homologous subunits: alphaA-crystallin (cryAA) and alphaB-crystallin (cryAB), which belong to a family of small heat shock proteins (sHSPs) that contain a conserved crystallin domain. AlphaA is 173 amino acids long and alphaB is 175 amino acid long. The two alpha-crystallin genes, alphaA and alphaB, encode for proteins that share 57% sequence identity. The ratio of alphaA to alphaB in most vertebrate lenses can be 3:1 but this ratio can vary with species and age. The alphaA-crystallin protein can be found mostly in the lens and only in few other tissues whereas alphaB-crystallin protein can be ubiquitously expressed and can be found in other tissues, such as brain, heart and muscle.

These alpha-crystallin subunits act as molecular chaperones to prevent the cellular aggregation and inactivation of client proteins under a variety of stress conditions. However, the chaperone activity of these alpha-crystallin subunits can be lost or deteriorated during aging or due to certain genetic or environment factors, which can cause aggregation and precipitation of alpha-crystallin and lead to cataracts.

In certain embodiments, the disclosure provides compounds, formulations and methods for treating vision disorders associated with alpha-crystallin protein aggregation in the lens. In particular, the disclosure provides compounds, formulations and methods for treating cataract and presbyopia.

Compounds of the Disclosure

The present disclosure provides compounds and salts, and formulations thereof, for use in the treatment of ophthalmic diseases. The disclosed compounds and salts can be used, for example, for the treatment or prevention of vision disorders such as near vision impairment. In certain embodiments, the compounds of the disclosure reduce alpha-crystallin protein aggregation in the lens of an eye. Compounds and salts of the disclosure may be used in the formulations, methods and combination therapies described herein. In certain embodiments, compounds and salts of the disclosure are used in the treatment or prevention of cataract or presbyopia.

In one aspect, provided herein are compounds of Formula (I):

Formula (I)

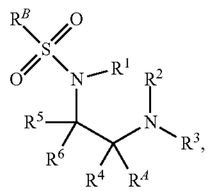

or a pharmaceutically acceptable salt thereof, wherein:

$R^A$ is an optionally substituted bicyclic heteroaryl, wherein substituents on $R^A$ are independently selected from $R^a$;

each $R^a$ is independently selected from:

halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$NR^{12}SO_2R^{12}$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_{10}$ carbocycle and 3- to 10-membered heterocycle, each of which is optionally substituted with one or more substituents independently selected from $R^9$;

$R^B$ is an optionally substituted bicyclic heteroaryl, wherein substituents on $R^B$ are independently selected from $R^b$;

each $R^b$ is independently selected from:

halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$SR^{12}$, —$S(=O)R^{13}$, —$SO_2R^{13}$, —$SO_2N(R^{12})_2$, —$NR^{12}SO_2R^{13}$, —$NO_2$;

$C_1$-$C_6$ alkyl, $C_2$-$C_6$ alkenyl, and $C_2$-$C_6$ alkynyl; each of which is optionally substituted with one or more substituents independently selected from $R^9$; and $C_3$-$C_{10}$ carbocycle and 3- to 10-membered heterocycle, each of which is optionally substituted with one or more substituents independently selected from $R^9$;

$R^1$ is selected from hydrogen; and $C_1$-$C_6$ alkyl, $C_2$-$C_6$ alkenyl, $C_2$-$C_6$ alkynyl, each of which is optionally substituted with one or more substituents independently selected from $R^9$;

$R^2$ and $R^3$ are independently selected from hydrogen; and $C_1$-$C_6$ alkyl, $C_2$-$C_6$ alkenyl, $C_2$-$C_6$ alkynyl, $C_3$-$C_6$ carbocycle, and 3- to 6-membered heterocycle, each of which is optionally substituted with one or more substituents independently selected from $R^9$;

or $R^1$ and $R^2$ are taken together with the intervening atoms to which they are attached to form a 5- to 8-membered heterocycle, which is optionally substituted with one or more substituents independently selected from $R^9$;

or $R^2$ and $R^3$ are taken together with the intervening atoms to which they are attached to form a 4- to 10-membered heterocycle, which is optionally substituted with one or more substituents independently selected from $R^9$;

$R^4$, $R^5$, and $R^6$ are independently selected from:

hydrogen, halogen, —CN, —OH, —$OR^{11}$, —$C(=O)N(R^{10})_2$, and —$N(R^{10})_2$; and $C_1$-$C_6$ alkyl, $C_2$-$C_6$ alkenyl, and $C_2$-$C_6$ alkynyl, each of which is optionally substituted with one or more substituents independently selected from $R^9$;

each $R^9$ is independently selected from halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$SR^{12}$, —$S(=O)R^{13}$, —$SO_2R^{13}$, —$SO_2N(R^{12})_2$, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, and 3- to 6-membered heterocycle;

each $R^{10}$ is independently selected from hydrogen; and $C_1$-$C_6$ alkyl, $C_3$-$C_6$ carbocycle, and 3- to 6-membered heterocycle, each of which is optionally substituted with one or more substituents independently selected from $R^9$;

each $R^{11}$ is independently selected from $C_1$-$C_6$ alkyl, $C_3$-$C_6$ carbocycle, and 3- to 6-membered heterocycle, each of which is optionally substituted with one or more substituents independently selected from $R^9$;

each $R^{12}$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; and each $R^{13}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle Any combination of the groups described above for the various variables is contemplated herein. Throughout the specification, groups and substituents thereof are chosen by one skilled in the field to provide stable moieties and compounds. For example, in some embodiments, $R^A$ is an optionally substituted 9- or 10-membered bicyclic heteroaryl, wherein substituents on $R^A$ are independently selected from $R^a$.

In some embodiments, $R^A$ is an optionally substituted indolyl, optionally substituted isoindolyl, optionally substituted indazolyl, optionally substituted benzimidazolyl, optionally substituted azaindolyl, optionally substituted pyrrolopyridinyl, optionally substituted pyrazolopyrimidinyl, optionally substituted imidazolopyrimidinyl, optionally substituted benzisoxazolyl, optionally substituted benzoxazolyl, optionally substituted benzoisoxazolyl, optionally substituted benzothiazolyl, optionally substituted benzoxadiazolyl, optionally substituted benzothiadiazolyl, optionally substituted quinolinyl, optionally substituted isoquinolinyl, optionally substituted quinoxalinyl, or optionally substituted quinazolinyl, wherein substituents on $R^A$ are independently selected from $R^a$. In some embodiments, $R^A$ is an optionally substituted indolyl, optionally substituted indazolyl, optionally substituted azaindolyl, optionally substituted pyrrolopyridinyl, optionally substituted pyrazolopyrimidinyl, optionally substituted quinolinyl, or optionally substituted imidazolopyrimidinyl, wherein substituents on $R^A$ are independently selected from $R^a$. In some embodiments, $R^A$ is an optionally substituted indolyl, optionally substituted benzimidazolyl, or optionally substituted indazolyl, wherein substituents on $R^A$ are independently selected from $R^a$. In some embodiments, $R^A$ is an optionally substituted indolyl, wherein substituents on $R^A$ are independently selected from $R^a$. In some embodiments, $R^A$ is an optionally substituted N-substituted indole, wherein substituents on $R^A$ are independently selected from $R^a$. In some embodiments, $R^A$ is an optionally substituted N-alkylindole, wherein substituents on $R^A$ are independently selected from $R^a$. In some embodiments, $R^A$ is an optionally substituted N-methylindole, wherein substituents on $R^A$ are independently selected from $R^a$.

In some embodiments, $R^A$ is

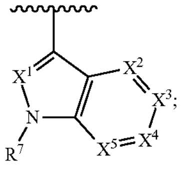

wherein:

$X^1$, $X^2$, $X^3$, $X^4$, and $X^5$ are independently selected from $CR^8$ and N, wherein 0, 1, or 2 of $X^1$, $X^2$, $X^3$, $X^4$, and $X^5$ are N;

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (I) is represented by Formula (II):

Formula (II)

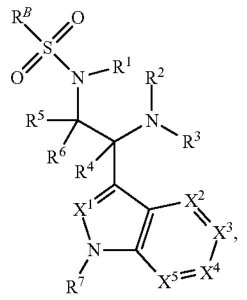

or a pharmaceutically acceptable salt thereof, wherein:

$X^1$, $X^2$, $X^3$, $X^4$, and $X^5$ are independently selected from $CR^8$ and N, wherein 0, 1, or 2 of $X^1$, $X^2$, $X^3$, $X^4$, and $X^5$ are N;

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, $R^7$ is selected from:

hydrogen; and $C_1$-$C_6$ alkyl, $C_2$-$C_6$ alkenyl, and $C_2$-$C_6$ alkynyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, 0 or 1 of $X^1$, $X^2$, $X^3$, $X^4$, and $X^5$ are N.

In some embodiments, $X^1$ is $CR^8$; and $X^2$, $X^3$, $X^4$, and $X^5$ are independently selected from $CR^8$ and N, wherein 0, 1, or 2 of $X^2$, $X^3$, $X^4$, and $X^5$ are N. In some embodiments, $X^1$ is $CR^8$; and $X^2$, $X^3$, $X^4$, and $X^5$ are independently selected from $CR^8$ and N, wherein 0 or 1 of $X^2$, $X^3$, $X^4$, and $X^5$ are N.

In some embodiments, $X^1$ is $CR^8$; $X^2$ is $CR^8$; $X^3$ is $CR^8$; $X^4$ is $CR^8$; and $X^5$ is $CR^8$.

In some embodiments, $X^1$ is N; $X^2$ is $CR^8$; $X^3$ is $CR^8$; $X^4$ is $CR^8$; and $X^5$ is $CR^8$.

In some embodiments, $X^1$ is $CR^8$; $X^2$ is N; $X^3$ is $CR^8$; $X^4$ is $CR^8$; and $X^5$ is $CR^8$.

In some embodiments, $X^1$ is $CR^8$; $X^2$ is $CR^8$; $X^3$ is N; $X^4$ is $CR^8$; and $X^5$ is $CR^8$.

In some embodiments, $X^1$ is $CR^8$; $X^2$ is $CR^8$; $X^3$ is $CR^8$; $X^4$ is N; and $X^5$ is $CR^8$.

In some embodiments, $X^1$ is $CR^8$; $X^2$ is $CR^8$; $X^3$ is $CR^8$; $X^4$ is $CR^8$; and $X^5$ is N.

In some embodiments, $R^B$ is an optionally substituted 9- or 10-membered bicyclic heteroaryl, wherein substituents on $R^B$ are independently selected from $R^b$.

In some embodiments, $R^B$ is an optionally substituted indolyl, optionally substituted isoindolyl, optionally substituted indazolyl, optionally substituted benzimidazolyl, optionally substituted azaindolyl, optionally substituted pyrrolopyridinyl, optionally substituted pyrazolopyrimidinyl, optionally substituted imidazolopyrimidinyl, optionally substituted benzisoxazolyl, optionally substituted benzoxazolyl, optionally substituted benzoisoxazolyl, optionally substituted benzothiazolyl, optionally substituted benzoxadiazolyl, optionally substituted benzothiadiazolyl, optionally substituted quinolinyl, optionally substituted isoquinolinyl, optionally substituted quinoxalinyl, or optionally substituted quinazolinyl, wherein substituents on $R^B$ are independently selected from $R^b$. In some embodiments, $R^B$ is an optionally substituted indolyl, optionally substituted isoindolyl, optionally substituted indazolyl, optionally substituted benzimidazolyl, optionally substituted azaindolyl, optionally substituted pyrazolopyrimidinyl, optionally substituted imidazolopyrimidinyl, optionally substituted benzisoxazolyl, optionally substituted benzoxazolyl, optionally substituted benzoisoxazolyl, optionally substituted benzothiazolyl, optionally substituted benzoxadiazolyl, optionally substituted benzothiadiazolyl, optionally substituted quinolinyl, optionally substituted isoquinolinyl, optionally substituted quinoxalinyl, or optionally substituted quinazolinyl, wherein substituents on $R^B$ are independently selected from $R^b$. In some embodiments, $R^B$ is an optionally substituted indolyl, optionally substituted benzimidazolyl, optionally substituted benzothiazolyl, optionally substituted quinolinyl, optionally substituted isoquinolinyl, or optionally substituted indazolyl, wherein substituents on $R^B$ are independently selected from $R^b$. In some embodiments, $R^B$ is an optionally substituted indolyl, optionally substituted benzimidazolyl, or optionally substituted indazolyl, wherein substituents on $R^B$ are independently selected from $R^b$. In some embodiments, $R^B$ is an optionally substituted indolyl, wherein substituents on $R^B$ are independently selected from $R^b$.

In some embodiments, $R^B$ is

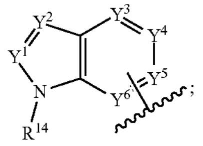

wherein:

$Y^1$, $Y^2$, $Y^3$, $Y^4$, $Y^5$ and $Y^6$ are independently selected from $CR^{15}$ and N, wherein 0, 1, 2, or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (I) or Formula (II) is represented by Formula (III):

Formula (III)

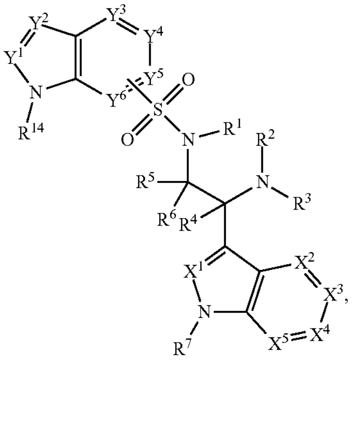

or a pharmaceutically acceptable salt thereof, wherein:

$Y^1$, $Y^2$, $Y^3$, $Y^4$, $Y^5$ and $Y^6$ are independently selected from $CR^{15}$ and N, wherein 0, 1, 2, or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, $R^{14}$ is selected from:

hydrogen; and $C_1$-$C_6$ alkyl, $C_2$-$C_6$ alkenyl, and $C_2$-$C_6$ alkynyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, $Y^1$, $Y^2$, $Y^3$, $Y^4$, $Y^5$ and $Y^6$ are independently selected from $CR^{15}$ and N, wherein 0 or 1 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule.

In some embodiments, $Y^1$ is $CR^{15}$; and $Y^2$, $Y^3$, $Y^4$, $Y^5$ and $Y^6$ are independently selected from $CR^{15}$ and N, wherein 0, 1, or 2 of $Y^2$, $Y^3$, $Y^4$, $Y^5$ and $Y^6$ are N; and wherein one of $Y^2$, $Y^3$, $Y^4$, $Y^5$, and $Y^6$ is the attachment point to the rest of the molecule. In some embodiments, $Y^1$ is $CR^{15}$; and $Y^2$, $Y^3$, $Y^4$, $Y^5$ and $Y^6$ are independently selected from $CR^{15}$ and N, wherein 0 or 1 of $Y^2$, $Y^3$, $Y^4$, $Y^5$ and $Y^6$ are N; and wherein one of $Y^1$, $Y^2$, $Y^3$, $Y^4$, $Y^5$, and $Y^6$ is the attachment point to the rest of the molecule. In some embodiments, $Y^1$ is $CR^{15}$; and $Y^2$, $Y^3$, $Y^4$, $Y^5$ and $Y^6$ are independently selected from $CR^{15}$ and N, wherein 0 or 1 of $Y^2$, $Y^3$, $Y^4$, $Y^5$ and $Y^6$ are N; and wherein one of $Y^3$, $Y^4$, $Y^5$, and $Y^6$ is the attachment point to the rest of the molecule.

In some embodiments, $Y^1$ is $CR^{15}$; $Y^2$ is $CR^{15}$; $Y^3$ is $CR^{15}$; $Y^4$ is $CR^{15}$; $Y^5$ is $CR^{15}$; and $Y^6$ is $CR^{15}$; wherein one of $Y^3$, $Y^4$, $Y^5$, and $Y^6$ is the attachment point to the rest of the molecule.

In some embodiments, $Y^1$ is N; $Y^2$ is $CR^{15}$; $Y^3$ is $CR^{15}$; $Y^4$ is $CR^{15}$; $Y^5$ is $CR^{15}$; and $Y^6$ is $CR^{15}$; wherein one of $Y^3$, $Y^4$, $Y^5$, and $Y^6$ is the attachment point to the rest of the molecule.

In some embodiments, $Y^1$ is $CR^{15}$; $Y^2$ is N; $Y^3$ is $CR^{15}$; $Y^4$ is $CR^{15}$; $Y^5$ is $CR^{15}$; and $Y^6$ is $CR^{15}$; wherein one of $Y^3$, $Y^4$, $Y^5$, and $Y^6$ is the attachment point to the rest of the molecule.

In some embodiments, $Y^1$ is $CR^{15}$; $Y^2$ is $CR^{15}$; $Y^3$ is N; $Y^4$ is $CR^{15}$; $Y^5$ is $CR^{15}$; and $Y^6$ is $CR^{15}$; wherein one of $Y^4$, $Y^5$, and $Y^6$ is the attachment point to the rest of the molecule.

In some embodiments, $Y^1$ is $CR^{15}$; $Y^2$ is $CR^{15}$; $Y^3$ is $CR^{15}$; $Y^4$ is N; $Y^5$ is $CR^{15}$; and $Y^6$ is $CR^{15}$; wherein one of $Y^3$, $Y^5$, and $Y^6$ is the attachment point to the rest of the molecule.

In some embodiments, $Y^1$ is $CR^{15}$; $Y^2$ is $CR^{15}$; $Y^3$ is $CR^{15}$; $Y^4$ is $CR^{15}$; $Y^5$ is N; and $Y^6$ is $CR^{15}$; wherein one of $Y^3$, $Y^4$, and $Y^6$ is the attachment point to the rest of the molecule.

In some embodiments, $Y^1$ is $CR^{15}$; $Y^2$ is $CR^{15}$; $Y^3$ is $CR^{15}$; $Y^4$ is $CR^{15}$; $Y^5$ is $CR^{15}$; and $Y^6$ is N; wherein one of $Y^3$, $Y^4$, and $Y^5$ is the attachment point to the rest of the molecule.

In some embodiments, the compound of Formula (III) is represented by Formula (IIIa-1), (IIIa-2), (IIIa-3), or (IIIa-4):

Formula (IIIa-1)

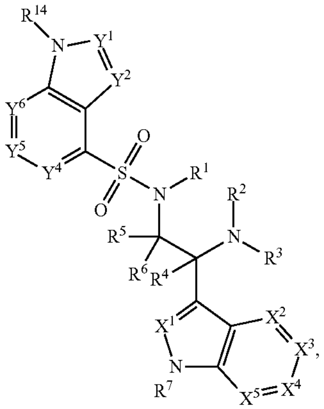

Formula (IIIa-2)

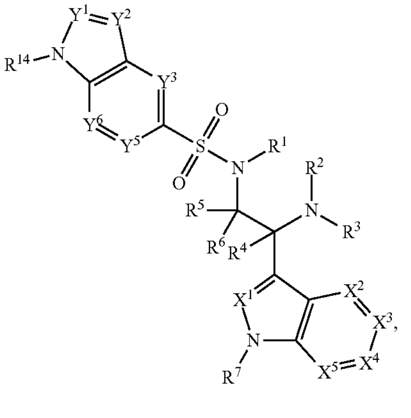

-continued

Formula (IIIa-3)

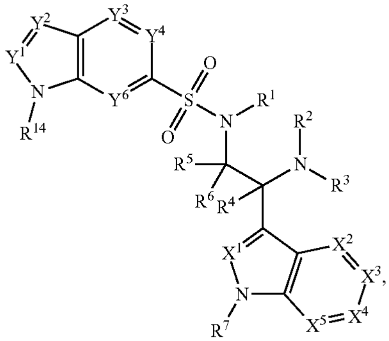

Formula (IIIa-4)

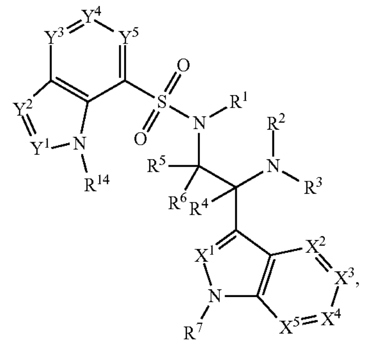

or a pharmaceutically acceptable salt thereof.

In some embodiments, the compound of Formula (III) is represented by Formula (IIIa-1). In some embodiments, the compound of Formula (III) is represented by Formula (IIIa-2). In some embodiments, the compound of Formula (III) is represented by Formula (IIIa-3). In some embodiments, the compound of Formula (III) is represented by Formula (IIIa-4).

In some embodiments, the compound of Formula (III) is represented by Formula (IIIb-1), (IIIb-2), (IIIb-3), or (IIIb-4).

Formula (IIIb-1)

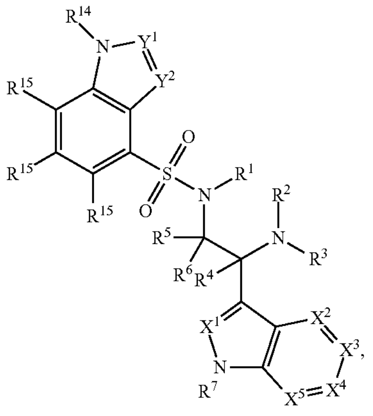

-continued

Formula (IIIb-2)

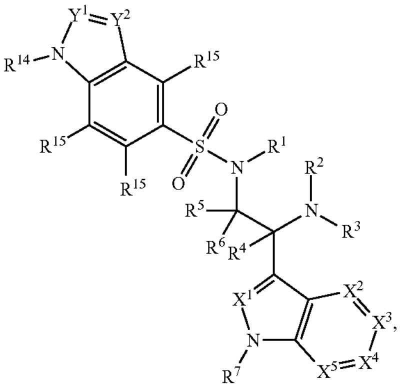

Formula (IIIb-3)

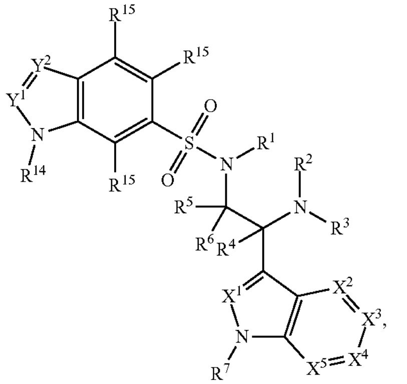

Formula (IIIb-4)

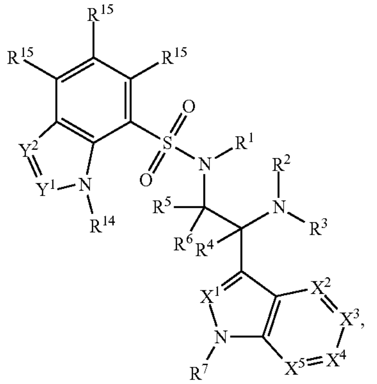

or a pharmaceutically acceptable salt thereof; wherein 0 or 1 of $Y^1$ and $Y^2$ is N.

In some embodiments, the compound of Formula (III) is represented by Formula (IIIb-1). In some embodiments, the compound of Formula (III) is represented by Formula (IIIb-2). In some embodiments, the compound of Formula (III) is represented by Formula (IIIb-3). In some embodiments, the compound of Formula (III) is represented by Formula (IIIb-4).

In some embodiments, $Y^1$ is $CR^{15}$; and $Y^2$ is $CR^{15}$. In some embodiments, $Y^1$ is N; and $Y^2$ is $CR^{15}$. In some embodiments, $Y^1$ is $CR^{15}$; and $Y^2$ is N.

In some embodiments, the compound of Formula (III) is represented by Formula (IIIc-1), (IIIc-2), (IIIc-3), or (IIIc-4):

Formula (IIIc-1)

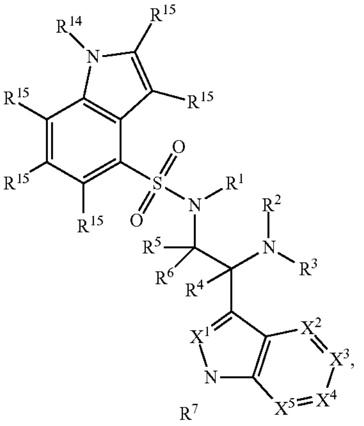

Formula (IIIc-2)

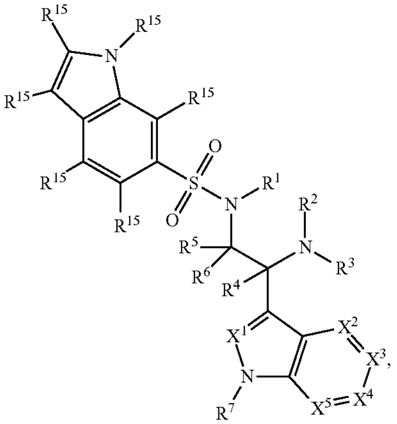

Formula (IIIc-3)

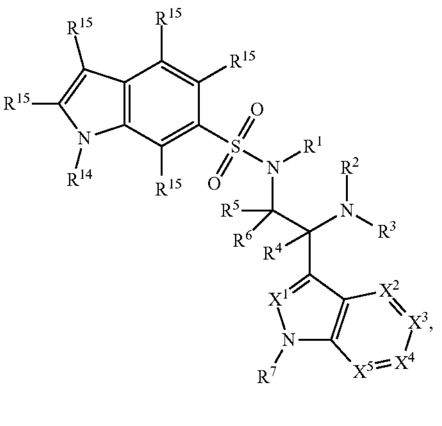

-continued

Formula (IIIc-4)

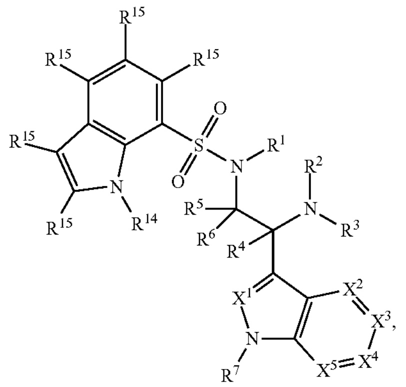

or a pharmaceutically acceptable salt thereof.

In some embodiments, the compound of Formula (III) is represented by Formula (IIIc-1). In some embodiments, the compound of Formula (III) is represented by Formula (IIIc-2). In some embodiments, the compound of Formula (III) is represented by Formula (IIIc-3). In some embodiments, the compound of Formula (III) is represented by Formula (IIIc-4).

In some embodiments, 0 or 1 of $X^1$, $X^2$, $X^3$, $X^4$, and $X^5$ are N.

In some embodiments, $X^1$ is $CR^8$; and $X^2$, $X^3$, $X^4$, and $X^5$ are independently selected from $CR^8$ and N, wherein 0, 1, or 2 of $X^2$, $X^3$, $X^4$, and $X^5$ are N. In some embodiments, $X^1$ is $CR^8$; and $X^2$, $X^3$, $X^4$, and $X^5$ are independently selected from $CR^8$ and N, wherein 0 or 1 of $X^2$, $X^3$, $X^4$, and $X^5$ are N.

In some embodiments, $X^1$ is $CR^8$; $X^2$ is $CR^8$; $X^3$ is $CR^8$; $X^4$ is $CR^8$; and $X^5$ is $CR^8$.

In some embodiments, $X^1$ is N; $X^2$ is $CR^8$; $X^3$ is $CR^8$; $X^4$ is $CR^8$; and $X^5$ is $CR^8$.

In some embodiments, $X^1$ is $CR^8$; $X^2$ is N; $X^3$ is $CR^8$; $X^4$ is $CR^8$; and $X^5$ is $CR^8$.

In some embodiments, $X^1$ is $CR^8$; $X^2$ is $CR^8$; $X^3$ is N; $X^4$ is $CR^8$; and $X^5$ is $CR^8$.

In some embodiments, $X^1$ is $CR^8$; $X^2$ is $CR^8$; $X^3$ is $CR^8$; $X^4$ is N; and $X^5$ is $CR^8$.

In some embodiments, $X^1$ is $CR^8$; $X^2$ is $CR^8$; $X^3$ is $CR^8$; $X^4$ is $CR^8$; and $X^5$ is N.

In some embodiments, $R^2$ and $R^3$ are independently selected from hydrogen; and $C_1$-$C_6$ alkyl, $C_2$-$C_6$ alkenyl, $C_2$-$C_6$ alkynyl, $C_3$-$C_6$ carbocycle, and 3- to 6-membered heterocycle, each of which is optionally substituted with one or more substituents independently selected from $R^9$. In some embodiments, $R^2$ and $R^3$ are independently selected from hydrogen; optionally substituted $C_1$-$C_6$ alkyl; and optionally substituted $C_3$-$C_6$ cycloalkyl, and optionally substituted 3- to 6-membered heterocycloalkyl, each of which is optionally substituted with one or more substituents independently selected from $R^9$. In some embodiments, $R^2$ and $R^3$ are independently selected from hydrogen; optionally substituted $C_1$-$C_6$ alkyl; and optionally substituted phenyl, and optionally substituted 5- or 6-membered heteroaryl, each of which is optionally substituted with one or more substituents independently selected from $R^9$. In some embodiments, $R^2$ and $R^3$ are independently selected from hydrogen; optionally substituted $C_1$-$C_6$ alkyl; and optionally substituted phenyl, and optionally substituted pyridinyl, each of which is optionally substituted with one or more substituents independently selected from $R^9$. In some embodiments, $R^2$ and $R^3$ are independently selected from hydrogen; and optionally substituted $C_1$-$C_6$ alkyl, each of which is optionally substituted with one or more substituents independently selected from $R^9$. In some embodiments, $R^2$ and $R^3$ are independently selected from optionally substituted $C_1$-$C_6$ alkyl, each of which is optionally substituted with one or more substituents independently selected from $R^9$.

In some embodiments, $R^2$ and $R^3$ are independently selected from hydrogen; and $C_1$-$C_6$ alkyl. In some embodiments, $R^2$ and $R^3$ are independently selected from $C_1$-$C_6$ alkyl. In some embodiments, $R^2$ and $R^3$ are independently selected from hydrogen, methyl, ethyl, n-propyl, isopropyl, n-butyl, isobutyl, sec-butyl, tert-butyl, pentyl, and hexyl. In some embodiments, $R^2$ and $R^3$ are independently selected from methyl, ethyl, n-propyl, isopropyl, n-butyl, isobutyl, sec-butyl, tert-butyl, pentyl, and hexyl. In some embodiments, $R^2$ and $R^3$ are each methyl.

In some embodiments, $R^2$ is hydrogen; and $R^3$ is selected from optionally substituted $C_1$-$C_6$ alkyl, optionally substituted $C_3$-$C_6$ cycloalkyl, and optionally substituted 3- to 6-membered heterocycloalkyl, each of which is optionally substituted with one or more substituents independently selected from $R^9$.

In some embodiments, $R^2$ and $R^3$ are each hydrogen.

In some embodiments, $R^2$ and $R^3$ are taken together with the intervening atoms to which they are attached to form a 4- to 8-membered heterocycloalkyl, which is optionally substituted with one or more substituents independently selected from $R^9$. In some embodiments, $R^2$ and $R^3$ are taken together with the intervening atoms to which they are attached to form an optionally substituted azetidinyl, optionally substituted pyrrolidinyl, optionally substituted piperidinyl, optionally substituted morpholinyl, or optionally substituted tetrahydrofuropyrrolyl, which is optionally substituted with one or more substituents independently selected from $R^9$. In some embodiments, $R^2$ and $R^3$ are taken together with the intervening atoms to which they are attached to form an optionally substituted azetidinyl, which is optionally substituted with one or more substituents independently selected from $R^9$. In some embodiments, $R^2$ and $R^3$ are taken together with the intervening atoms to which they are attached to form an optionally substituted pyrrolidinyl, which is optionally substituted with one or more substituents independently selected from $R^9$. In some embodiments, $R^2$ and $R^3$ are taken together with the intervening atoms to which they are attached to form an optionally substituted azetidinyl or an optionally substituted pyrrolidinyl, which is optionally substituted with one or more substituents independently selected from halogen, —CN, —OH, —$OR^{13}$, —$N(R^{12})_2$, $C_1$-$C_6$ alkyl, and $C_1$-$C_6$ haloalkyl. In some embodiments, $R^2$ and $R^3$ are taken together with the intervening atoms to which they are attached to form an optionally substituted azetidinyl or an optionally substituted pyrrolidinyl, which is optionally substituted with one or more substituents independently selected from —F, —Cl, —Br, —CN, —OH, —$OCH_3$, —$OCH_2CH_3$, —$OCH(CH_3)_2$, —$OCF_3$, —$NH_2$, —$NHCH_3$, —$N(CH_3)_2$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, and —$CF_3$. In some embodiments, $R^2$ and $R^3$ are taken together with the intervening atoms to which they are attached to form an optionally substituted azetidinyl or an optionally substituted pyrrolidinyl, which is optionally substituted with one or more substituents independently selected from —F, —OH, $—OCH_3$, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)CH_2CH_3$, and $—CF_3$.

In some embodiments, $R^1$ is selected from hydrogen; and $C_1$-$C_6$ alkyl, which is optionally substituted with one or more substituents independently selected from $R^9$. In some embodiments, $R^1$ is selected from hydrogen; and $C_1$-$C_6$ alkyl. In some embodiments, $R^1$ is selected from hydrogen, methyl, ethyl, n-propyl, isopropyl, n-butyl, isobutyl, sec-butyl, tert-butyl, pentyl, and hexyl. In some embodiments, $R^1$ is hydrogen or methyl. In some embodiments, $R^1$ is hydrogen. In some embodiments, $R^1$ is methyl.

In some embodiments, $R^1$ is $C_1$-$C_6$ alkyl, which is optionally substituted with one or more substituents independently selected from $R^9$. In some embodiments, $R^1$ is $C_1$-$C_6$ alkyl. In some embodiments, $R^1$ is $C_1$-$C_6$ alkyl which is substituted with 1, 2, or 3 substituents independently selected from $R^9$. In some embodiments, $R^1$ is $C_1$-$C_6$ alkyl which is substituted with 1, 2, or 3 substituents independently selected from $R^9$. In some embodiments, $R^1$ is $C_1$-$C_6$ alkyl which is substituted with 1, 2, or 3 substituents independently selected from halogen, —CN, —OH, $—OR^{13}$, $—N(R^{12})_2$, $—C(=O)R^{12}$, $—C(=O)OR^{12}$, $—OC(=O)R^{12}$, $—C(=O)N(R^{12})_2$, $—NR^{12}C(=O)R^{12}$, $—NR^{12}C(=O)N(R^{12})_2$, $—OC(=O)N(R^{12})_2$, $—NR^{12}C(=O)OR^{12}$, $—OC(=O)OR^{12}$, $—SR^{12}$, $—S(=O)R^{13}$, $—SO_2R^{13}$, $—SO_2N(R^{12})_2$, $—NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, and 3- to 6-membered heterocycle. In some embodiments, $R^1$ is $C_1$-$C_6$ alkyl which is substituted with 1, 2, or 3 substituents independently selected from halogen, —CN, —OH, $—OR^{13}$, $—N(R^{12})_2$, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ cycloalkyl, and 3- to 6-membered heterocycloalkyl. In some embodiments, $R^1$ is $C_1$-$C_6$ alkyl which is substituted with 1 or 2 substituents independently selected from halogen, —CN, —OH, $—OR^{13}$, $—N(R^{12})_2$, $C_2$-$C_4$ alkynyl, and $C_1$-$C_4$ haloalkyl. In some embodiments, $R^1$ is $C_1$-$C_6$ alkyl which is substituted with 1 or 2 substituents independently selected from —F, —Cl, —Br, —CN, —OH, $—OCH_3$, $—OCH_2CH_3$, $—OCH(CH_3)_2$, $—OCF_3$, $—NH_2$, $—NHCH_3$, $—N(CH_3)_2$, —C≡CH, $—C≡CCH_3$, $—C≡CCH_2CH_3$, $—C≡CCH(CH_3)_2$, $—CH_2F$, $—CHF_2$, and $—CF_3$. In some embodiments, $R^1$ is $C_1$-$C_6$ alkyl which is substituted with 1 or 2 substituents independently selected from —F, —CN, —OH, $—OCH_3$, $—OCH_2CH_3$, $—OCH(CH_3)_2$, $—OCF_3$, $—NH_2$, $—NHCH_3$, $—N(CH_3)_2$, —C≡CH, and $—CF_3$. In some embodiments, $R^1$ is $C_1$-$C_6$ alkyl which is substituted with 1 substituent selected from —F, —CN, $—OCH_3$, $—OCH_2CH_3$, —C≡CH, and $—CF_3$.

In some embodiments, $R^1$ and $R^2$ are taken together with the intervening atoms to which they are attached to form a 5- to 8-membered heterocycloalkyl, which is optionally substituted with one or more substituents independently selected from $R^9$. In some embodiments, $R^1$ and $R^2$ are taken together with the intervening atoms to which they are attached to form an optionally substituted 5- to 6-membered heterocycloalkyl, which is optionally substituted with one or more substituents independently selected from $R^9$.

In some embodiments, the compound of Formula (III) is represented by Formula (IIId-1), (IIId-2), (IIId-3), or (IIId-4):

Formula (IIId-1)

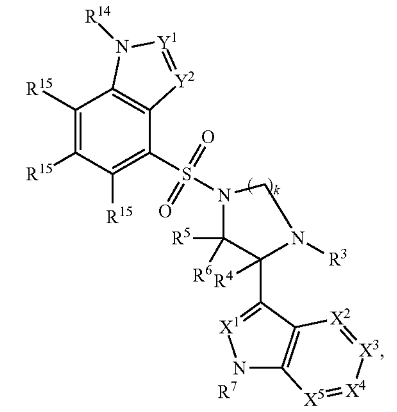

Formula (IIId-2)

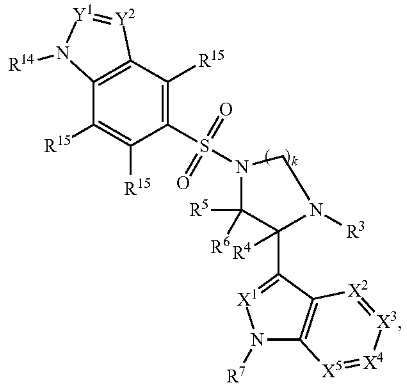

Formula (IIId-3)

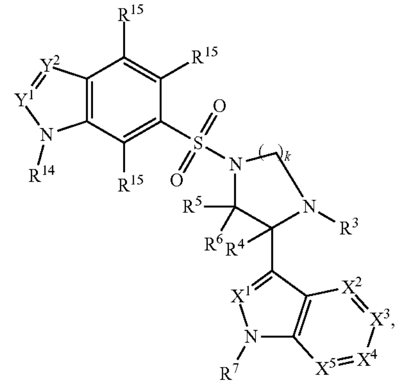

Formula (IIId-4)

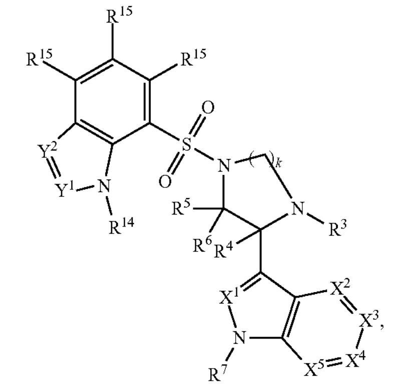

or a pharmaceutically acceptable salt thereof, wherein:

0 or 1 of $Y^1$ and $Y^2$ is N; and k is 1, 2, 3, or 4.

In some embodiments, the compound of Formula (III) is represented by Formula (IIId-1). In some embodiments, the compound of Formula (III) is represented by Formula (IIId-2). In some embodiments, the compound of Formula (III) is represented by Formula (IIId-3). In some embodiments, the compound of Formula (III) is represented by Formula (IIId-4).

In some embodiments, $Y^1$ is $CR^{15}$; and $Y^2$ is $CR^{15}$. In some embodiments, $Y^1$ is N; and $Y^2$ is $CR^{15}$. In some embodiments, $Y^1$ is $CR^{15}$; and $Y^2$ is N.

In some embodiments, k is 1, 2, or 3. In some embodiments, k is 1 or 2. In some embodiments, k is 1. In some embodiments, k is 2. In some embodiments, k is 3. In some embodiments, k is 4.

In some embodiments, $R^4$, $R^5$, and $R^6$ are each independently selected from hydrogen, halogen, —CN, —OH, —$OR^{11}$, and —$N(R^{10})_2$; and $C_1$-$C_6$ alkyl, which is optionally substituted with one or more substituents independently selected from $R^9$. In some embodiments, $R^4$, $R^5$, and $R^6$ are independently selected from hydrogen, halogen, —$OR^{11}$, and —$N(R^{10})_2$; and $C_1$-$C_6$ alkyl, which is optionally substituted with one or more substituents independently selected from $R^9$. In some embodiments, $R^4$, $R^5$, and $R^6$ are independently selected from hydrogen, —$OR^{11}$, and —$N(R^{10})_2$; and $C_1$-$C_6$ alkyl, which is optionally substituted with one or more substituents independently selected from $R^9$. In some embodiments, $R^4$, $R^5$, and $R^6$ are independently selected from hydrogen, —$OR^{11}$, and —$N(R^{10})_2$; and $C_1$-$C_6$ alkyl. In some embodiments, $R^4$, $R^5$, and $R^6$ are each hydrogen.

In some embodiments, the compound of Formula (I) or Formula (II) is represented by Formula (IV):

Formula (IV)

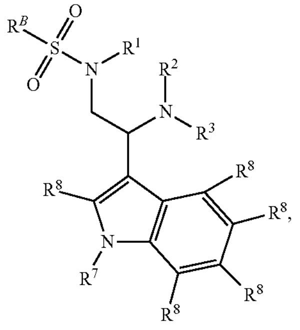

or a pharmaceutically acceptable salt thereof, wherein:

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, the compound of Formula (IV) is represented by Formula (IVa):

Formula (IVa)

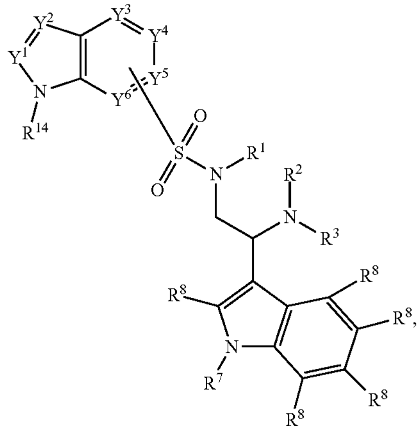

or a pharmaceutically acceptable salt thereof, wherein:

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$;

each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$;

$Y^1$, $Y^2$, $Y^3$, $Y^4$ and $Y^5$ are independently selected from $CR^1$ and N, wherein 0, 1, 2, or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl which is optionally substituted with one or more substituents independently selected from $R^9$; and $C_3$-$C_6$ cycloalkyl and 3- to 6-membered heterocycloalkyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, $Y^1$, $Y^2$, $Y^3$, $Y^4$, $Y^5$ and $Y^6$ are independently selected from $CR^{15}$ and N, wherein 0 or 1 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule.

In some embodiments, $Y^1$ is $CR^{15}$; and $Y^2$, $Y^3$, $Y^4$, $Y^5$ and $Y^6$ are independently selected from $CR^{15}$ and N, wherein 0, 1, or 2 of $Y^2$, $Y^3$, $Y^4$, $Y^5$ and $Y^6$ are N; and wherein one of $Y^2$, $Y^3$, $Y^4$, $Y^5$, and $Y^6$ is the attachment point to the rest of the molecule. In some embodiments, $Y^1$ is $CR^{15}$; and $Y^2$, $Y^3$, $Y^4$, $Y^5$ and $Y^6$ are independently selected from $CR^{15}$ and N, wherein 0 or 1 of $Y^2$, $Y^3$, $Y^4$, $Y^5$ and $Y^6$ are N; and wherein one of $Y^1$, $Y^2$, $Y^3$, $Y^4$, $Y^5$, and $Y^6$ is the attachment point to the rest of the molecule. In some embodiments, $Y^1$ is $CR^{15}$; and $Y^2$, $Y^3$, $Y^4$, $Y^5$ and $Y^6$ are independently selected from $CR^{15}$ and N, wherein 0 or 1 of $Y^2$, $Y^3$, $Y^4$, $Y^5$ and $Y^6$ are N; and wherein one of $Y^3$, $Y^4$, $Y^5$, and $Y^6$ is the attachment point to the rest of the molecule.

In some embodiments, $Y^1$ is $CR^{15}$; $Y^2$ is $CR^{15}$; $Y^3$ is $CR^{15}$; $Y^4$ is $CR^{15}$; $Y^5$ is $CR^{15}$; and $Y^6$ is $CR^{15}$; wherein one of $Y^3$, $Y^4$, $Y^5$, and $Y^6$ is the attachment point to the rest of the molecule.

In some embodiments, the compound of Formula (IV) is represented by Formula (IVb):

Formula (IVb)

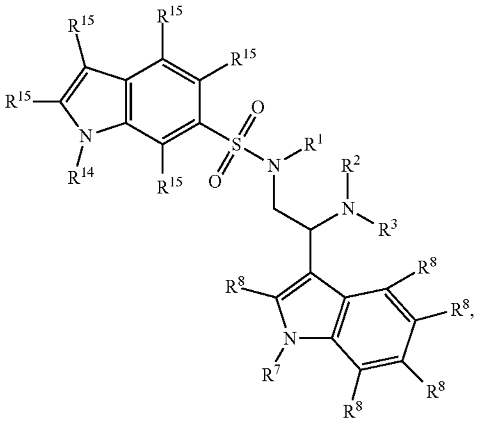

or a pharmaceutically acceptable salt thereof, wherein:

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$;

each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$;

$R^{14}$ is selected from:

hydrogen;

$C_1$-$C_6$ alkyl which is optionally substituted with one or more substituents independently selected from $R^9$; and $C_3$-$C_6$ cycloalkyl and 3- to 6-membered heterocycloalkyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, $R^7$ is selected from:

hydrogen; and $C_1$-$C_6$ alkyl, $C_2$-$C_6$ alkenyl, and $C_2$-$C_6$ alkynyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, $R^{14}$ is selected from:

hydrogen; and $C_1$-$C_6$ alkyl, $C_2$-$C_6$ alkenyl, and $C_2$-$C_6$ alkynyl, each of which is optionally substituted with one or more substituents independently selected from $R^9$; and each $R^{15}$ is independently selected from:

hydrogen, halogen, —CN, —OH, —$OR^{13}$, —$N(R^{12})_2$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$SO_2R^{13}$, and —$SO_2N(R^{12})_2$; and $C_1$-$C_6$ alkyl, optionally substituted with one or more substituents independently selected from $R^9$.

In some embodiments, $R^7$ is selected from hydrogen; and $C_1$-$C_6$ alkyl which is optionally substituted with one or more substituents independently selected from $R^9$. In some embodiments, $R^7$ is selected from hydrogen and $C_1$-$C_6$ alkyl. In some embodiments, $R^7$ is selected from hydrogen, methyl, ethyl, n-propyl, isopropyl, n-butyl, isobutyl, sec-butyl, tert-butyl, pentyl, and hexyl. In some embodiments, $R^7$ is selected from hydrogen and methyl. In some embodiments, $R^7$ is hydrogen. In some embodiments, $R^7$ is methyl.

In some embodiments, at least one $R^8$ is selected from:

halogen, —CN, —OH, —$OR^{13}$, —$N(R^{12})_2$, —C(═O)$R^{12}$, —C(═O)$OR^{12}$, —C(═O)$N(R^{12})_2$, —$NR^{12}$C(═O)$R^{12}$, —$NR^{12}$C(═O)$N(R^{12})_2$, —$SR^{12}$, —S(═O)$R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$.

In some embodiments, each $R^8$ is independently selected from hydrogen, halogen, —CN, —OH, —$OR^{13}$, —$N(R^{12})_2$, and —C(═O)$OR^{12}$; $C_1$-$C_6$ alkyl which is optionally substituted with one or more substituents independently selected from $R^9$; and 3- to 10-membered heterocycle which is optionally substituted with one or more substituents independently selected from $R^9$. In some embodiments, each $R^8$ is independently selected from hydrogen, halogen, —CN, and —$OR^{13}$; and $C_1$-$C_6$ alkyl which is optionally substituted with one or more substituents independently selected from $R^9$. In some embodiments, each $R^8$ is independently selected from hydrogen, halogen, —CN, —$OR^{13}$, $C_1$-$C_6$ alkyl, $C_1$-$C_6$ fluoroalkyl, and $C_1$-$C_6$ hydroxyalkyl. In some embodiments, each $R^8$ is independently selected from hydrogen, halogen, —CN, —$OR^{13}$, and $C_1$-$C_6$ alkyl. In some embodiments, each $R^8$ is independently selected from hydrogen, F, Cl, Br, —CN, —OMe, methyl, ethyl, n-propyl, isopropyl, n-butyl, isobutyl, sec-butyl, tert-butyl, pentyl, and hexyl, —$CF_3$, —$CHF_2$, and —$CH_2F$. In some embodiments, each $R^8$ is independently selected from hydrogen, F, Cl, Br, —CN, —OMe, methyl, ethyl, isopropyl, and —$CF_3$.

In some embodiments, each $R^{15}$ is independently selected from hydrogen, halogen, —CN, —OH, —$OR^{13}$, —$N(R^{12})_2$, —C(═O)$OR^{12}$, and —$NR^{18}SO_2R^{17}$; $C_1$-$C_6$ alkyl which is optionally substituted with one or more substituents independently selected from $R^9$; and 3- to 10-membered heterocycle which is optionally substituted with one or more substituents independently selected from $R^9$. In some embodiments, each $R^{15}$ is independently selected from hydrogen, halogen, —CN, —OH, —$OR^{13}$, —$N(R^{12})_2$, —C(═O)$OR^{12}$, and —$NR^{18}SO_2R^{17}$; and $C_1$-$C_6$ alkyl which is optionally substituted with one or more substituents independently selected from $R^9$. In some embodiments, each $R^{15}$ is independently selected from hydrogen, halogen, —CN, —OH, —$OR^{13}$, —$N(R^{12})_2$, $C_1$-$C_6$ alkyl, and $C_1$-$C_6$ fluoroalkyl. In some embodiments, each $R^{15}$ is independently selected from hydrogen, F, Cl, Br, —CN, —OH, —OMe, —$NH_2$, —NHMe, —$NMe_2$, methyl, ethyl, n-propyl, isopropyl, n-butyl, isobutyl, sec-butyl, tert-butyl, pentyl, and hexyl, —$CF_3$, —$CHF_2$, and —$CH_2F$. In some embodiments, each $R^{15}$ is independently selected from hydrogen, F, Cl, Br, —CN, —OMe, methyl, ethyl, isopropyl, and —$CF_3$.

In some embodiments, $R^{14}$ is selected from hydrogen; and $C_1$-$C_6$ alkyl which is optionally substituted with one or more substituents independently selected from $R^9$. In some embodiments, $R^{14}$ is selected from hydrogen and $C_1$-$C_6$ alkyl. In some embodiments, $R^{14}$ is selected from hydrogen; and $C_1$-$C_3$ alkyl which is optionally substituted with one or more substituents independently selected from $R^9$. In some embodiments, $R^{14}$ is selected from hydrogen and $C_1$-$C_3$ alkyl. In some embodiments, $R^{14}$ is selected from hydrogen, methyl, ethyl, n-propyl, isopropyl, n-butyl, isobutyl, sec-butyl, tert-butyl, pentyl, and hexyl. In some embodiments, $R^{14}$ is selected from hydrogen, methyl, ethyl, n-propyl, and isopropyl. In some embodiments, $R^{14}$ is selected from hydrogen and methyl. In some embodiments, $R^{14}$ is hydrogen.

In some embodiments, $R^{14}$ is methyl.

In some embodiments, each $R^9$ is independently selected from halogen, —CN, —OH, —$OR^{13}$, —$N(R^{12})_2$, —C(═O)$R^{12}$, —C(═O)$OR^{12}$, —OC(═O)$R^{12}$, —C(═O)$N(R^{12})_2$, —$NR^{12}$C(═O)$R^{12}$, $NR^{12}$C(═O)$N(R^{12})_2$, —OC(═O)$N(R^{12})_2$, —$NR^{12}$C(═O)$OR^{12}$, —OC(═O)$OR^{12}$, —$SR^{12}$, —S(═O)$R^{13}$, —$SO_2R^{13}$, —$SO_2N(R^{12})_2$, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, and 3- to 6-membered heterocycle. In some embodiments, each $R^9$ is independently selected from halogen, —CN, —OH, —$OR^{13}$, —$N(R^{12})_2$, —C(═O)$OR^{12}$, —OC(═O)$R^{12}$, —C(═O)$N(R^{12})_2$, —$NR^{12}$C(═O)$R^{12}$, $C_1$-$C_6$ alkyl, $C_1$-$C_6$ haloalkyl, $C_1$-$C_6$ hydroxyalkyl, $C_1$-$C_6$ aminoalkyl, $C_3$-$C_6$ cycloalkyl, and 3- to 6-membered heterocycloalkyl. In some embodiments, each $R^9$ is independently selected from halogen, —CN, —OH, —$OR^{13}$, —$N(R^{12})_2$, $C_1$-$C_6$ alkyl, $C_1$-$C_6$ haloalkyl, $C_1$-$C_6$ hydroxyalkyl, $C_1$-$C_6$ aminoalkyl, $C_3$-$C_6$ cycloalkyl, and 3- to 6-membered heterocycloalkyl. In some embodiments, each $R^9$ is independently selected from halogen, —CN, —OH, —$OR^{13}$, —$N(R^{12})_2$, $C_1$-$C_6$ alkyl, and $C_1$-$C_6$ haloalkyl. In some embodiments, each $R^9$ is independently selected from —F, —Cl, —Br, —CN, —OH, —$OCH_3$, —$OCH_2CH_3$, —$OCH(CH_3)_2$, —$OCF_3$, —$NH_2$, —$NHCH_3$, —$N(CH_3)_2$, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, and —$CF_3$.

In some embodiments, each $R^{10}$ is independently selected from hydrogen; and $C_1$-$C_6$ alkyl, $C_3$-$C_6$ cycloalkyl, 3- to 6-membered heterocycloalkyl, phenyl, and monocyclic heteroaryl, each of which is optionally substituted with one or more substituents independently selected from $R^9$. In some embodiments, each $R^{10}$ is independently selected from hydrogen; and $C_1$-$C_6$ alkyl, $C_3$-$C_6$ cycloalkyl, and 3- to 6-membered heterocycloalkyl, each of which is optionally substituted with one or more substituents independently selected from $R^9$. In some embodiments, each $R^{10}$ is independently selected from hydrogen, $C_1$-$C_6$ alkyl, $C_1$-$C_6$ haloalkyl, $C_3$-$C_6$ cycloalkyl, 3- to 6-membered heterocycloalkyl, phenyl, and monocyclic heteroaryl. In some embodiments, each $R^{10}$ is independently selected from hydrogen, $C_1$-$C_6$ alkyl, $C_1$-$C_6$ haloalkyl, $C_3$-$C_6$ cycloalkyl, and 3- to 6-membered heterocycloalkyl. In some embodiments, each $R^{10}$ is independently selected from hydrogen, $C_1$-$C_6$ alkyl, and $C_1$-$C_6$ haloalkyl. In some embodiments, each $R^{10}$ is independently selected from hydrogen, —F, —Cl, —Br, —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$CH_2F$, —$CHF_2$, and —$CF_3$.

In some embodiments, each $R^{11}$ is independently selected from $C_1$-$C_6$ alkyl, $C_3$-$C_6$ cycloalkyl, 3- to 6-membered heterocycloalkyl, phenyl, and monocyclic heteroaryl, each of which is optionally substituted with one or more substituents independently selected from $R^9$. In some embodiments, each $R^{11}$ is independently selected from $C_1$-$C_6$ alkyl, $C_3$-$C_6$ cycloalkyl, and 3- to 6-membered heterocycloalkyl, each of which is optionally substituted with one or more substituents independently selected from $R^9$. In some embodiments, each $R^{11}$ is independently selected from $C_1$-$C_6$ alkyl, $C_1$-$C_6$ haloalkyl, $C_3$-$C_6$ cycloalkyl, 3- to 6-membered heterocycloalkyl, phenyl, and monocyclic heteroaryl. In some embodiments, each $R^{11}$ is independently selected from $C_1$-$C_6$ alkyl, $C_1$-$C_6$ haloalkyl, $C_3$-$C_6$ cycloalkyl, and 3- to 6-membered heterocycloalkyl. In some embodiments, each $R^{11}$ is independently selected from $C_1$-$C_6$ alkyl, and $C_1$-$C_6$ haloalkyl. In some embodiments, each $R^{11}$ is independently selected from —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)CH_2CH_3$, $—C(CH_3)_3$, $—CH_2F$, $—CHF_2$, and $—CF_3$.

In some embodiments, each $R^{12}$ is independently selected from hydrogen, $C_1$-$C_6$ alkyl, $C_1$-$C_6$ haloalkyl, $C_3$-$C_6$ cycloalkyl, 3- to 6-membered heterocycloalkyl, phenyl, and monocyclic heteroaryl. In some embodiments, each $R^{12}$ is independently selected from hydrogen, $C_1$-$C_6$ alkyl, $C_1$-$C_6$ haloalkyl, $C_3$-$C_6$ cycloalkyl, and 3- to 6-membered heterocycloalkyl. In some embodiments, each $R^{12}$ is independently selected from hydrogen, $C_1$-$C_6$ alkyl, and $C_1$-$C_6$ haloalkyl. In some embodiments, each $R^{12}$ is independently selected from hydrogen, —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)CH_2CH_3$, $—C(CH_3)_3$, $—CH_2F$, $—CHF_2$, and $—CF_3$.

In some embodiments, each $R^{13}$ is independently selected from $C_1$-$C_6$ alkyl, $C_1$-$C_6$ haloalkyl, $C_3$-$C_6$ cycloalkyl, 3- to 6-membered heterocycloalkyl, phenyl, and monocyclic heteroaryl. In some embodiments, each $R^{13}$ is independently selected from $C_1$-$C_6$ alkyl, $C_1$-$C_6$ haloalkyl, $C_3$-$C_6$ cycloalkyl, and 3- to 6-membered heterocycloalkyl. In some embodiments, each $R^{13}$ is independently selected from $C_1$-$C_6$ alkyl, and $C_1$-$C_6$ haloalkyl. In some embodiments, each $R^{13}$ is independently selected from —F, —Cl, —Br, $—CH_3$, $—CH_2CH_3$, $—CH_2CH_2CH_3$, $—CH(CH_3)_2$, $—CH_2CH_2CH_2CH_3$, $—CH_2CH(CH_3)_2$, $—CH(CH_3)CH_2CH_3$, $—C(CH_3)_3$, $—CH_2F$, $—CHF_2$, and $—CF_3$.

Any combination of the groups described above for the various variables is contemplated herein. Throughout the specification, groups and substituents thereof are chosen by one skilled in the field to provide stable moieties and compounds.

In some embodiments the compound or salt described herein is a compound described in Table 1, or a pharmaceutically acceptable salt thereof.

TABLE 1

| Cmpd No. | Structure | Name |
|---|---|---|
| 1 | 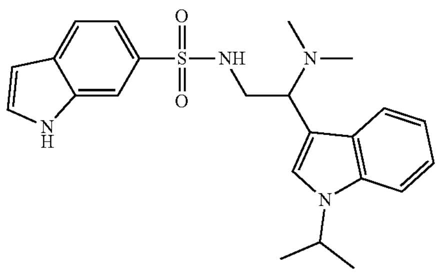 [SMILES: CC(C)n1cc(C(CNS(=O)(=O)c2ccc3cc[nH]c3c2)N(C)C)c2ccccc21] | N-(2-(dimethylamino)-2-(1-isopropyl-1H-indol-3-yl)ethyl)-1H-indole-6-sulfonamide |
| 2 | 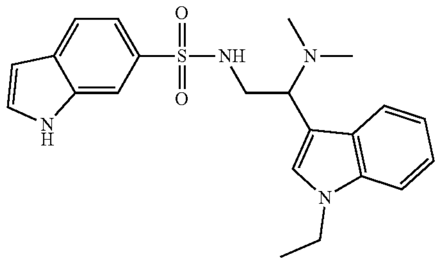 [SMILES: CCn1cc(C(CNS(=O)(=O)c2ccc3cc[nH]c3c2)N(C)C)c2ccccc21] | N-(2-(dimethylamino)-2-(1-ethyl-1H-indol-3-yl)ethyl)-1H-indole-6-sulfonamide |
| 3 | 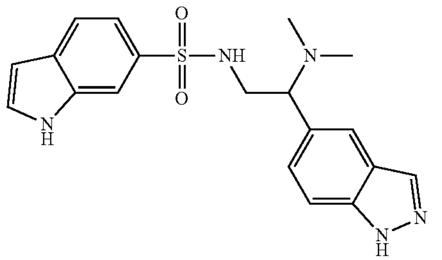 [SMILES: CN(C)C(CNS(=O)(=O)c1ccc2cc[nH]c2c1)c1ccc2[nH]ncc2c1] | N-(2-(dimethylamino)-2-(1H-indazol-5-yl)ethyl)-1H-indole-6-sulfonamide |
| 4 | 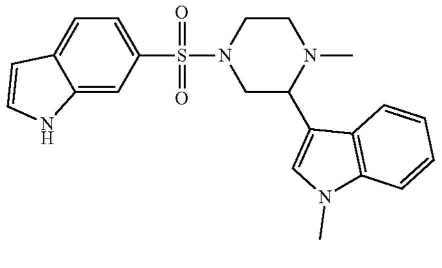 [SMILES: CN1CCN(S(=O)(=O)c2ccc3cc[nH]c3c2)CC1c1cn(C)c2ccccc12] | 3-(4-((1H-indol-6-yl)sulfonyl)-1-methylpiperazin-2-yl)-1-methyl-1H-indole |

TABLE 1-continued

| Cmpd No. | Structure | Name |
|---|---|---|
| 5 | 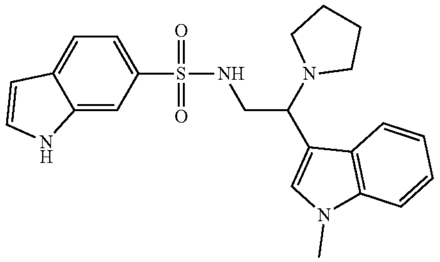 [SMILES: Cn1cc(C(CNS(=O)(=O)c2ccc3cc[nH]c3c2)N2CCCC2)c2ccccc21] | N-(2-(1-methyl-1H-indol-3-yl)-2-(pyrrolidin-1-yl)ethyl)-1H-indole-6-sulfonamide |
| 6 | 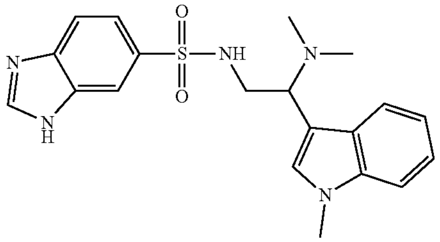 [SMILES: CN(C)C(CNS(=O)(=O)c1ccc2nc[nH]c2c1)c1cn(C)c2ccccc12] | N-(2-(dimethylamino)-2-(1-methyl-1H-indol-3-yl)ethyl)-1H-benzo[d]imidazole-6-sulfonamide |
| 7 | 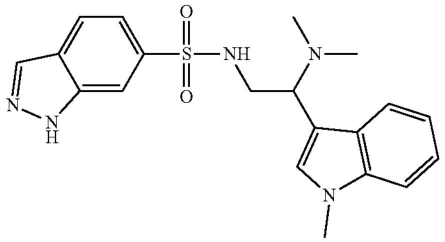 [SMILES: CN(C)C(CNS(=O)(=O)c1ccc2cn[nH]c2c1)c1cn(C)c2ccccc12] | N-(2-(dimethylamino)-2-(1-methyl-1H-indol-3-yl)ethyl)-1H-indazole-6-sulfonamide |
| 8 | 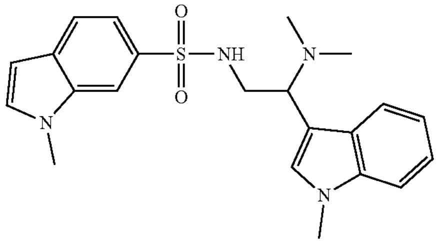 [SMILES: CN(C)C(CNS(=O)(=O)c1ccc2ccn(C)c2c1)c1cn(C)c2ccccc12] | N-(2-(dimethylamino)-2-(1-methyl-1H-indol-3-yl)ethyl)-1-methyl-1H-indole-6-sulfonamide |
| 10 | 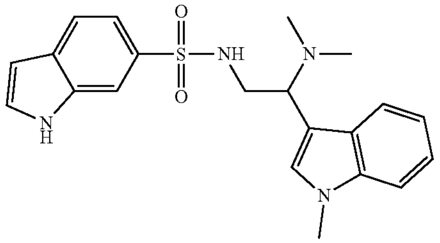 [SMILES: CN(C)C(CNS(=O)(=O)c1ccc2cc[nH]c2c1)c1cn(C)c2ccccc12] | N-(2-(dimethylamino)-2-(1-methyl-1H-indol-3-yl)ethyl)-1H-indole-6-sulfonamide |
| 11 | 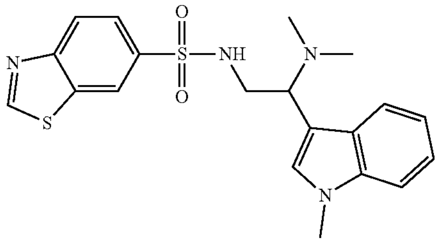 [SMILES: CN(C)C(CNS(=O)(=O)c1ccc2ncsc2c1)c1cn(C)c2ccccc12] | N-(2-(dimethylamino)-2-(1-methyl-1H-indol-3-yl)ethyl)benzo[d]thiazole-6-sulfonamide |

TABLE 1-continued
| Cmpd No. | Structure | Name |
|---|---|---|
| 12 | 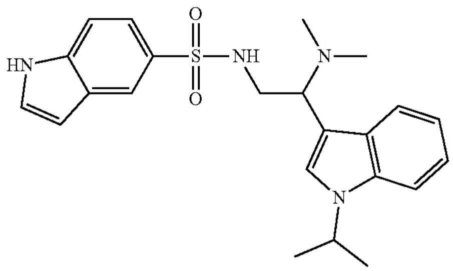 [SMILES: CC(C)n1cc(C(CNS(=O)(=O)c2ccc3[nH]ccc3c2)N(C)C)c2ccccc21] | N-(2-(dimethylamino)-2-(1-isopropyl-1H-indol-3-yl)ethyl)-1H-indole-5-sulfonamide |
| 13 | 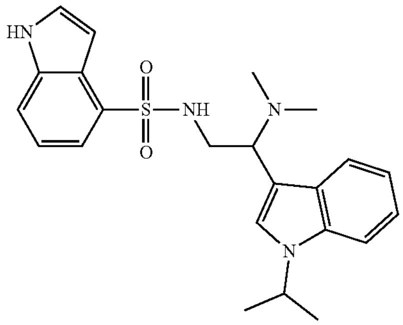 [SMILES: CC(C)n1cc(C(CNS(=O)(=O)c2cccc3[nH]ccc23)N(C)C)c2ccccc21] | N-(2-(dimethylamino)-2-(1-isopropyl-1H-indol-3-yl)ethyl)-1H-indole-4-sulfonamide |
| 14 | 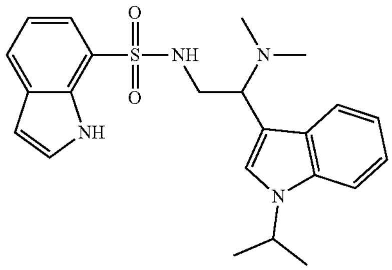 [SMILES: CC(C)n1cc(C(CNS(=O)(=O)c2cccc3cc[nH]c23)N(C)C)c2ccccc21] | N-(2-(dimethylamino)-2-(1-isopropyl-1H-indol-3-yl)ethyl)-1H-indole-7-sulfonamide |
| 15 | 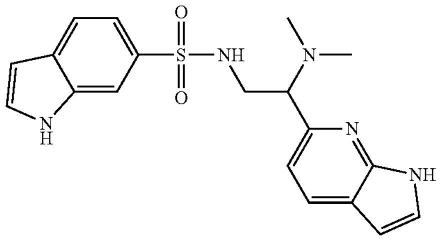 [SMILES: CN(C)C(CNS(=O)(=O)c1ccc2cc[nH]c2c1)c1ccc2cc[nH]c2n1] | N-(2-(dimethylamino)-2-(1H-pyrrolo[2,3-b]pyridin-6-yl)ethyl)-1H-indole-6-sulfonamide |
| 17 | 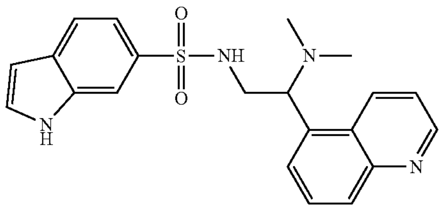 [SMILES: CN(C)C(CNS(=O)(=O)c1ccc2cc[nH]c2c1)c1cccc2ncccc12] | N-(2-(dimethylamino)-2-(quinolin-5-yl)ethyl)-1H-indole-6-sulfonamide |

TABLE 1-continued
| Cmpd No. | Structure | Name |
|---|---|---|
| 18 | 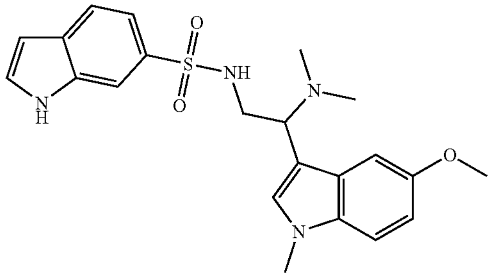 [SMILES: COc1ccc2c(c1)c(C(CNS(=O)(=O)c1ccc3cc[nH]c3c1)N(C)C)cn2C] | N-(2-(dimethylamino)-2-(5-methoxy-1-methyl-1H-indol-3-yl)ethyl)-1H-indole-6-sulfonamide |
| 19 | 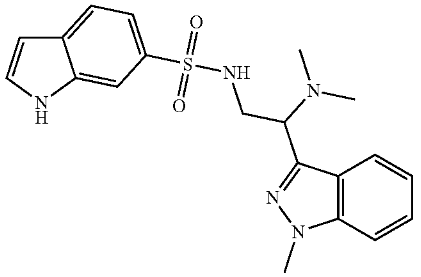 [SMILES: CN(C)C(CNS(=O)(=O)c1ccc2cc[nH]c2c1)c1nn(C)c2ccccc12] | N-(2-(dimethylamino)-2-(1-methyl-1H-indazol-3-yl)ethyl)-1H-indole-6-sulfonamide |
| 20 | 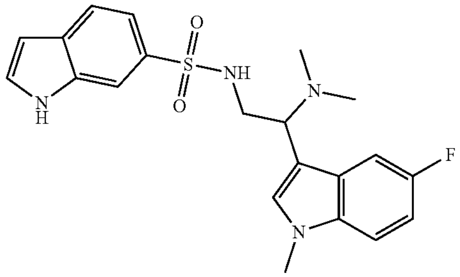 [SMILES: CN(C)C(CNS(=O)(=O)c1ccc2cc[nH]c2c1)c1cn(C)c2ccc(F)cc12] | N-(2-(dimethylamino)-2-(5-fluoro-1-methyl-1H-indol-3-yl)ethyl)-1H-indole-6-sulfonamide |
| 21 | 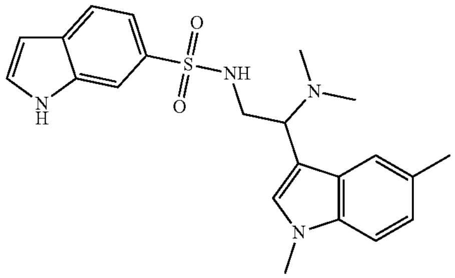 [SMILES: Cc1ccc2c(c1)c(C(CNS(=O)(=O)c1ccc3cc[nH]c3c1)N(C)C)cn2C] | N-(2-(1,5-dimethyl-1H-indol-3-yl)-2-(dimethylamino)ethyl)-1H-indole-6-sulfonamide |
| 22 | 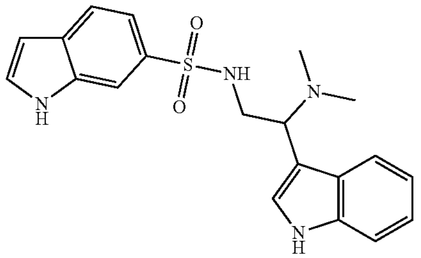 [SMILES: CN(C)C(CNS(=O)(=O)c1ccc2cc[nH]c2c1)c1c[nH]c2ccccc12] | N-(2-(dimethylamino)-2-(1H-indol-3-yl)ethyl)-1H-indole-6-sulfonamide |

TABLE 1-continued
| Cmpd No. | Structure | Name |
|---|---|---|
| 23 | 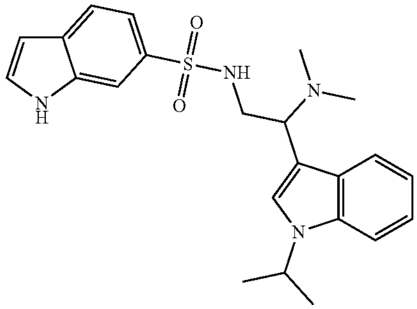 [SMILES: CC(C)n1cc(C(CNS(=O)(=O)c2ccc3cc[nH]c3c2)N(C)C)c2ccccc21] | N-(2-(dimethylamino)-2-(1-isopropyl-1H-indol-3-yl)ethyl)-1H-indole-6-sulfonamide |
| 24 | 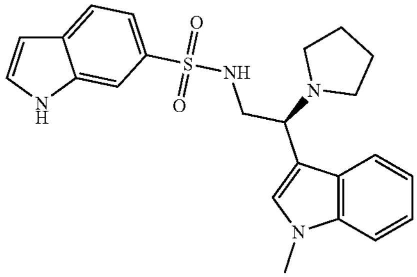 [SMILES: Cn1cc([C@@H](CNS(=O)(=O)c2ccc3cc[nH]c3c2)N2CCCC2)c2ccccc21] | (S)-N-(2-(1-methyl-1H-indol-3-yl)-2-(pyrrolidin-1-yl)ethyl)-1H-indole-6-sulfonamide |
| 25 | 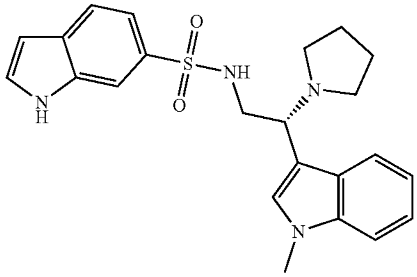 [SMILES: Cn1cc([C@H](CNS(=O)(=O)c2ccc3cc[nH]c3c2)N2CCCC2)c2ccccc21] | (R)-N-(2-(1-methyl-1H-indol-3-yl)-2-(pyrrolidin-1-yl)ethyl)-1H-indole-6-sulfonamide |
| 26 | 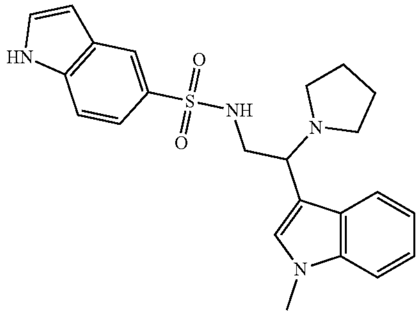 [SMILES: Cn1cc(C(CNS(=O)(=O)c2ccc3[nH]ccc3c2)N2CCCC2)c2ccccc21] | N-(2-(1-methyl-1H-indol-3-yl)-2-(pyrrolidin-1-yl)ethyl)-1H-indole-5-sulfonamide |
| 27 | 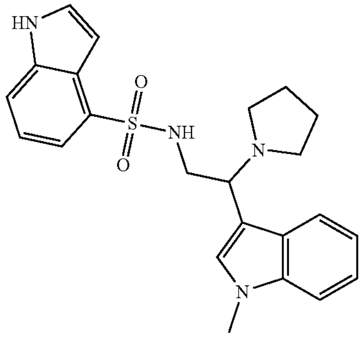 [SMILES: Cn1cc(C(CNS(=O)(=O)c2cccc3[nH]ccc23)N2CCCC2)c2ccccc21] | N-(2-(1-methyl-1H-indol-3-yl)-2-(pyrrolidin-1-yl)ethyl)-1H-indole-4-sulfonamide |

TABLE 1-continued

| Cmpd No. | Structure | Name |
|---|---|---|
| 28 | 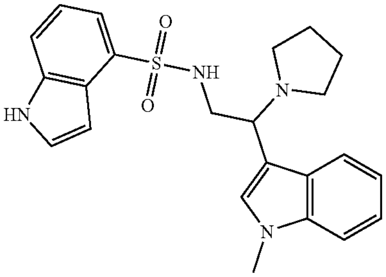 [SMILES: Cn1cc(C(CNS(=O)(=O)c2cccc3[nH]ccc23)N2CCCC2)c2ccccc21] | N-(2-(1-methyl-1H-indol-3-yl)-2-(pyrrolidin-1-yl)ethyl)-1H-indole-4-sulfonamide |
| 29 | 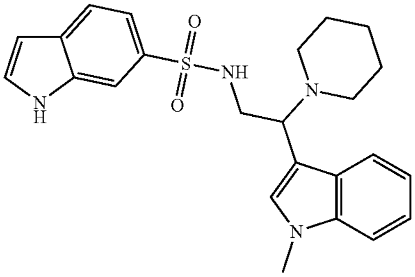 [SMILES: Cn1cc(C(CNS(=O)(=O)c2ccc3cc[nH]c3c2)N2CCCCC2)c2ccccc21] | N-(2-(1-methyl-1H-indol-3-yl)-2-(piperidin-1-yl)ethyl)-1H-indole-6-sulfonamide |
| 30 | 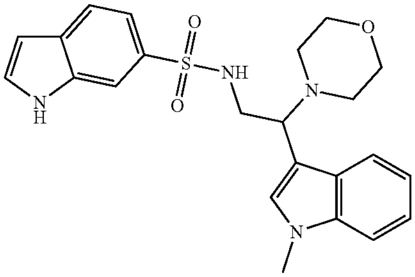 [SMILES: Cn1cc(C(CNS(=O)(=O)c2ccc3cc[nH]c3c2)N2CCOCC2)c2ccccc21] | N-(2-(1-methyl-1H-indol-3-yl)-2-morpholinoethyl)-1H-indole-6-sulfonamide |
| 31 | 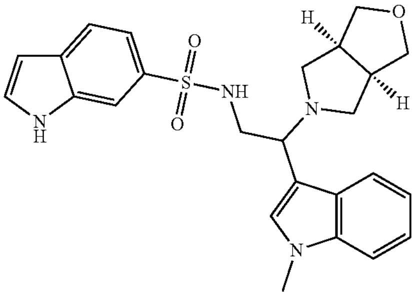 [SMILES: Cn1cc(C(CNS(=O)(=O)c2ccc3cc[nH]c3c2)N2C[C@H]3COC[C@H]3C2)c2ccccc21] | N-(2-(1-methyl-1H-indol-3-yl)-2-(trans-tetrahydro-1H-furo[3,4-c]pyrrol-5(3H)-yl)ethyl)-1H-indole-6-sulfonamide |
| 32 | 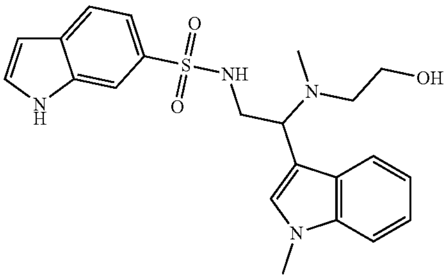 [SMILES: CN(CCO)C(CNS(=O)(=O)c1ccc2cc[nH]c2c1)c1cn(C)c2ccccc12] | N-(2-((2-hydroxyethyl)(methyl)amino)-2-(1-methyl-1H-indol-3-yl)ethyl)-1H-indole-6-sulfonamide |

TABLE 1-continued

| Cmpd No. | Structure | Name |
|---|---|---|
| 33 | 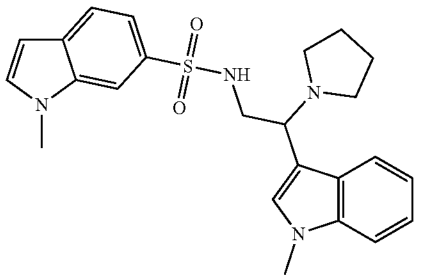 [SMILES: Cn1ccc2ccc(S(=O)(=O)NCC(c3cn(C)c4ccccc34)N3CCCC3)cc21] | 1-methyl-N-(2-(1-methyl-1H-indol-3-yl)-2-(pyrrolidin-1-yl)ethyl)-1H-indole-6-sulfonamide |
| 35 | 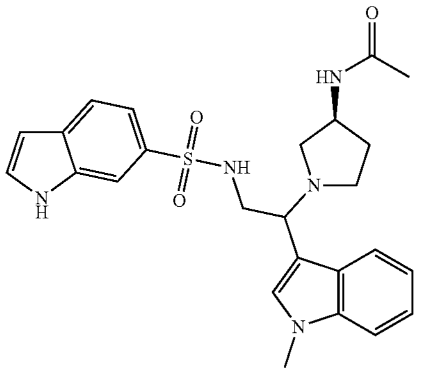 [SMILES: CC(=O)N[C@H]1CCN(C(CNS(=O)(=O)c2ccc3cc[nH]c3c2)c2cn(C)c3ccccc23)C1] | N-((3S)-1-(2-(1H-indole-6-sulfonamido)-1-(1-methyl-1H-indol-3-yl)ethyl)pyrrolidin-3-yl)acetamide |
| 36 | 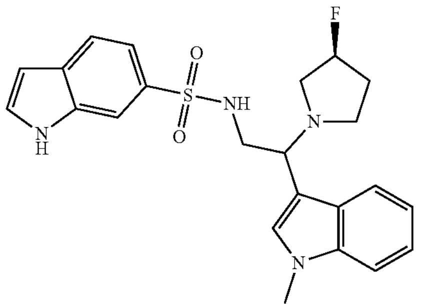 [SMILES: Cn1cc(C(CNS(=O)(=O)c2ccc3cc[nH]c3c2)N2CC[C@H](F)C2)c2ccccc21] | N-(2-((S)-3-fluoropyrrolidin-1-yl)-2-(1-methyl-1H-indol-3-yl)ethyl)-1H-indole-6-sulfonamide |
| 37 | 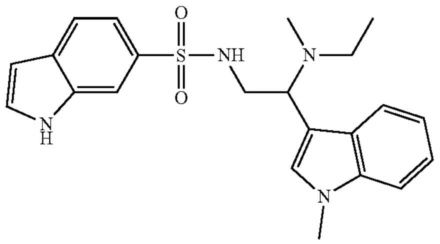 | N-(2-(ethyl(methyl)amino)-2-(1-methyl-1H-indol-3-yl)ethyl)-1H-indole-6-sulfonamide |
| 38 | 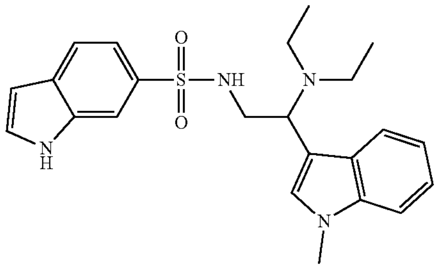 [SMILES: CCN(CC)C(CNS(=O)(=O)c1ccc2cc[nH]c2c1)c1cn(C)c2ccccc12] | N-(2-(diethylamino)-2-(1-methyl-1H-indol-3-yl)ethyl)-1H-indole-6-sulfonamide |

TABLE 1-continued

| Cmpd No. | Structure | Name |
|---|---|---|
| 39 | 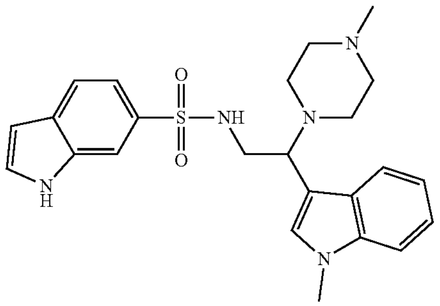 [SMILES: CN1CCN(C(CNS(=O)(=O)c2ccc3cc[nH]c3c2)c2cn(C)c3ccccc23)CC1] | N-(2-(1-methyl-1H-indol-3-yl)-2-(4-methylpiperazin-1-yl)ethyl)-1H-indole-6-sulfonamide |
| 40 | 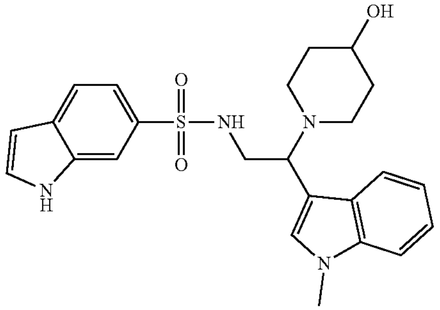 [SMILES: Cn1cc(C(CNS(=O)(=O)c2ccc3cc[nH]c3c2)N2CCC(O)CC2)c2ccccc21] | N-(2-(4-hydroxypiperidin-1-yl)-2-(1-methyl-1H-indol-3-yl)ethyl)-1H-indole-6-sulfonamide |
| 42 | 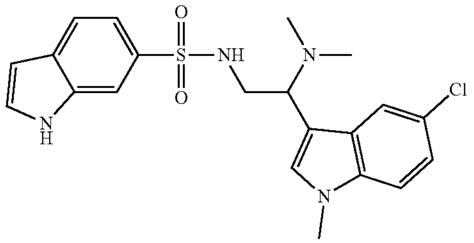 [SMILES: CN(C)C(CNS(=O)(=O)c1ccc2cc[nH]c2c1)c1cn(C)c2ccc(Cl)cc12] | N-(2-(5-chloro-1-methyl-1H-indol-3-yl)-2-(dimethylamino)ethyl)-1H-indole-6-sulfonamide |
| 43 | 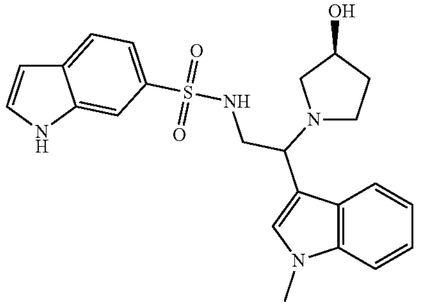 [SMILES: Cn1cc(C(CNS(=O)(=O)c2ccc3cc[nH]c3c2)N2CC[C@H](O)C2)c2ccccc21] | N-(2-((S)-3-hydroxypyrrolidin-1-yl)-2-(1-methyl-1H-indol-3-yl)ethyl)-1H-indole-6-sulfonamide |
| 44 | 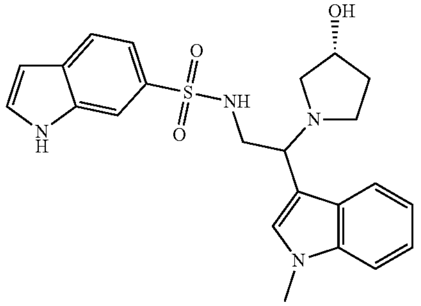 [SMILES: Cn1cc(C(CNS(=O)(=O)c2ccc3cc[nH]c3c2)N2CC[C@@H](O)C2)c2ccccc21] | N-(2-((R)-3-hydroxypyrrolidin-1-yl)-2-(1-methyl-1H-indol-3-yl)ethyl)-1H-indole-6-sulfonamide |

TABLE 1-continued

| Cmpd No. | Structure | Name |
|---|---|---|
| 45 | 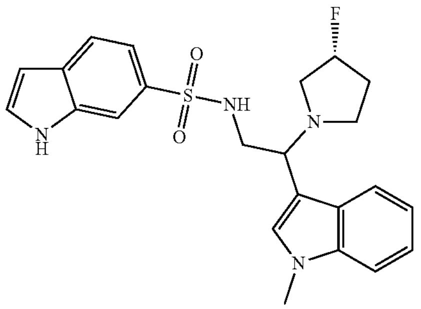 [SMILES: Cn1cc(C(CNS(=O)(=O)c2ccc3cc[nH]c3c2)N2CC[C@@H](F)C2)c2ccccc21] | N-(2-((R)-3-fluoropyrrolidin-1-yl)-2-(1-methyl-1H-indol-3-yl)ethyl)-1H-indole-6-sulfonamide |
| 46 | 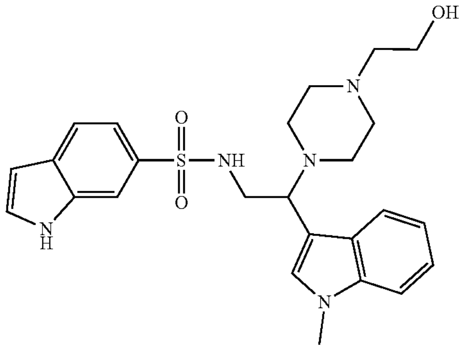 [SMILES: Cn1cc(C(CNS(=O)(=O)c2ccc3cc[nH]c3c2)N2CCN(CCO)CC2)c2ccccc21] | N-(2-(4-(2-hydroxyethyl)piperazin-1-yl)-2-(1-methyl-1H-indol-3-yl)ethyl)-1H-indole-6-sulfonamide |
| 47 | 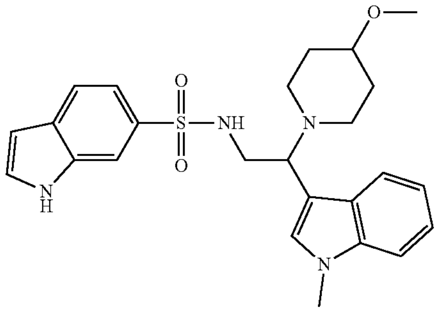 [SMILES: COC1CCN(C(CNS(=O)(=O)c2ccc3cc[nH]c3c2)c2cn(C)c3ccccc23)CC1] | N-(2-(4-methoxypiperidin-1-yl)-2-(1-methyl-1H-indol-3-yl)ethyl)-1H-indole-6-sulfonamide |
| 48 | 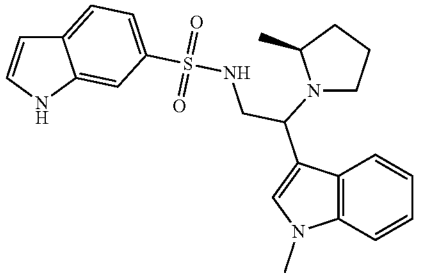 [SMILES: C[C@H]1CCCN1C(CNS(=O)(=O)c1ccc2cc[nH]c2c1)c1cn(C)c2ccccc12] | N-(2-(1-methyl-1H-indol-3-yl)-2-((S)-2-methylpyrrolidin-1-ylethyl)-1H-indole-6-sulfonamide |
| 49 | 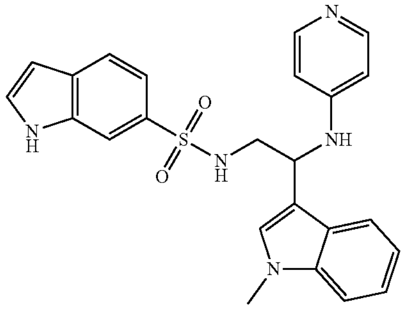 [SMILES: Cn1cc(C(CNS(=O)(=O)c2ccc3cc[nH]c3c2)Nc2ccncc2)c2ccccc21] | N-(2-(1-methyl-1H-indol-3-yl)-2-(pyridin-4-ylamino)ethyl)-1H-indole-6-sulfonamide |

TABLE 1-continued

| Cmpd No. | Structure | Name |
| --- | --- | --- |
| 50 | 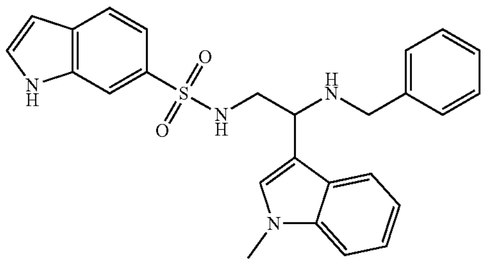 [SMILES: Cn1cc(C(CNS(=O)(=O)c2ccc3cc[nH]c3c2)NCc2ccccc2)c2ccccc21] | N-(2-(benzylamino)-2-(1-methyl-1H-indol-3-yl)ethyl)-1H-indole-6-sulfonamide |
| 51 | 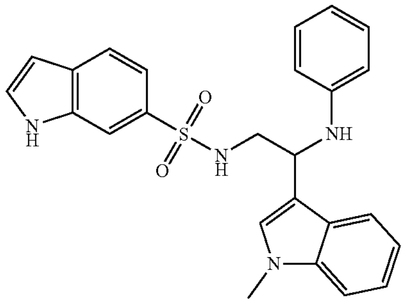 [SMILES: Cn1cc(C(CNS(=O)(=O)c2ccc3cc[nH]c3c2)Nc2ccccc2)c2ccccc21] | N-(2-(1-methyl-1H-indol-3-yl)-2-(phenylamino)ethyl)-1H-indole-6-sulfonamide |
| 52 | 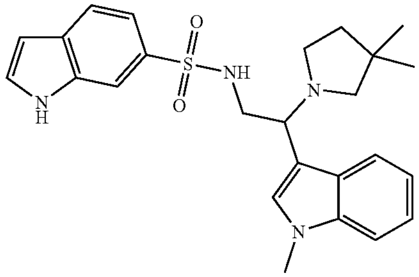 [SMILES: Cn1cc(C(CNS(=O)(=O)c2ccc3cc[nH]c3c2)N2CCC(C)(C)C2)c2ccccc21] | N-(2-(3,3-dimethylpyrrolidin-1-yl)-2-(1-methyl-1H-indol-3-yl)ethyl)-1H-indole-6-sulfonamide |
| 53 | 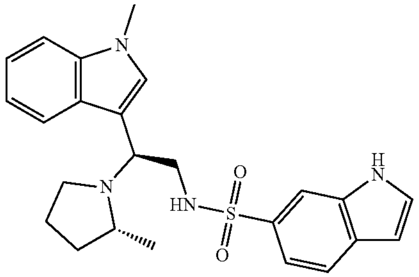 [SMILES: C[C@@H]1CCCN1[C@H](CNS(=O)(=O)c1ccc2cc[nH]c2c1)c1cn(C)c2ccccc12] | N-((S)-2-(1-methyl-1H-indol-3-yl)-2-((R)-2-methylpyrrolidin-1-yl)ethyl)-1H-indole-6-sulfonamide |
| 54 | 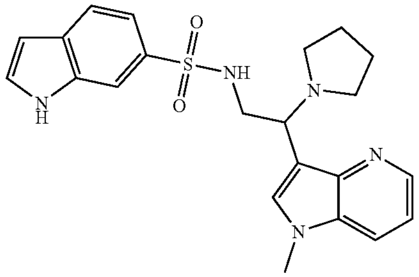 [SMILES: Cn1cc(C(CNS(=O)(=O)c2ccc3cc[nH]c3c2)N2CCCC2)c2ncccc21] | N-(2-(1-methyl-1H-pyrrolo[3,2-b]pyridin-3-yl)-2-(pyrrolidin-1-yl)ethyl)-1H-indole-6-sulfonamide |

TABLE 1-continued

| Cmpd No. | Structure | Name |
|---|---|---|
| 55 | 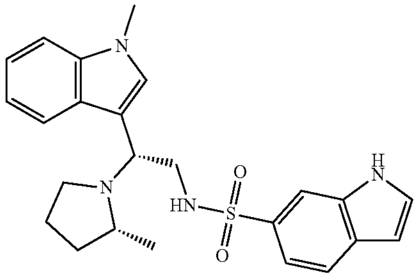 [SMILES: C[C@@H]1CCCN1[C@@H](CNS(=O)(=O)c1ccc2cc[nH]c2c1)c1cn(C)c2ccccc12] | N-((R)-2-(1-methyl-1H-indol-3-yl)-2-((R)-2-methylpyrrolidin-1-yl)ethyl)-1H-indole-6-sulfonamide |
| 57 | 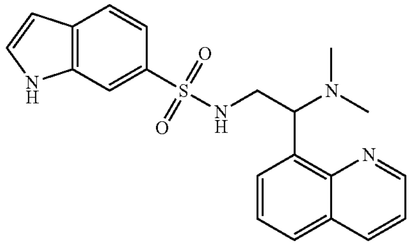 [SMILES: CN(C)C(CNS(=O)(=O)c1ccc2cc[nH]c2c1)c1cccc2cccnc12] | N-(2-(dimethylamino)-2-(quinolin-8-yl)ethyl)-1H-indole-6-sulfonamide |
| 58 | 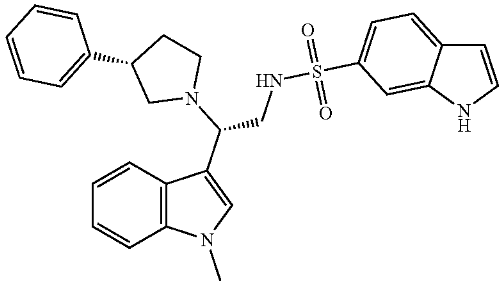 [SMILES: Cn1cc([C@@H](CNS(=O)(=O)c2ccc3cc[nH]c3c2)N2CC[C@@H](c3ccccc3)C2)c2ccccc21] | N-((S)-2-(1-methyl-1H-indol-3-yl)-2-((S)-3-phenylpyrrolidin-1-yl)ethyl)-1H-indole-6-sulfonamide |
| 59 | 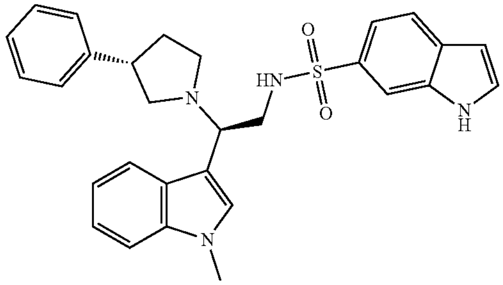 [SMILES: Cn1cc([C@H](CNS(=O)(=O)c2ccc3cc[nH]c3c2)N2CC[C@@H](c3ccccc3)C2)c2ccccc21] | N-((R)-2-(1-methyl-1H-indol-3-yl)-2-((S)-3-phenylpyrrolidin-1-yl)ethyl)-1H-indole-6-sulfonamide |
| 60 | 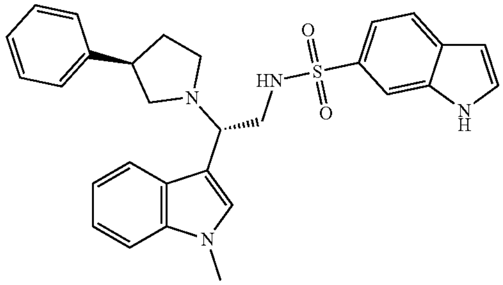 [SMILES: Cn1cc([C@@H](CNS(=O)(=O)c2ccc3cc[nH]c3c2)N2CC[C@H](c3ccccc3)C2)c2ccccc21] | N-((S)-2-(1-methyl-1H-indol-3-yl)-2-((R)-3-phenylpyrrolidin-1-yl)ethyl)-1H-indole-6-sulfonamide |

TABLE 1-continued

| Cmpd No. | Structure | Name |
| --- | --- | --- |
| 61 | 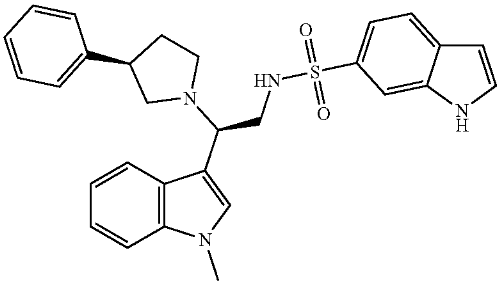 [SMILES: Cn1cc([C@H](CNS(=O)(=O)c2ccc3cc[nH]c3c2)N2CC[C@H](c3ccccc3)C2)c2ccccc21] | N-((R)-2-(1-methyl-1H-indol-3-yl)-2-((R)-3-phenylpyrrolidin-1-yl)ethyl)-1H-indole-6-sulfonamide |
| 62 | 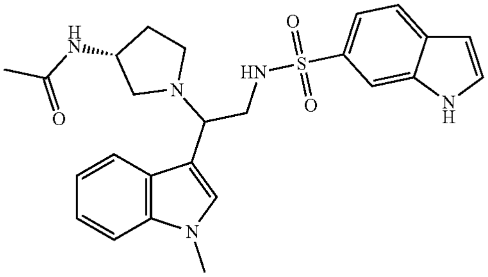 [SMILES: CC(=O)N[C@@H]1CCN(C(CNS(=O)(=O)c2ccc3cc[nH]c3c2)c2cn(C)c3ccccc23)C1] | N-((3R)-1-(2-(1H-indole-6-sulfonamido)-1-(1-methyl-1H-indol-3-yl)ethyl)pyrrolidin-3-yl)acetamide |
| 63 | 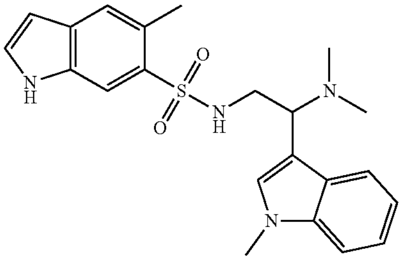 [SMILES: Cc1cc2cc[nH]c2cc1S(=O)(=O)NCC(c1cn(C)c2ccccc12)N(C)C] | N-(2-(dimethylamino)-2-(1-methyl-1H-indol-3-yl)ethyl)-5-methyl-1H-indole-6-sulfonamide |
| 64 | 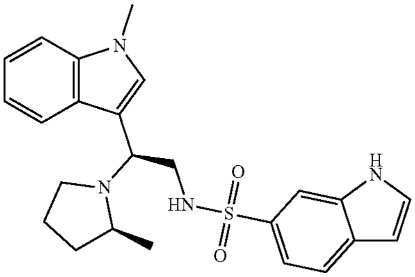 [SMILES: C[C@H]1CCCN1[C@H](CNS(=O)(=O)c1ccc2cc[nH]c2c1)c1cn(C)c2ccccc12] | N-((S)-2-(1-methyl-1H-indol-3-yl)-2-((S)-2-methylpyrrolidin-1-yl)ethyl)-1H-indole-6-sulfonamide |
| 65 | 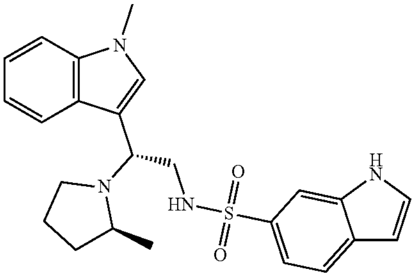 [SMILES: C[C@H]1CCCN1[C@@H](CNS(=O)(=O)c1ccc2cc[nH]c2c1)c1cn(C)c2ccccc12] | N-((R)-2-(1-methyl-1H-indol-3-yl)-2-((S)-2-methylpyrrolidin-1-yl)ethyl)-1H-indole-6-sulfonamide |

TABLE 1-continued

| Cmpd No. | Structure | Name |
|---|---|---|
| 66 | 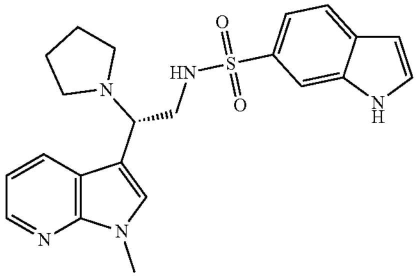 [SMILES: Cn1cc([C@@H](CNS(=O)(=O)c2ccc3cc[nH]c3c2)N2CCCC2)c2cccnc21] | (S)-N-(2-(1-methyl-1H-pyrrolo[2,3-b]pyridin-3-yl)-2-(pyrrolidin-1-yl)ethyl)-1H-indole-6-sulfonamide |
| 67 | 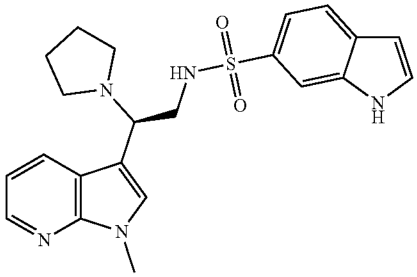 [SMILES: Cn1cc([C@H](CNS(=O)(=O)c2ccc3cc[nH]c3c2)N2CCCC2)c2cccnc21] | (R)-N-(2-(1-methyl-1H-pyrrolo[2,3-b]pyridin-3-yl)-2-(pyrrolidin-1-yl)ethyl)-1H-indole-6-sulfonamide |
| 69 | 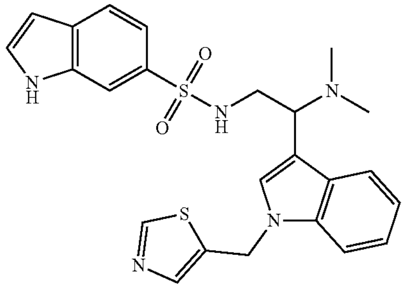 [SMILES: CN(C)C(CNS(=O)(=O)c1ccc2cc[nH]c2c1)c1cn(Cc2cncs2)c2ccccc12] | N-(2-(dimethylamino)-2-(1-(thiazol-5-ylmethyl)-1H-indol-3-yl)ethyl)-1H-indole-6-sulfonamide |
| 70 | 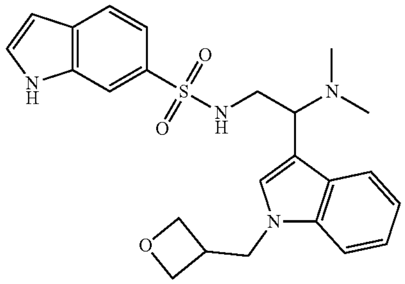 [SMILES: CN(C)C(CNS(=O)(=O)c1ccc2cc[nH]c2c1)c1cn(CC2COC2)c2ccccc12] | N-(2-(dimethylamino)-2-(1-(oxetan-3-ylmethyl)-1H-indol-3-yl)ethyl)-1H-indole-6-sulfonamide |
| 71 | 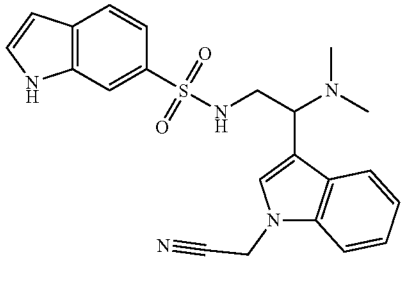 [SMILES: CN(C)C(CNS(=O)(=O)c1ccc2cc[nH]c2c1)c1cn(CC#N)c2ccccc12] | N-(2-(1-(cyanomethyl)-1H-indol-3-yl)-2-(dimethylamino)ethyl)-1H-indole-6-sulfonamide |

TABLE 1-continued

| Cmpd No. | Structure | Name |
|---|---|---|
| 72 | 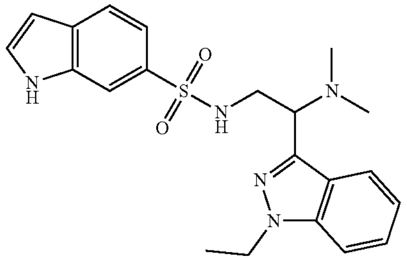 [SMILES: CCn1nc(C(CNS(=O)(=O)c2ccc3cc[nH]c3c2)N(C)C)c2ccccc21] | N-(2-(dimethylamino)-2-(1-ethyl-1H-indazol-3-yl)ethyl)-1H-indole-6-sulfonamide |
| 73 | 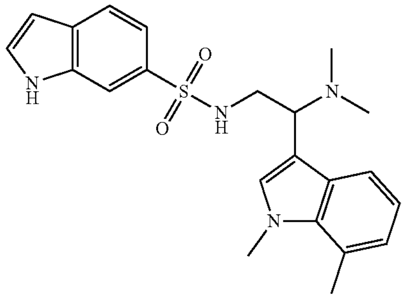 [SMILES: Cc1cccc2c(C(CNS(=O)(=O)c3ccc4cc[nH]c4c3)N(C)C)cn(C)c12] | N-(2-(1,7-dimethyl-1H-indol-3-yl)-2-(dimethylamino)ethyl)-1H-indole-6-sulfonamide |
| 74 | 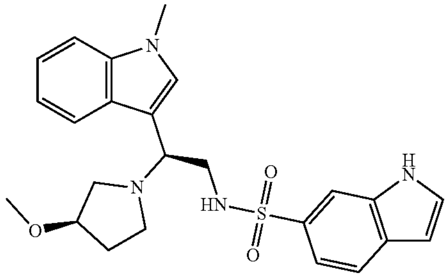 [SMILES: CO[C@@H]1CCN([C@H](CNS(=O)(=O)c2ccc3cc[nH]c3c2)c2cn(C)c3ccccc23)C1] | N-((S)-2-((R)-3-methoxypyrrolidin-1-yl)-2-(1-methyl-1H-indol-3-yl)ethyl)-1H-indole-6-sulfonamide |
| 75 | 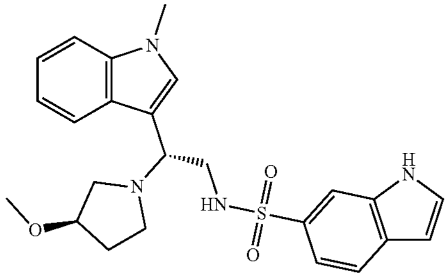 [SMILES: CO[C@@H]1CCN([C@@H](CNS(=O)(=O)c2ccc3cc[nH]c3c2)c2cn(C)c3ccccc23)C1] | N-((R)-2-((R)-3-methoxypyrrolidin-1-yl)-2-(1-methyl-1H-indol-3-yl)ethyl)-1H-indole-6-sulfonamide |
| 76 | 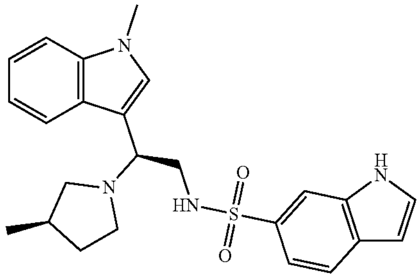 [SMILES: C[C@@H]1CCN([C@H](CNS(=O)(=O)c2ccc3cc[nH]c3c2)c2cn(C)c3ccccc23)C1] | N-((S)-2-(1-methyl-1H-indol-3-yl)-2-((R)-3-methylpyrrolidin-1-yl)ethyl)-1H-indole-6-sulfonamide |

TABLE 1-continued

| Cmpd No. | Structure | Name |
|---|---|---|
| 77 | 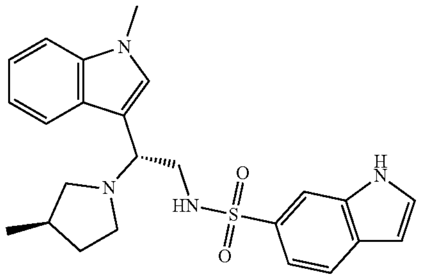 [SMILES: C[C@@H]1CCN([C@@H](CNS(=O)(=O)c2ccc3cc[nH]c3c2)c2cn(C)c3ccccc23)C1] | N-((R)-2-(1-methyl-1H-indol-3-yl)-2-((R)-3-methylpyrrolidin-1-yl)ethyl)-1H-indole-6-sulfonamide |
| 78 | 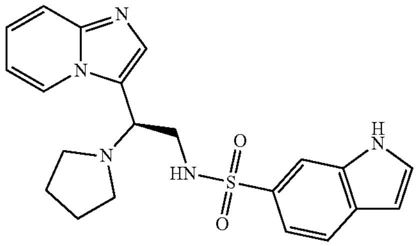 [SMILES: O=S(=O)(NC[C@H](c1cnc2ccccn12)N1CCCC1)c1ccc2cc[nH]c2c1] | (R)-N-(2-(imidazo[1,2-a]pyridin-3-yl)-2-(pyrrolidin-1-yl)ethyl)-1H-indole-6-sulfonamide |
| 79 | 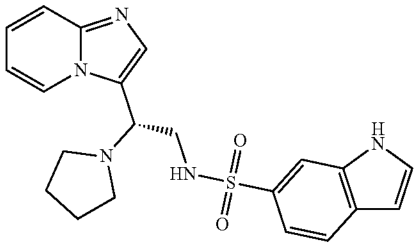 [SMILES: O=S(=O)(NC[C@@H](c1cnc2ccccn12)N1CCCC1)c1ccc2cc[nH]c2c1] | (S)-N-(2-(imidazo[1,2-a]pyridin-3-yl)-2-(pyrrolidin-1-yl)ethyl)-1H-indole-6-sulfonamide |
| 80 | 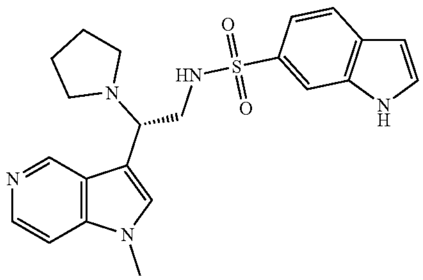 [SMILES: Cn1cc([C@@H](CNS(=O)(=O)c2ccc3cc[nH]c3c2)N2CCCC2)c2cnccc21] | (S)-N-(2-(1-methyl-1H-pyrrolo[3,2-c]pyridin-3-yl)-2-(pyrrolidin-1-yl)ethyl)-1H-indole-6-sulfonamide |
| 81 | 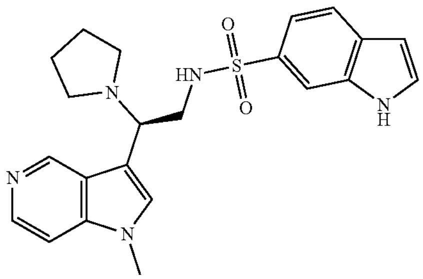 [SMILES: Cn1cc([C@H](CNS(=O)(=O)c2ccc3cc[nH]c3c2)N2CCCC2)c2cnccc21] | (R)-N-(2-(1-methyl-1H-pyrrolo[3,2-c]pyridin-3-yl)-2-(pyrrolidin-1-yl)ethyl)-1H-indole-6-sulfonamide |

TABLE 1-continued

| Cmpd No. | Structure | Name |
| --- | --- | --- |
| 82 | 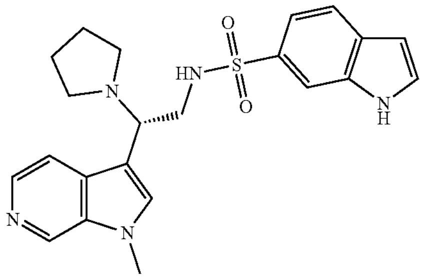 [SMILES: Cn1cc([C@@H](CNS(=O)(=O)c2ccc3cc[nH]c3c2)N2CCCC2)c2ccncc21] | (S)-N-(2-(1-methyl-1H-pyrrolo[2,3-c]pyridin-3-yl)-2-(pyrrolidin-1-yl)ethyl)-1H-indole-6-sulfonamide |
| 83 | 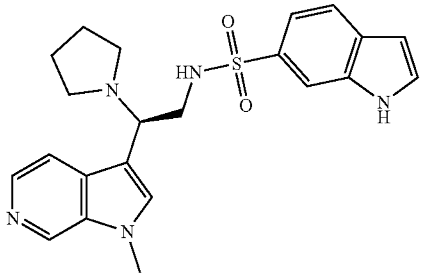 [SMILES: Cn1cc([C@H](CNS(=O)(=O)c2ccc3cc[nH]c3c2)N2CCCC2)c2ccncc21] | (R)-N-(2-(1-methyl-1H-pyrrolo[2,3-c]pyridin-3-yl)-2-(pyrrolidin-1-yl)ethyl)-1H-indole-6-sulfonamide |
| 84 | 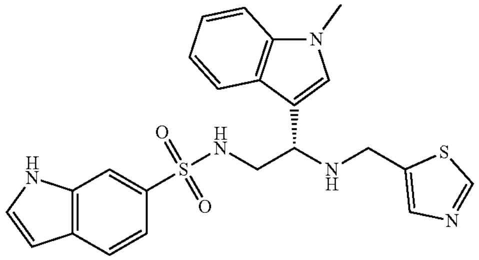 [SMILES: Cn1cc([C@@H](CNS(=O)(=O)c2ccc3cc[nH]c3c2)NCc2cncs2)c2ccccc21] | (S)-N-(2-(1-methyl-1H-indol-3-yl)-2-((thiazol-5-ylmethyl)amino)ethyl)-1H-indole-6-sulfonamide |
| 85 | 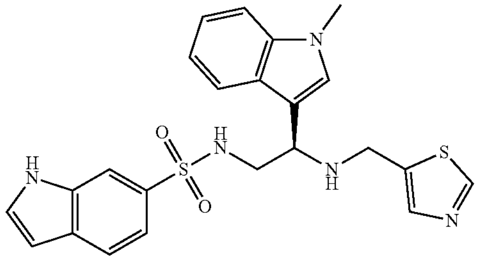 [SMILES: Cn1cc([C@H](CNS(=O)(=O)c2ccc3cc[nH]c3c2)NCc2cncs2)c2ccccc21] | (R)-N-(2-(1-methyl-1H-indol-3-yl)-2-((thiazol-5-ylmethyl)amino)ethyl)-1H-indole-6-sulfonamide |
| 86 | 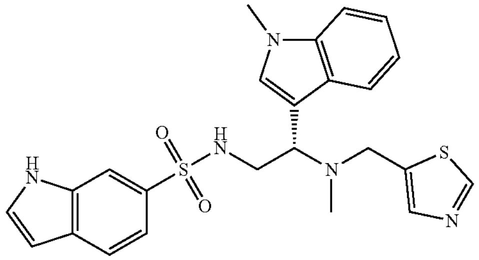 [SMILES: CN(Cc1cncs1)[C@H](CNS(=O)(=O)c1ccc2cc[nH]c2c1)c1cn(C)c2ccccc12] | (S)-N-(2-(methyl(thiazol-5-ylmethyl)amino)-2-(1-methyl-1H-indol-3-yl)ethyl)-1H-indole-6-sulfonamide |

TABLE 1-continued

| Cmpd No. | Structure | Name |
| --- | --- | --- |
| 87 | 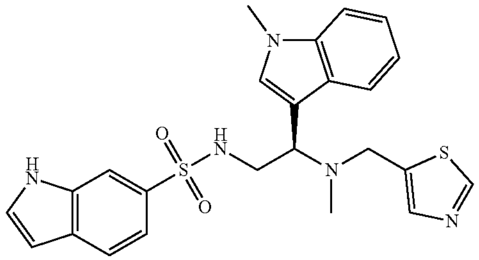 [SMILES: CN(Cc1cncs1)[C@@H](CNS(=O)(=O)c1ccc2cc[nH]c2c1)c1cn(C)c2ccccc12] | (R)-N-(2-(methyl(thiazol-5-ylmethyl)amino)-2-(1-methyl-1H-indol-3-yl)ethyl)-1H-indole-6-sulfonamide |
| 88 | 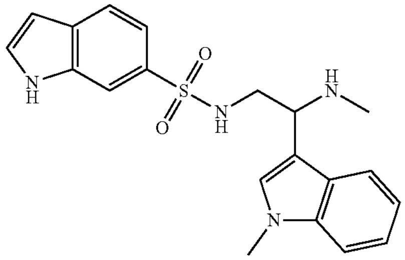 [SMILES: CNC(CNS(=O)(=O)c1ccc2cc[nH]c2c1)c1cn(C)c2ccccc12] | N-(2-(1-methyl-1H-indol-3-yl)-2-(methylamino)ethyl)-1H-indole-6-sulfonamide |
| 89 | 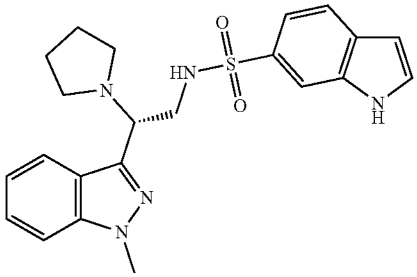 [SMILES: Cn1nc([C@@H](CNS(=O)(=O)c2ccc3cc[nH]c3c2)N2CCCC2)c2ccccc21] | (R)-N-(2-(1-methyl-1H-indazol-3-yl)-2-(pyrrolidin-1-yl)ethyl)-1H-indole-6-sulfonamide |
| 90 | 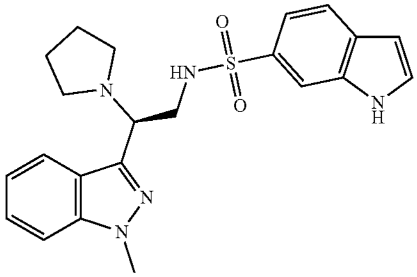 [SMILES: Cn1nc([C@H](CNS(=O)(=O)c2ccc3cc[nH]c3c2)N2CCCC2)c2ccccc21] | (S)-N-(2-(1-methyl-1H-indazol-3-yl)-2-(pyrrolidin-1-yl)ethyl)-1H-indole-6-sulfonamide |
| 91 | 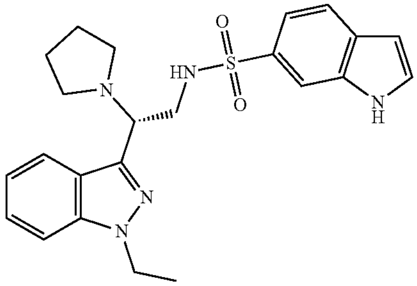 [SMILES: CCn1nc([C@@H](CNS(=O)(=O)c2ccc3cc[nH]c3c2)N2CCCC2)c2ccccc21] | (R)-N-(2-(1-ethyl-1H-indazol-3-yl)-2-(pyrrolidin-1-yl)ethyl)-1H-indole-6-sulfonamide |

TABLE 1-continued

| Cmpd No. | Structure | Name |
| --- | --- | --- |
| 92 | 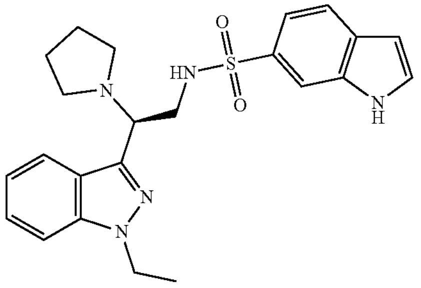 [SMILES: CCn1nc([C@H](CNS(=O)(=O)c2ccc3cc[nH]c3c2)N2CCCC2)c2ccccc21] | (S)-N-(2-(1-ethyl-1H-indazol-3-yl)-2-(pyrrolidin-1-yl)ethyl)-1H-indole-6-sulfonamide |
| 93 | 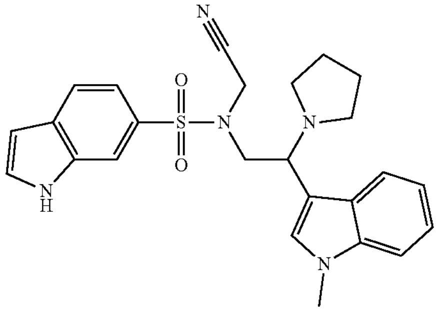 [SMILES: Cn1cc(C(CN(CC#N)S(=O)(=O)c2ccc3cc[nH]c3c2)N2CCCC2)c2ccccc21] | N-(cyanomethyl)-N-(2-(1-methyl-1H-indol-3-yl)-2-(pyrrolidin-1-yl)ethyl)-1H-indole-6-sulfonamide |
| 94 | 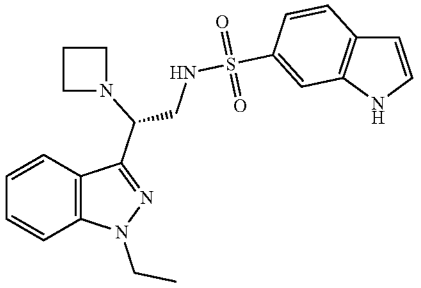 [SMILES: CCn1nc([C@@H](CNS(=O)(=O)c2ccc3cc[nH]c3c2)N2CCC2)c2ccccc21] | (R)-N-(2-(azetidin-1-yl)-2-(1-ethyl-1H-indazol-3-yl)ethyl)-1H-indole-6-sulfonamide |
| 95 | 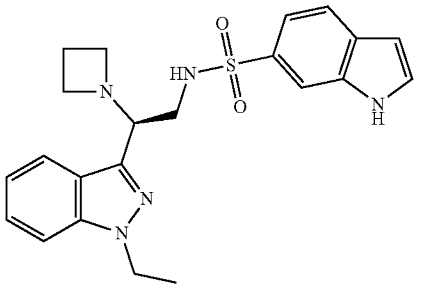 [SMILES: CCn1nc([C@H](CNS(=O)(=O)c2ccc3cc[nH]c3c2)N2CCC2)c2ccccc21] | (S)-N-(2-(azetidin-1-yl)-2-(1-ethyl-1H-indazol-3-yl)ethyl)-1H-indole-6-sulfonamide |
| 96 | 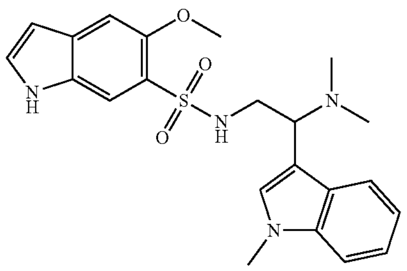 [SMILES: COc1cc2cc[nH]c2cc1S(=O)(=O)NCC(c1cn(C)c2ccccc12)N(C)C] | N-(2-(dimethylamino)-2-(1-methyl-1H-indol-3-yl)ethyl)-5-methoxy-1H-indole-6-sulfonamide |

TABLE 1-continued
| Cmpd No. | Structure | Name |
| --- | --- | --- |
| 97 | 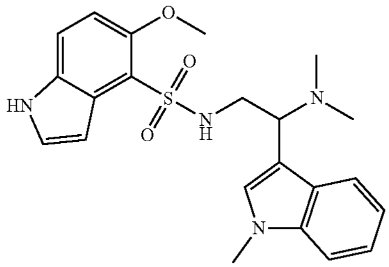 [SMILES: COc1ccc2[nH]ccc2c1S(=O)(=O)NCC(c1cn(C)c2ccccc12)N(C)C] | N-(2-(dimethylamino)-2-(1-methyl-1H-indol-3-yl)ethyl)-5-methoxy-1H-indole-4-sulfonamide |
| 98 | 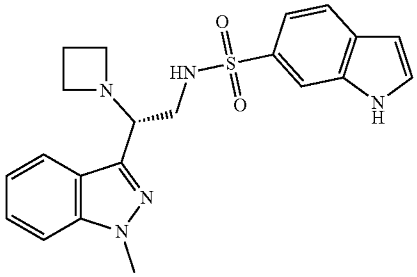 [SMILES: Cn1nc([C@@H](CNS(=O)(=O)c2ccc3cc[nH]c3c2)N2CCC2)c2ccccc21] | (R)-N-(2-(azetidin-1-yl)-2-(1-methyl-1H-indazol-3-yl)ethyl)-1H-indole-6-sulfonamide |
| 99 | 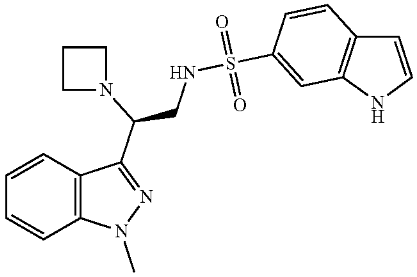 [SMILES: Cn1nc([C@H](CNS(=O)(=O)c2ccc3cc[nH]c3c2)N2CCC2)c2ccccc21] | (S)-N-(2-(azetidin-1-yl)-2-(1-methyl-1H-indazol-3-yl)ethyl)-1H-indole-6-sulfonamide |
| 100 | 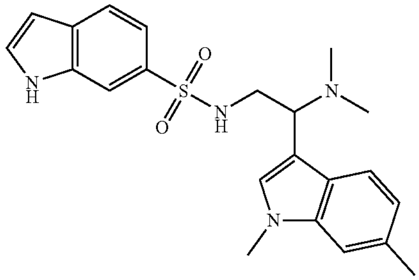 [SMILES: Cc1ccc2c(C(CNS(=O)(=O)c3ccc4cc[nH]c4c3)N(C)C)cn(C)c2c1] | N-(2-(1,6-dimethyl-1H-indol-3-yl)-2-(dimethylamino)ethyl)-1H-indole-6-sulfonamide |
| 101 | 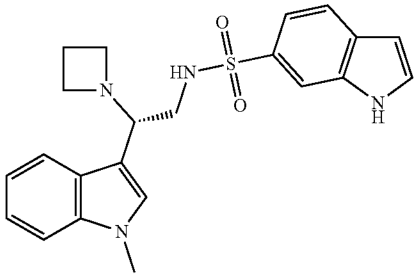 [SMILES: Cn1cc([C@@H](CNS(=O)(=O)c2ccc3cc[nH]c3c2)N2CCC2)c2ccccc21] | (S)-N-(2-(azetidin-1-yl)-2-(1-methyl-1H-indol-3-yl)ethyl)-1H-indole-6-sulfonamide |

TABLE 1-continued

| Cmpd No. | Structure | Name |
|---|---|---|
| 102 | 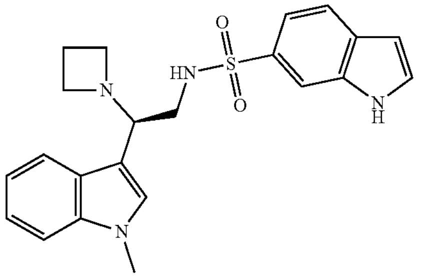 [SMILES: Cn1cc([C@H](CNS(=O)(=O)c2ccc3cc[nH]c3c2)N2CCC2)c2ccccc21] | (R)-N-(2-(azetidin-1-yl)-2-(1-methyl-1H-indol-3-yl)ethyl)-1H-indole-6-sulfonamide |
| 103 | 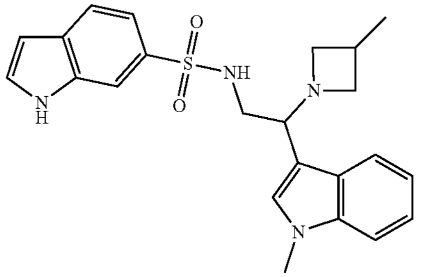 [SMILES: CC1CN(C(CNS(=O)(=O)c2ccc3cc[nH]c3c2)c2cn(C)c3ccccc23)C1] | N-(2-(1-methyl-1H-indol-3-yl)-2-(3-methylazetidin-1-yl)ethyl)-1H-indole-6-sulfonamide |

Further Forms of Compounds

The invention provides salts of any one of the compounds described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, an imidazole salt, or a pyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The compounds described herein may in some cases exist as diastereomers, enantiomers, or other stereoisomeric forms. The compounds and salts presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

The methods, compositions, and formulations described herein include the use of amorphous forms as well as crystalline forms (also known as polymorphs). Active metabolites of compounds or salts described herein having the same type of activity are included in the scope of the present disclosure. In addition, the compounds described herein can exist in unsolvated as well as solvated forms with pharmaceutically acceptable solvents such as water, ethanol, and the like. The solvated forms of the compounds and salts presented herein are also considered to be disclosed herein.

According to another embodiment, the present disclosure provides methods of producing the above-defined compounds. The compounds may be synthesized using conventional techniques. Advantageously, these compounds are conveniently synthesized from readily available starting materials. Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

In some embodiments, compounds described herein modulate the conformation of alphaB-crystallin (cryAB). In certain embodiments, compounds or salts described herein that modulate the conformation of cryAB may be identified with the assay method described in Examples A-1 and A-2. In some embodiments, a compound is considered active if melting temperature ($T_m$) differences between the presence and absence of compound ($\Delta T_m$) exceed two or three standard deviations of negative controls (protein in the absence of compound and containing DMSO vehicle only). In some embodiments, a compound is considered inactive if the change in melting temperature ($\Delta T_m$) does not exceed two standard deviations of the negative controls.

Pharmaceutical Formulations

Provided herein, in certain embodiments, are compositions comprising a therapeutically effective amount of any compound or salt described herein (also referred to herein as "the pharmaceutical agent"). In certain embodiments, the compositions comprise a therapeutically effective amount of any compound or salt described herein; and a pharmaceutically acceptable excipient. In certain embodiments, a pharmaceutical formulation may be used in any of the methods described herein.

In certain embodiments, a compound described herein is used for the treatment of an ophthalmic disorder such as cataracts or presbyopia. A formulation administered to the eye may be administered by injection, for example, by intravitreal or intracameral injection. A formulation administered to the eye may be administered topically, for example, with an ointment, cream, or eye drop.

Methods of the Disclosure

The disclosure provides compounds and formulations for use in reducing or preventing alpha-crystallin protein aggregation. The aggregation of alpha-crystallin has been implicated in a variety of diseases of which the compounds and formulations described herein may be used to treat or prevent. Such diseases include, for example, cataracts, nuclear sclerosis, presbyopia, neurological diseases, Alexander disease, Creutzfeldt-Jacob disease, Alzheimer's disease, and Parkinson's disease.

In certain embodiments, the methods provided herein can be used to treat a disease or a condition that would benefit from reducing the likelihood of or reversing the aggregation of alpha-crystallin. The compounds or salts disclosed herein can be used as pharmacological chaperones of alpha-crystallin.

The methods provided herein can be used to treat, for example, a vision disorder such as cataract, age-related cataract, diabetic cataract, a cataract associated with surgery, a cataract resulting from radiation, a cataract resulting from a genetic illness, a cataract resulting from an infection, a cataract resulting from medication, or a hereditary form of cataract with early onset.

Vision disorders, as discussed herein, refer to disordered vision that may be associated with aberrant aggregation of crystallin proteins in the lens of the eye. The aberrant aggregation of crystallin proteins may be the primary factor resulting in the vision disorder or may be one of a plurality of mechanisms resulting in the vision disorder. Vision disorders of the disclosure include, but are not limited to, cataract, such as nuclear cataract, cortical cataract, posterior capsular cataract, congenital cataract, early-onset hereditary cataract, metabolic (diabetic) cataract, secondary cataract, blunt traumatic cataract, penetrating traumatic cataract, post-vitrectomy cataract, radiation-induced cataract; and presbyobia, such as incipient presbyopia, functional presbyopia, absolute presbyopia, premature presbyopia or nocturnal presbyopia.

The methods of the invention can also be used to treat disease caused by an alphaA- or alphaB-crystallin mutation. The mutation in alphaA- or alphaB-crystallin can lead to hereditary cataract. Examples of alphaA-crystallin mutations include, but are not limited to, W9X, R12C, R21L, R21W, R49C, R54C, F71L, G98R, D105H, R116C, and R116H. Examples of alphaB-crystallin mutations include, but are not limited to, 150delA (aB184), R11H, P20S, R56W, R69C, D109H, R120G, D140N, and A171T. In some instances, the alphaB-crystallin mutation is D109H or R120G.

In certain embodiments, the compounds and formulations disclosed herein are used to treat a subject with a vision disorder, such as cataract or presbyopia. In certain embodiments, the compounds and formulations disclosed herein may be used to treat cataract of a subject, such as nuclear cataract, cortical cataract, posterior capsular cataract, congenital cataract, secondary cataract, traumatic cataract, radiation cataract. In certain embodiments, a subject has one or more symptoms of cataract, such as clouded vision, blurred vision, dim vision, trouble seeing at night, sensitivity to light and glare, need for brighter light for reading and other activities, seeing "halos" around lights, frequent changes in eyeglasses or contact lens prescription, fading or yellowing of colors, and double vision in a single eye.

In certain embodiments, the compounds and formulations disclosed herein may be used to treat presbyopia of a subject, such as incipient presbyopia, functional presbyopia, absolute presbyopia, premature presbyopia or nocturnal presbyopia. In certain embodiments, the subject has one or more symptoms of presbyopia, such as decreased focusing ability for near objects, eyestrain, difficulty reading fine print, fatigue while reading or looking at an illuminated screen, difficulty seeing clearly up close, less contrast when reading print, need for brighter and more direct light for reading, needing to hold reading material further away in order to see it clearly, or headaches, especially headaches when using near vision. In some embodiments the subject does not have a cataract in an eye afflicted with presbyopia.

In certain embodiments, the subject has a vision disorder in one eye. In certain embodiments, the subject has a vision disorder in both eyes.

The subject of the disclosure can be any vertebrate animal. In some preferred embodiments the subject is a human. The subject may be of any age. In some embodiments the subject may be between 25 and 100 years of age, or between 40 and 100 years of age, or between 50 and 100 years of age. The subject may be over 1 year of age, over 2 years of age, over 5 years of age, over 10 years of age, over 18 years of age, over 20 years of age, over 25 years of age, over 30 years of age, over 35 years of age, over 40 years of age, over 45 years of age, over 50 years of age, over 60 years of age, over 70 years of age, over 80 years of age or over 90 years of age. The subject may be 25 years of age or older.

The methods provided herein can be used to treat a disease or a condition that would benefit from reducing the likelihood of or reversing the aggregation of alpha-crystallin by administering an effective amount of at least one of the compounds or formulations described herein. An effective amount can be an amount that reduces or inhibits the aggregation of alpha-crystallin. In certain embodiments, compounds and formulations of the disclosure reduce alpha-crystallin aggregation in an eye by about 1% to about 100%, about 1% to about 90%, about 1% to about 80%, about 1% to about 70%, about 10% to about 50%, about 20% to about 40%, about 50% to about 90% or between 60% to about 95% relative to a pre-treatment value for alpha-crystallin aggregation.

In certain embodiments, the compound or salt of the disclosure is a pharmacological chaperone that binds to the alpha-crystallin, such as the pharmacological chaperone can bind to a concave pocket near the antiparallel beta strand dimer interface site of alpha-crystallin. The concave pocket of alpha-crystallin can comprise serine 66, leucine 79, aspartate 80, valine 81, lysine 82, histidine 83, phenylalanine 84, valine 97, isoleucine 114, serine 115, arginine 116, aspartate 117, phenylalanine 118, histidine 119, arginine 120, lysine 121 and tyrosine 122 of αB-crystallin or αA-crystallin. In certain embodiments, the pharmacological chaperone can be, for example, a small molecule or a sterol or a sterol mimetic.

The compounds and formulations disclosed herein may be used to inhibit the aggregation of alpha-crystallin by at least about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% when compared to a pre-treatment level or a level observed in biologically matched control subject or specimen that was not administered said compounds. The compound and formulations disclosed herein may inhibit the aggregation of the alpha-crystallin by between 1% and 100%, between 5% and 90%, between 10% and 80%, between 20% and 50%, between 50% and 95%, between 60% and 99% or between 40% and 70% when compared to a pre-treatment level or a level observed in biologically matched control subject or specimen that was not administered said compounds.

In certain embodiments, the amyloid forming protein can be selected from a group consisting of Hsp27, αA-crystallin, αB-crystallin, βB2-crystallin βB1-crystallin, TD-crystallin, Hsp22, Hsp20, HSPB2, HSPB3, HSPB7, HSPB9, HSPB10, tau, Alphasynuclein, IAPP, beta-amyloid, PrP, Huntingtin, Calcitonin, Atrial natriuretic factor, Apolipoprotein AI, Serum amyloid A, Medin, Prolactin, Transthyretin, Lysozyme, Beta 2 microglobulin, Gelsolin, Keratoepithelin, Cystatin, Immunoglobulin light chain AL, myocilin, and SIBM.

Alpha-crystallin aggregation in the lens may be measured with, for example, in vivo dynamic light scattering, light scattering assays, electron microscopy, centrifugation protein solubility assays, filter trap protein solubility assays, thioflavin T-fluorescence assays, high performance liquid chromatography, gel-permeation chromatography, size exclusion chromatography, anti-amyloid antibody assays. In certain embodiments, exemplary methods of the disclosure for measuring alpha-crystallin aggregation in the lens are described in: K. Dierks et al, SPIE Vol. 2330 Lasers in Ophthalmology 11, 112-121 (1994); R. Ansari, Journal of Biomedical Optics January/February, Vol. 9, No. 1, 22-37 (2004); and X. Pei et al, Br J Ophthalmol 92, 1471-1475 (2008), the contents of each of which are incorporated by reference herein.

The compounds disclosed herein can inhibit cataract formation by at least about 1%, about 2%, about 3%, about 4%, about 5%, about 6%, about 7%, about 8%, about 9%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100% when compared to the level observed in biologically matched control subject or specimen that was not administered said compounds.

In certain embodiments, prior to treatment, the subject has experienced a loss of near vision. The subject may have experienced a loss of near vision which first occurred when the subject was 25 years of older. The subject may have been about 25 to 50 years old, such as about 25 to 40 years old, such as about 25 to 35 years old when the subject experienced a loss of near vision. The subject may have been diagnosed, e.g., diagnosed by a medical practitioner, as suffering a loss of near vision, or may self-identify as suffering a loss of near vision.

In certain embodiments, the subject has not yet experienced a decline in near vision. The subject may have one or more risk factors for the development of presbyopia. Risk factors include, but are not limited to: age over 40, hyperopia, an occupation with high near vision demands, gender, ocular disease or trauma, systemic disease, drug exposure (prescription and nonprescription), iatrogenic factors, proximity to the equator, exposure to high levels of UV radiation, poor nutrition, decompression sickness, and exposure to high ambient temperatures.

The subject may exhibit one or more symptoms of hyperopia. Some symptoms of hyperopia include: blurred vision, difficulty seeing objects up close, crossing of the eyes in children (esotropia). The subject may experience a loss of near vision. The loss of near vision may be a hyperopia or may not be a hyperopia. In some embodiments the loss of near vision is not related to a focus point of light rays behind the retina. In some embodiments the subject may not exhibit one or more symptoms of hyperopia.

A loss of near vision can be identified by an eye exam method, such as eye examinations used commonly in the field. A loss of near vision may be determined by assessing one or more of near vision acuity, habitual distance visual acuity, corrected near visual acuity, refractive error, optical power, Jaeger score, Log MAR score, ETDRS scale, reading speed, accommodative amplitude of the lens, or any other method known in the art. The subject may exhibit an age related loss of near vision as determined by one or more of the following of the methods above. Eye tests may be used to evaluate binocular vision, or used to evaluate each eye separately.

Vision acuity, or visual acuity, is commonly measured by requiring a subject to identify differently sized optotypes on a chart which is viewed at a set distance. The optotypes can be stylized letters or symbols. Viewing distance is typically such that the lens of the eye adjusts for either near vision or far distance vision. To measure near vision acuity the chart would be viewed at a set reading distance, typically 1. Many charts are known in the field, commonly used charts include the Snellen Chart the Log Mar chart and the ETDRS chart. Some examples of visual acuity charts that can be used for illiterate subjects include, but are not limited to, the tumbling E chart, the Landolt C chart, and the LEA test. A reference value based on the size of optotypes that a person with 'normal' eyesight would be able to resolve is used to assign a visual acuity score. For example, in a distance visual acuity test each line of optotypes is annotated with the distance from which a subject with 'normal' vision could read them. A subject then views the chart from 20 feet (or 6 meters) and reads the optotypes from largest to smallest, stopping at the smallest line which they are able to read with no mistakes, or with no more than one mistake, or with no more than two mistakes. If the smallest optotypes the subject can read are the ones annotated as 40 feet, then the subject has 20/40 vision, meaning that they can read at 20 feet what a subject with 'normal' eyesight can read at 40 feet. An efficient way to state acuity is by solving the fraction to a decimal number, thus a subject with 20/40 vision would have a decimal distance visual acuity of 0.5.

Near vision acuity can be measured in the same way but with a deceased viewing distance. In an example near vision test, the subject is instructed to cover one eye and use the other eye to view the eye chart from a distance of 16 inches. The tester determines the smallest size of character that the subject is able to read missing no more than one character, and correlates said character size with the distance from which a subject with 'normal' vision could read that size. The fraction may be converted to a decimal to give a decimal visual acuity value.

The subject of the methods of this disclosure may have a vision impairment determined by a near visual acuity of 0.9 or less. The subject of the methods of this disclosure may have a vision impairment determined by a near visual acuity of 0.8 or less. The subject of the methods of this disclosure may have a vision impairment determined by a near visual acuity of 0.6 or less. The subject of the methods of this disclosure may have a vision impairment determined by a near visual acuity of 0.4 or less.

Habitual distance visual acuity is the visual acuity of a subject with a correction. In some cases, this is no correction, in some cases this may be eyeglasses or contact lenses. In cases where habitual distance visual acuity includes eye glasses or contact lenses the correction may not be optimal for the subject's current needs.

In certain embodiments, the subject may experience difficulties with reading. The subject may have trouble reading small print or reading print that they were previously able to read without trouble. The subject may have a decreased reading speed. The subject may complain of eye strain after extended periods of reading.

In certain embodiments, the subject has a near vision impairment that could alternatively be corrected with eye glasses or contact lenses having power of about +0.5D or higher, about +1D or higher or about +2D or higher. In some embodiments a subject of this disclosure could be identified as a person who occasionally or habitually uses eye glasses or contact lenses to correct a near vision impairment. The subject of this disclosure could be a person who occasionally or habitually uses reading glasses.

The near vision impairment may be determined by measuring the optical power of the lens of the eye. The optical power (also referred to as dioptric power, refractive power, focusing power, or convergence power) is the degree to which a lens converges light. The optical power is equal to the reciprocal of the focal length in meters and is expressed in diopters. For example, a lens which can bring parallel rays of light to a focus at ⅓ of a meter has an optical power of 3 diopters. The ability to focus on near objects declines through life and levels off at 0.5 to 1 diopters at age 60.

An eye that has too much or too little optical power to focus light onto the retina may have a refractive error. A refractive error may be assessed using one or more of the following: a retinoscope, an automated refractor, a Shack-Hartmann wavefront sensor or a pinhole occluder.

The lens of a subject may have an optical power of less than 15 diopters before treatment with the compound described herein. The lens of a subject may have an optical power of less than 20 diopters before treatment with the compound described herein.

The near vision impairment may be determined by the Jaeger test scale. The Jaeger chart is a type of eye chart used in testing near vision acuity. It is a card on which lines of paragraphs of text are printed at increasing size. Several variations of the Jaeger chart exist. This card is to be held by a subject at a fixed distance from the eye. The smallest print that the subject can read determines their visual acuity and their Jaeger score (J1 to J11 or larger). For example, a subject who could read lines 4 and higher from the Jaeger chart would have a visual acuity of J4.

The near vision impairment may be determined by a score of J2 or higher on the Jaeger scale of the Jaeger test. The near vision impairment may be determined by a score of J3 or higher on the Jaeger scale of the Jaeger test. The near vision impairment may be determined by a score of J4 or higher on the Jaeger scale of the Jaeger test. The near vision impairment may be determined by a score of J5 or higher on the Jaeger scale. The near vision impairment may be determined by a score of J6 or higher on the Jaeger scale. The vision impairment may be determined by a score of J8 or higher on the Jaeger scale.

The near vision impairment may be determined by the Log MAR chart. When using the Log MAR chart, visual acuity is scored with reference to the Logarithm of the Minimum Angle of Resolution. A subject who can resolve details as small as 1 minute of visual angle scores Log MAR 0, (base-10 logarithm of 1 is 0); a subject who can resolve details as small as 2 minutes of visual angle (i.e., reduced acuity) scores Log MAR (base-10 logarithm of 2 is 0.3); and so on. A Log MAR score is calculated based on the number of letters the subject identifies correctly (each line is worth 0.1 Log MAR units).

The near vision impairment may be determined by a Log MAR score of 0.3 or higher. The near vision impairment may be determined by a Log MAR score of 0.4 or higher.

The near vision impairment may be determined by a Log MAR score of 0.5 or higher. The near vision impairment may be determined by a Log MAR score of 0.6 or higher.

Use of the methods of this disclosure may treat or prevent presbyopia. Use of the methods of this disclosure by a subject who has not yet experienced symptoms of presbyopia may prevent or delay the onset of presbyopia.

Use of the methods of this disclosure by a subject with presbyopia may prevent or delay the progression of presbyopia. In some embodiments the subject does not experience a decline in near vision acuity over a period of time while being administered the compound described herein.

Use of the methods of this disclosure by a subject with presbyopia may treat the presbyopia resulting in an improvement in near vision acuity. The improvement of the near vision of the subject may comprise an improvement in one or more of visual acuity, optical power, accommodative amplitude of the lens, Jaeger scale score, Log MAR scale score, ETDRS scale, reading speed, or refractive error.

In certain embodiments, the improvement of the near vision of the subject may comprise an improvement in near visual acuity relative to a pre-treatment near visual acuity value. In certain embodiments, the methods of the disclosure improve near vision impairment to a degree that is about equivalent to eye glasses or contact lenses having a power of about +0.5D or higher, about +1D or higher or about +2D or higher. In certain embodiments, the methods of the disclosure can replace treatment with eye glasses or contact lenses or surgical procedures.

In certain embodiments, methods of the disclosure result in improvement in near vision acuity of the subject. The methods of this disclosure may increase the optical power of a lens of a subject. In certain embodiments, the optical power of a lens may improve by at least 0.1 diopters relative to a pre-treatment optical power of the lens. In certain embodiments, the optical power of a lens may improve by at least 1 diopter relative a pre-treatment optical power of the lens. In certain embodiments, the optical power of a lens may improve by at least 5 diopters relative to a pre-treatment optical power of the lens. In certain embodiments, the optical power of a lens may improve by between 0.1 and 20 diopters relative to a pretreatment optical power of the lens. In certain embodiments, the optical power of a lens may improve by between 0.1 and 10 diopters relative to a pre-treatment optical power of the lens. In certain embodiments, the optical power of a lens may improve by between 1 and 10 diopters relative to a pre-treatment optical power of the lens. In certain embodiments, the optical power of a lens may improve by between 1 and 5 diopters relative to a pre-treatment optical power of the lens.

In certain embodiments, the treatment improves the subject's near vision, e.g., by 1, 2, 3, 4, or 5 Jaeger lines, e.g., as measured by the Jaeger test scale, relative to a pre-treatment measurement. The treatment may improve a subject's near vision by 1-7 Jaeger lines, or by 1-5 Jaeger lines, or by 1-3 Jaeger lines, relative to a pre-treatment measurement.

In certain embodiments, the treatment corrects the subject's near vision, e.g., by 0.02, 0.04, 0.06, 0.1, 0.2, 0.3, 0.4, 0.5, or more than 0.5 Log MAR units. The treatment may correct the subject's near vision by 0.02-0.9 Log MAR units, or by 0.1-0.8 Log MAR units, or by 0.2-0.5 Log MAR units.

The McDonald-Shadduck scoring system can be used to determine the severity of various ocular symptoms upon administration of a compound of the present invention in rabbits. The scoring system can use a scale ranging from 0-6, where a higher number indicates greater severity of the ocular condition. The McDonald-Shadduck scoring system can be used to assess, for example, corneal opacity, corneal vascularization, conjunctival chemosis and swelling, conjunctival discharge, and corneal staining.

The McDonald-Shadduck scoring system can be used to grade conjunctival discharge. Conjunctival discharge can be used to describe discharge that is a whitish or gray precipitate. Discharge that is clear, inspissated, congealed, or mucoid found in the medial canthus of the rabbits is not scored as part of the conjunctival discharge scale.

Aqueous flare can be measured by the presence of the Tyndall phenomenon in the anterior chamber of the eye. The Tyndall phenomenon can be used to describe light scattering by particles in a colloid or particles in a fine suspension. The intensity of the Tyndall phenomenon can be scored by comparing the normal Tyndall effect observed when a slitlamp beam passes through the lens with the passage of a slitlamp beam passed through the anterior chamber. The presence of an aqueous flare can be indicative of a breakdown of the blood-aqueous barrier.

Iris involvement can be measured using the McDonald-Shadduck scoring system. The primary, secondary, and tertiary vessels of the iris can be used an aid to determine a subjective ocular score for iris involvement. The intensity of iris involvement can increase when hyperaemia of the vessels is high, and there is greater involvement of the secondary and tertiary vessels.

EXAMPLES

I: Chemical Synthesis

The following examples illustrate the various methods of making compounds described herein. It is understood that one skilled in the art may be able to make these compounds by similar methods or by combining other methods known to one skilled in the art. It is also understood that one skilled in the art would be able to make, in a similar manner as described below by using the appropriate starting materials and modifying the synthetic route as needed. In general, starting materials and reagents can be obtained from commercial vendors or synthesized according to sources known to those skilled in the art or prepared as described herein.

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: Preparation of N-(2-(1-methyl-1H-indol-3-yl)-2-(pyrrolidin-1-yl)ethyl)-1H-indole-6-sulfonamide (Compound 5)

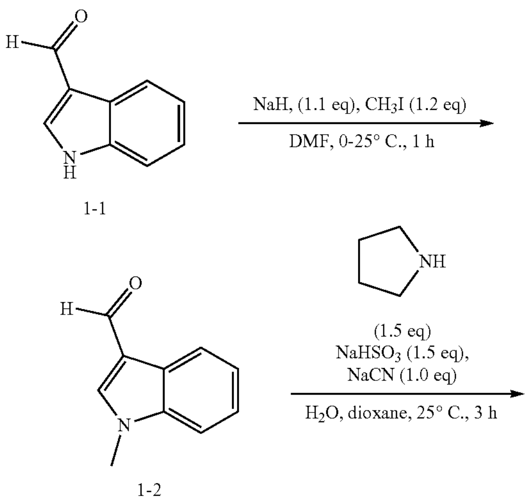

1-1
1-2

-continued

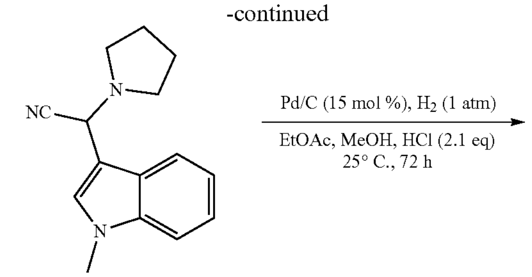

1-3

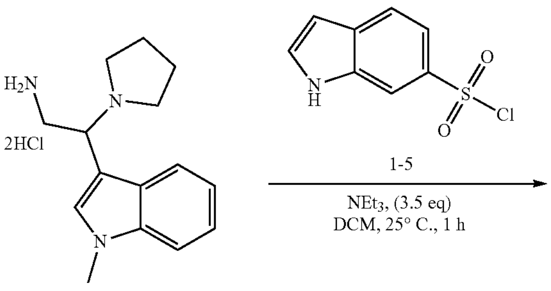

1-5

1-4

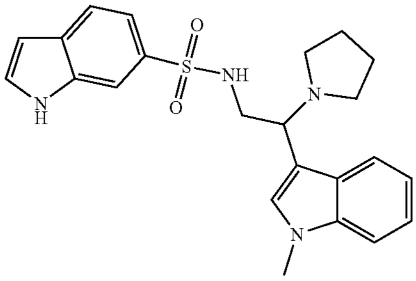

Compound 5

Step 1 (Intermediate 1-2): To a solution of 1-1 (20.0 g, 137.8 mmol, 1.0 equiv.) in DMF (150 mL) was added NaH (6.1 g, 60% in mineral oil, 151.6 mmol, 1.1 equiv.) portion-wise at 0° C. The mixture was stirred at 0° C. for 30 min, followed by the addition of iodomethane (10.3 mL, 165.4 mmol, 1.2 equiv.) at 0° C. The mixture was warmed to 25° C. and stirred for 1 h before quenching with water (750 mL). The precipitate was filtered and washed with water (100 mL), dried under vacuum to afford compound 1-2 (20.1 g, 91% yield) as brown solid. $^1$H NMR (400 MHz, $CDCl_3$) δ 9.98 (s, 1H), 8.30 (d, J=6.6 Hz, 1H), 7.66 (s, 1H), 7.42-7.28 (m, 3H), 3.86 (s, 3H).

Step 2 (Intermediate 1-3): To a solution of 1-2 (3.0 g, 18.8 mmol, 1.0 equiv.) in $H_2O$ (30 mL) and dioxane (30 mL) was added $NaHSO_3$ (2.93 g, 28.2 mmol, 1.5 equiv.) at 25° C. The mixture was stirred at 25° C. for 15 min. Subsequently, pyrrolidine (2.4 mL, 28.2 mmol, 1.5 equiv.) was added to the mixture which was stirred for another 35 min. NaCN was added and stirred for 3 h at 25° C. The solid was filtered, rinsed with water (50 mL) and dried under vacuum. Compound 1-3 (3.5 g, 78% yield) was obtained as white solid. $^1$H NMR (400 MHz, $CDCl_3$) δ 7.79 (d, J=8.0 Hz, 1H), 7.31 (d, J=8.2 Hz, 1H), 7.28-7.24 (m, 1H), 7.22 (s, 1H), 7.14 (t, J=7.4 Hz, 1H), 5.27 (s, 1H), 3.77 (s, 3H), 2.81-2.61 (m, 4H), 1.90-1.71 (m, 4H). $^{13}$C NMR (101 MHz, $CDCl_3$) δ 137.45, 128.04, 126.25, 122.46, 119.83, 119.76, 116.87, 109.57, 108.87, 52.22, 50.25, 32.95, 23.66.

Step 3 (Intermediate 1-4): Compound 1-3 (3.5 g, 14.6 mmol, 1.0 equiv.) was dissolved in EtOAc (75 mL) and MeOH (150 mL). Then Pd/C (2.4 g, 10% of Pd on carbon, 2.3 mmol, 0.15 equiv.) and HCl (2.6 mL, 12 mol/L in water, 31.2 mmol, 2.1 equiv.) were added at 25° C. The flask was equipped with a balloon of $H_2$. The mixture was stirred at 25° C. for 72 h before filtration through celite. The filtrate was concentrated to afford a brown residue which was purified by prep-HPLC ($MeCN/H_2O$=10:90, 0.1% of HCl as additive) to afford 1-4 (0.53 g, 11% of yield) as white solid. ESI-TOF m/z calcd. for $C_{15}H_{22}N_3^+$: 244.2, found 244.2. $^1$H NMR (400 MHz, DMSO) δ 11.97 (s, 1H), 8.37 (s, 3H), 7.87 (d, J=7.9 Hz, 1H), 7.85 (s, 1H), 7.54 (d, J=8.2 Hz, 1H), 7.26 (t, J=7.3 Hz, 1H), 7.17 (t, J=7.3 Hz, 1H), 5.17-5.07 (m, 1H), 3.84 (s, 3H), 3.81-3.62 (m, 3H), 3.25-3.18 (m, 1H), 3.05-2.89 (m, 2H), 1.94-1.71 (m, 4H).

Step 4 (Intermediate 1-5): To a solution of 6-bromo-1H-indole (2.4 g, 12.2 mmol, 1.0 equiv.) in THE (30 mL) was added NaH (0.49 g, 60% in mineral oil, 12.2 mmol, 1.0 equiv.) at 0° C. After stirring for 15 min, the mixture was cooled at −78° C., and tBuLi (23.5 mL, 1.3 mol/L in hexane, 30.5 mmol, 2.5 equiv.) was added dropwise. The mixture was stirred at −78° C. for 45 min. Then, $SO_2$ (10.5 mL, 2.9 mol/L in THF, 30.5 mmol, 2.5 equiv.) was added at −78° C. The mixture was warmed to 25° C. and stirred for 16 h. Petroleum ether (30 mL) and AcOH (0.77 mL, 13.4 mmol, 1.1 equiv.) were added. The mixture was stirred for 15 min and filtered off. The filter cake was rinsed with petroleum ether (10 mL). The solid was suspended in DCM (35 mL), and then NCS (1.63 g, 12.2 mmol, 1.0 equiv.) was added. The mixture was stirred at 25° C. for 30 min, and filtered. The filtrate was taken to dryness to afford a brown solid which was purified on silica gel column (petroleum ether/EtOAc=20:1 then 5:1) to obtain compound 1-5 (1.1 g, 42% of yield) as yellow solid. $^1$H NMR (400 MHz, $CDCl_3$) δ 8.75 (s, 1H), 8.17 (s, 1H), 7.82 (d, J=8.6 Hz, 1H), 7.77 (dd, J=8.6, 1.7 Hz, 1H), 7.60-7.53 (m, 1H), 6.76-6.67 (m, 1H).

Step 5 (Compound 5): To a solution of compound 1-4 (0.300 g, 0.79 mmol, 1.0 equiv.) and $NEt_3$ (0.47 mL, 2.77 mmol, 3.5 equiv.) in DCM (5 mL) was added compound 1-5 (0.226 g, 0.87 mmol, 1.1 equiv.) at 25° C. The mixture was stirred at 25° C. for 1 h, and then diluted with DCM (30 mL), washed with water (2*10 mL), dried over $Na_2SO_4$ and concentrated. The crude product was purified on silica gel column (DCM/MeOH=20:1) or purified by prep-HPLC ($MeCN/H_2O$=30:70, 0.1% of HCl as additive) to afford Compound 5 (0.18 g, 53% of yield) as white solid. $^1$H NMR (400 MHz, DMSO, HCl salt) δ 11.68 (s, 1H), 10.84 (s, 1H), 7.92 (t, J=6.2 Hz, 1H), 7.88 (s, 1H), 7.71 (t, J=8.5 Hz, 2H), 7.66-7.60 (m, 2H), 7.47 (d, J=8.2 Hz, 1H), 7.41 (dd, J=8.4, 1.5 Hz, 1H), 7.22 (t, J=7.5 Hz, 1H), 7.11 (t, J=7.4 Hz, 1H), 6.57 (s, 1H), 4.80 (q, J=6.3 Hz, 1H), 3.76 (s, 3H), 3.73-3.64 (m, 1H), 3.57 (dd, J=13.7, 6.8 Hz, 1H), 3.29 (dd, J=13.9, 7.1 Hz, 1H), 3.17 (td, J=10.4, 4.9 Hz, 1H), 2.96 (dq, J=17.0, 8.5 Hz, 2H), 1.94-1.65 (m, 4H). ESI-TOF m/z calcd. for $C_{23}H_{27}N_4O_2S^+$: 423.2, found 423.1.

Example 2: Preparation of (S)—N-(2-(1-methyl-1H-indol-3-yl)-2-(pyrrolidin-1-yl)ethyl)-1H-indole-6-sulfonamide (Compound 24) and (R)—N-(2-(1-methyl-1H-indol-3-yl)-2-(pyrrolidin-1-yl)ethyl)-1H-indole-6-sulfonamide (Compound 25)

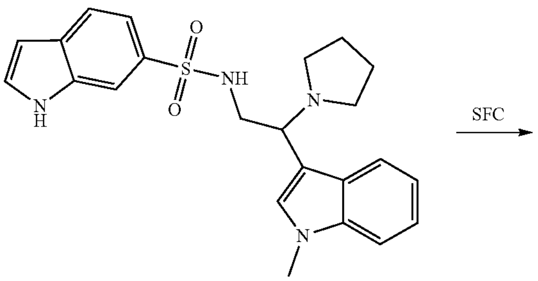

Compound 5

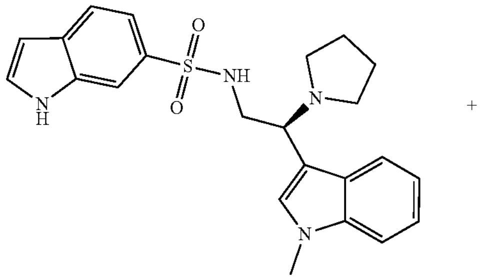

+

Compound 24

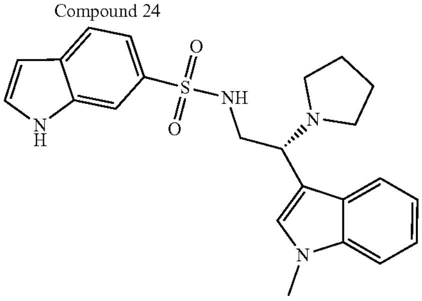

Compound 25

Compounds 24 and 25 were prepared by the chiral resolution of Compound 5 (180 mg) using the chiral prep-SFC method below:

| | |
|---|---|
| System | Waters SFC 80 |
| Column | DAICELCHIRALCEL ®IG<br>(250 x 25 mm x 10 μm) |
| Mobile Phase | A:B 60:40<br>A: Supercritical $CO_2$; food grade<br>B: EtOH(+N); food grade |
| Flow | 70 g/min |
| Column Temp | RT |
| Back Pressure | 100 bar |
| Injection | 1 mL |
| Cycle Time | 10 min |
| Wavelength Detection | 214 nm |
| Sample Preparation | Dissolved in ~20 mL EtOH |

Compound 24: 85 mg (47% of yield, >99.9% ee). $^1$H NMR (400 MHz, $CDCl_3$) δ 8.77 (s, 1H), 7.90 (s, 1H), 7.68 (d, J=8.3 Hz, 1H), 7.49 (d, J=8.3 Hz, 1H), 7.41 (s, 1H), 7.35 (d, J=7.9 Hz, 1H), 7.25-7.13 (m, 2H), 6.99 (t, J=7.3 Hz, 1H), 6.83 (s, 1H), 6.63 (s, 1H), 3.83 (t, J=6.7 Hz, 1H), 3.66 (s, 3H), 3.50-3.39 (m, 1H), 3.27 (dd, J=11.9, 6.6 Hz, 1H), 2.52-2.30 (m, 4H), 1.73-1.54 (m, 4H). ESI-TOF m/z calcd. for $C_{23}H_{27}N_4O_2S^+$: 423.2, found 423.1.

Compound 25: 78 mg (43% of yield, 96% ee). $^1$H NMR (400 MHz, $CDCl_3$) δ 8.59 (s, 1H), 7.86 (s, 1H), 7.69 (d, J=8.3 Hz, 1H), 7.49 (d, J=8.3 Hz, 1H), 7.41 (s, 1H), 7.34 (d, J=8.0 Hz, 1H), 7.25-7.15 (m, 2H), 6.98 (t, J=7.4 Hz, 1H), 6.80 (s, 1H), 6.64 (s, 1H), 3.76 (t, J=6.9 Hz, 1H), 3.67 (s, 3H), 3.46-3.33 (m, 1H), 3.25 (dd, J=11.8, 6.6 Hz, 1H), 2.46-2.26 (m, 4H), 1.69-1.54 (m, 4H). ESI-TOF m/z calcd. for $C_{23}H_{27}N_4O_2S^+$: 423.2, found 423.1.

The following compounds were synthesized using procedures analogous to those in Examples 1-2 using appropriate starting materials and reagents.

| Cmpd No. | $[M + H]^+$ |
|---|---|
| 1 | 425.2 |
| 2 | 411.16 |
| 3 | 384.32 |
| 4 | 409.15 |
| 6 | 398.18 |
| 7 | 398.15 |
| 8 | 411.22 |
| 10 | 396.87 |
| 11 | 415.11 |
| 12 | 352.1[a] |
| 13 | 352.1 |
| 14 | 352.2 |
| 15 | 384.14 |
| 17 | 395.21 |
| 18 | 427.25 |
| 19 | 398.20 |
| 20 | 415.25 |
| 21 | 411.20 |
| 22 | 383.20 |
| 23 | 426.21 |
| 26 | 423.1 |
| 27 | 423.1 |
| 28 | 423.1 |
| 29 | 437.5 |
| 30 | 439.2 |
| 31 | 465.2 |
| 32 | 427.1 |
| 33 | 437.2 |
| 35 | 480.2 |
| 36 | 441.4 |
| 37 | 411.5 |
| 38 | 425.6 |
| 39 | 452.2 |
| 40 | 453.1 |
| 42 | 431.23 |
| 43 | 439.1 |
| 44 | 439.1 |
| 45 | 441.2 |
| 46 | 482.2 |
| 47 | 467.1 |
| 48 | 437.1 |
| 49 | 446.5 |
| 50 | 459.1 |
| 51 | 445.1 |
| 52 | 451.1 |
| 53 | 437.1 |
| 54 | 424.5 |
| 55 | 437.1 |
| 57 | 395.25 |
| 58 | 499.2 |
| 59 | 499.2 |
| 60 | 499.1 |
| 61 | 499.2 |
| 62 | 480.1 |
| 63 | 411.5 |
| 64 | 437.2 |
| 65 | 411.5 |
| 66 | 424.1 |
| 67 | 424.1 |
| 69 | 480.25 |

-continued

| Cmpd No. | [M + H]$^+$ |
|---|---|
| 70 | 451.31[b] |
| 71 | 422.26 |
| 72 | 412.22 |
| 73 | 411.22 |
| 74 | 453.1 |
| 75 | 453.2 |
| 76 | 437.2 |
| 77 | 437.2 |
| 78 | 410.1 |
| 79 | 410.1 |
| 80 | 424.1 |
| 81 | 424.2 |
| 82 | 424.1 |
| 83 | 424.1 |
| 84 | 466.5 |
| 85 | 466.5 |
| 86 | 480.6 |
| 87 | 480.5 |
| 88 | 383.1 |
| 89 | 424.2 |
| 90 | 424.3 |
| 91 | 438.2 |
| 92 | 438.5 |
| 93 | 462.1 |
| 94 | 424.1 |
| 95 | 424.1 |
| 96 | 427.5 |
| 97 | 427.5 |
| 98 | 410.1 |
| 99 | 410.1 |
| 100 | 411.30 |
| 101 | 409.22 |
| 102 | 409.28 |
| 103 | 423.39 |

[a] $[M - (CH_3)_2N]^+$;
[b] $[M + e^-]^{-1}$

II: Biological Assays

Example A-1: Kinetic Turbidity Aggregation Assay of Recombinant cryAB(R120)

Recombinant cryAB(R120G) protein was diluted to 100 μM in assay buffer (50 mM Tris, 100 mM NaCl, 5 mM DTT, 0.01% Triton X-100, 0.05% PEG-8000). Compounds were dissolved in DMSO at 10 mM then typically diluted to 2.5 mM in DMSO and serially diluted 2-fold as necessary. To a 384-well black microplate in quadruplicate was added 81 μL assay buffer, followed by 15 μL protein solution, and 4 μL compound to give a final concentration of 15 μM cryAB (R120G) protein in 4% DMSO. The assay plate was incubated in a plate reader at 42° C. and read via absorbance at 550 nm every 3.5 minutes for 4 hours with orbital shaking in between reads. % inhibition of protein aggregation was measured at various concentrations of compound. N.D. is not determined.

Results for selected compounds at various concentrations are listed in the following table.

| | % Inhibition of Protein Aggregation | | |
|---|---|---|---|
| Cmpd No. | 400 μM cmpd | 100 μM cmpd | 25 μM cmpd |
| 1 | 96.6 | 99.5 | 84 |
| 2 | 95 | 99.4 | 88 |
| 3 | 99.12 | 83.7 | 58 |
| 4 | 91.84 | 62.8 | 66.7 |
| 5 | 97.9 | 99.8 | 99.6 |
| 6 | 18.8 | −38 | 19.5 |
| 7 | 56.6 | −32 | −21 |

-continued

| | % Inhibition of Protein Aggregation | | |
|---|---|---|---|
| Cmpd No. | 400 μM cmpd | 100 μM cmpd | 25 μM cmpd |
| 8 | 74.3 | −29 | −37 |
| 10 | 99.7 | 98.7 | 69.8 |
| 11 | 20.5 | −20 | −6 |
| 12 | 96.1 | 87.1 | 30 |
| 13 | 94.7 | 32.7 | −6 |
| 14 | 81 | 74.9 | 11 |
| 15 | 67.6 | 85.8 | 50 |
| 17 | 63.53 | −13 | −10.7 |
| 18 | 98.5 | 52.3 | 68 |
| 19 | 99.9 | 81.5 | 34 |
| 20 | 93.4 | 99.2 | 49 |
| 21 | 90.7 | 99.8 | 76 |
| 22 | 95.9 | 99 | 57 |
| 23 | 100.5 | 99 | 61 |
| 24 | N.D. | 99.89 | 99.7 |
| 25 | 97.25 | 97.14 | 39 |
| 26 | N.D. | 90.6 | −4 |
| 27 | N.D. | 85 | −35 |
| 28 | N.D. | 98.5 | 7 |
| 29 | N.D. | 99.9 | 69 |
| 30 | N.D. | 82 | −28 |
| 31 | N.D. | 70 | 23 |
| 32 | N.D. | 98.5 | 60 |
| 33 | N.D. | 82.8 | 27 |
| 35 | N.D. | 41.7 | −19 |
| 36 | N.D. | 83.9 | 99.7 |
| 37 | N.D. | 99.9 | 92.8 |
| 38 | N.D. | 99.8 | 57 |
| 39 | N.D. | 82.5 | 18 |
| 40 | N.D. | 79.7 | 16 |
| 42 | N.D. | 96.2 | 91 |
| 43 | N.D. | 98.6 | 20 |
| 44 | N.D. | 99.7 | 82 |
| 45 | N.D. | 69.3 | 95 |
| 46 | N.D. | 63.1 | −4 |
| 47 | N.D. | 86.9 | 32 |
| 48 | N.D. | 76.9 | 23 |
| 49 | N.D. | 99.2 | 47 |
| 50 | N.D. | 94.1 | 95 |
| 51 | N.D. | 80.4 | 46 |
| 52 | N.D. | 96.22 | 62 |
| 53 | N.D. | 99.9 | 99.6 |
| 54 | N.D. | 66 | −41 |
| 55 | N.D. | 99.6 | 33 |
| 57 | N.D. | 82.4 | 25 |
| 58 | N.D. | 66.7 | −8 |
| 59 | N.D. | 49.8 | 2 |
| 60 | N.D. | 94.9 | 57 |
| 61 | N.D. | 66.7 | 1 |
| 62 | N.D. | 53.1 | −39 |
| 63 | N.D. | 99.2 | 25 |
| 64 | N.D. | 95.4 | 9 |
| 65 | N.D. | 99.7 | 93 |
| 66 | N.D | 42 | −10 |
| 67 | N.D | 73.3 | 34 |
| 69 | N.D. | 100 | 58 |
| 70 | N.D. | 99.6 | 76 |
| 71 | N.D. | 99.3 | 63 |
| 72 | N.D. | 98.2 | 62 |
| 73 | N.D. | 99.5 | 57 |
| 74 | N.D. | 99.9 | 40 |
| 75 | N.D. | 99.2 | −10 |
| 76 | N.D. | 85.1 | 28 |
| 77 | N.D. | 100 | 88 |
| 78 | N.D. | 99.6 | 23 |
| 79 | N.D | 98.7 | 8 |
| 80 | N.D. | 95.1 | −28 |
| 81 | N.D. | 23 | −12 |
| 82 | N.D. | 38 | 16 |
| 83 | N.D. | 26 | 1 |
| 84 | N.D. | 71.8 | 25 |
| 85 | N.D. | 84.4 | 37 |
| 86 | N.D. | 94.1 | 80 |
| 87 | N.D. | 83.2 | 47 |
| 88 | N.D. | 94.3 | 21 |

-continued

| | % Inhibition of Protein Aggregation | | |
|---|---|---|---|
| Cmpd No. | 400 μM cmpd | 100 μM cmpd | 25 μM cmpd |
| 89 | N.D. | 99.7 | 98.4 |
| 90 | N.D. | 65.6 | −15 |
| 91 | N.D. | 99.6 | 99 |
| 92 | N.D. | 99.3 | 49 |
| 93 | N.D. | 94.3 | 99.7 |
| 94 | N.D. | 99.1 | 97.7 |
| 95 | N.D. | 56.2 | 14 |
| 96 | N.D. | 58.8 | 60 |
| 97 | N.D. | 58.8 | −45 |
| 98 | N.D. | 99.1 | 92.9 |
| 99 | N.D. | 21.3 | −56 |
| 100 | N.D. | 99.89 | 61.7 |
| 101 | N.D. | 97.6 | 63 |
| 102 | N.D. | 94.3 | 94 |
| 103 | N.D. | 99.7 | 59 |

$IC_{50}$ values for selected compounds are listed in the following table.

| Cmpd No. | $IC_{50}{}^{a}$ |
|---|---|
| 1 | A |
| 2 | A |
| 5 | A |
| 10 | B |
| 18 | B |
| 19 | B |
| 23 | B |
| 24 | A |
| 25 | B |
| 29 | B |
| 32 | B |
| 36 | A |
| 37 | A |
| 38 | B |
| 42 | A |
| 44 | A |
| 49 | B |
| 50 | A |
| 53 | A |
| 55 | C |
| 72 | B |
| 89 | A |
| 91 | A |
| 93 | A |

[a]A ≤ 10.0 μM < B ≤ 50.0 μM < C ≤ 100 μM

Example A-2: CryAB Binding Assay

Affinities were determined by MicroScale Thermophoresis using a direct binding assay. Briefly, the Alpha-Crystallin Domain of alpha B crystallin containing the E117C mutation was alkylated with a Cy5 dye and monitored for binding at 100 nM protein in Tris buffer pH 8, containing 0.1% PEG-8000, 0.05% Tween-20, and 5% DMSO. Binding assays were performed by titrating ligand against a mixture of the dye-labeled protein and monitoring fluorescence changes indicating binding. Based on observed fluorescence measurements for each compound titration a KD was calculated using the Law of Mass Action equation.

Results for selected compounds are listed in the following table.

| Cmpd No. | $K_d{}^{a}$ |
|---|---|
| 10 | B |
| 24 | A |
| 25 | B |
| 91 | A |
| 93 | A |

[a]A ≤ 10.0 μM < B ≤ 50.0 μM < C ≤ 100 μM

Example A-3: Treatment of Presbyopia

A group of 5 patients with presbyopia are identified based on impaired near visual acuity in the Log MAR test. The patients are treated weekly with a composition of a compound described herein. Every month each patient's near visual acuity is measured on the Log MAR test. Each patient's near visual acuity following treatment is compared to their pretreatment visual acuity.

Example A-4: Treatment of Loss of Near Vision Acuity

A group of 5 patients over the age of 40 years and without clinical signs of presbyopia are identified based on performance in the Log MAR test. The patients are treated with daily eyedrops containing composition of a compound described herein. Every 6 months each patient's near visual acuity is measured on the Log MAR test. Each patient's near visual acuity is compared to their pretreatment visual acuity.

What is claimed is:

1. A compound represented by the structure of Formula (IVa):

Formula (IVa)

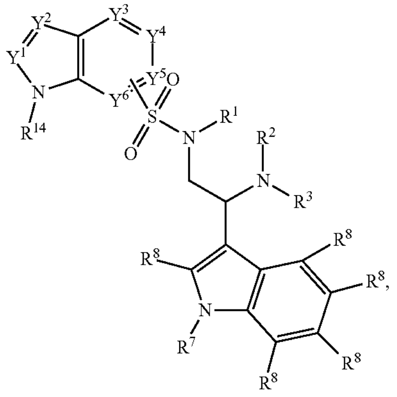

or a pharmaceutically acceptable salt thereof, wherein:

$Y^1$, $Y^2$, $Y^3$, $Y^4$, $Y^5$, and $Y^6$ are independently selected from $CR^{15}$ and N, wherein 0, 1, 2, or 3 of $Y^1$, $Y^2$, $Y^3$, $Y^4$, $Y^5$, and $Y^6$ are N; and wherein one of $Y^1$, $Y^2$, $Y^3$, $Y^4$, $Y^5$, and $Y^6$ is the attachment point to the rest of the molecule;

$R^{14}$ is selected from:

hydrogen;

$C_1$-$C_6$ alkyl which is optionally substituted with one or more substituents independently selected from $R^9$; and $C_3$-$C_6$ cycloalkyl and 3- to 6-membered heterocycloalkyl, each of which is optionally substituted with one or more substituents independently selected from $R^9$;

each $R^{15}$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$;

$R^1$ is selected from hydrogen; and $C_1$-$C_6$ alkyl, $C_2$-$C_6$ alkenyl, $C_2$-$C_6$ alkynyl, each of which is optionally substituted with one or more substituents independently selected from $R^9$;

$R^2$ and $R^3$ are independently selected from hydrogen; and $C_1$-$C_6$ alkyl, $C_2$-$C_6$ alkenyl, $C_2$-$C_6$ alkynyl, $C_3$-$C_6$ carbocycle, and 3- to 6-membered heterocycle, each of which is optionally substituted with one or more substituents independently selected from $R^9$;

or $R^1$ and $R^2$ are taken together with the intervening atoms to which they are attached to form a 5- to 8-membered heterocycle, which is optionally substituted with one or more substituents independently selected from $R^9$;

or $R^2$ and $R^3$ are taken together with the intervening atoms to which they are attached to form a 4- to 10-membered heterocycle, which is optionally substituted with one or more substituents independently selected from $R^9$;

$R^7$ is selected from:

hydrogen;

$C_1$-$C_6$ alkyl, $C_2$-$C_6$ alkenyl, and $C_2$-$C_6$ alkynyl, each of which is optionally substituted with one or more substituents independently selected from $R^9$; and $C_3$-$C_6$ cycloalkyl and 4-6-membered heterocycloalkyl, each of which is optionally substituted with one or more substituents independently selected from $R^9$; and each $R^8$ is independently selected from:

hydrogen, halogen, —CN, —OH, —$OR^{13}$, —$N(R^{12})_2$, —$C(=O)R^{12}$, —$C(=O)OR^{12}$, —$C(=O)N(R^{12})_2$, —$NR^{12}C(=O)R^{12}$, —$NR^{12}C(=O)N(R^{12})_2$, —$SR^{12}$, —$S(=O)R^{13}$, —$SO_2R^{13}$, —$SO_2N(R^{12})_2$, and —$NO_2$;

$C_1$-$C_6$ alkyl, $C_2$-$C_6$ alkenyl, and $C_2$-$C_6$ alkynyl, each of which is optionally substituted with one or more substituents independently selected from $R^9$;

$C_3$-$C_6$ cycloalkyl and 4-6-membered heterocycloalkyl, each of which is optionally substituted with one or more substituents independently selected from $R^9$;

each $R^9$ is independently selected from halogen, =O, =S, —CN, —OH, —$OR^{13}$, —$N(R^{12})_2$, —$C(=O)R^{12}$, —$C(=O)OR^{12}$, —$OC(=O)R^{12}$, —$C(=O)N(R^{12})_2$, —$NR^{12}C(=O)R^{12}$, —$NR^{12}C(=O)N(R^{12})_2$, —$OC(=O)N(R^{12})_2$, —$NR^{12}C(=O)OR^{12}$, —$OC(=O)OR^{12}$, —$SR^{12}$, —$S(=O)R^{13}$, —$SO_2R^{13}$, —$SO_2N(R^{12})_2$, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ hydroxyalkyl, $C_1$-$C_6$ aminoalkyl, $C_3$-$C_6$ carbocycle, and 3- to 6-membered heterocycle;

each $R^{12}$ is independently selected from hydrogen, $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle; and each $R^{13}$ is independently selected from $C_1$-$C_6$ alkyl, $C_2$-$C_6$ alkenyl, $C_2$-$C_6$ alkynyl, $C_1$-$C_6$ haloalkyl, $C_3$-$C_6$ carbocycle, and 3- to 6-membered heterocycle.

2. The compound or salt of claim 1, wherein the compound of Formula (IVa) is represented by Formula (IVb):

Formula (IVb)

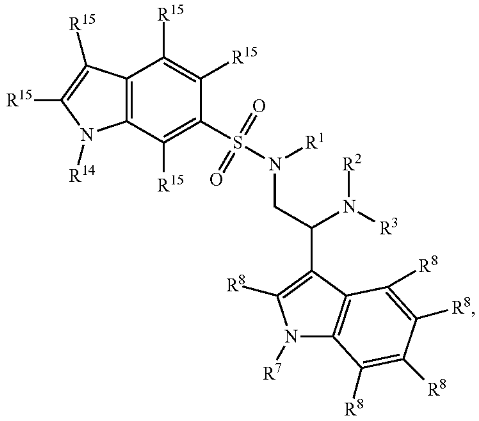

or a pharmaceutically acceptable salt thereof.

3. The compound or salt of claim 1, wherein $R^7$ is selected from:

hydrogen; and $C_1$-$C_6$ alkyl which is optionally substituted with one or more substituents independently selected from $R^9$.

4. The compound or salt of claim 3, wherein $R^7$ is selected from hydrogen and methyl.

5. The compound or salt of claim 1, wherein each $R^8$ is independently selected from:

hydrogen, halogen, —CN, and —$OR^{13}$; and $C_1$-$C_6$ alkyl which is optionally substituted with one or more substituents independently selected from $R^9$.

6. The compound or salt of claim 1, wherein each $R^{15}$ is independently selected from hydrogen, halogen, —CN, —OH, —$OR^{13}$, —$N(R^{12})_2$, $C_1$-$C_6$ alkyl, and $C_1$-$C_6$ fluoroalkyl.

7. The compound or salt of claim 1, wherein $R^{14}$ is selected from:

hydrogen; and $C_1$-$C_3$ alkyl which is optionally substituted with one or more substituents independently selected from $R^9$.

8. The compound or salt of claim 7, wherein $R^{14}$ is selected from hydrogen and methyl.

9. The compound or salt of claim 8, wherein $R^{14}$ is hydrogen.

10. A compound selected from:

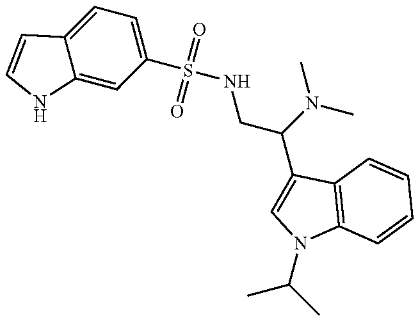
,

-continued
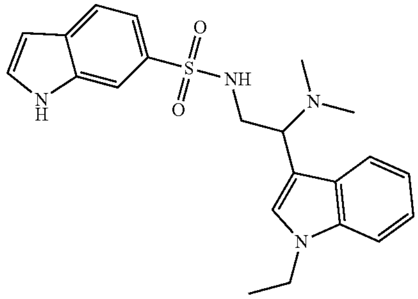
,
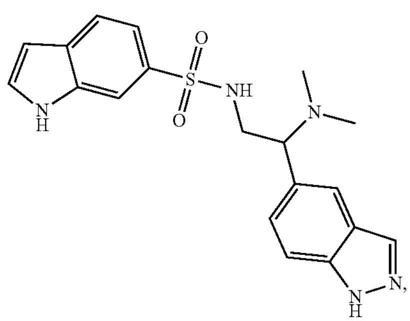
,
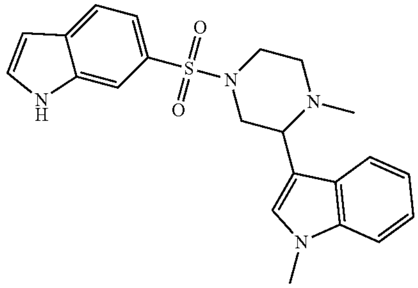
,
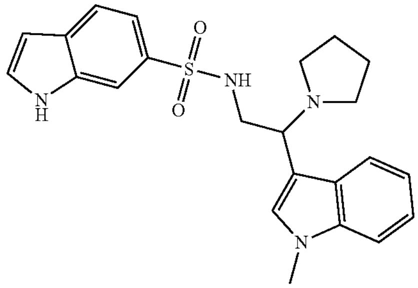
,
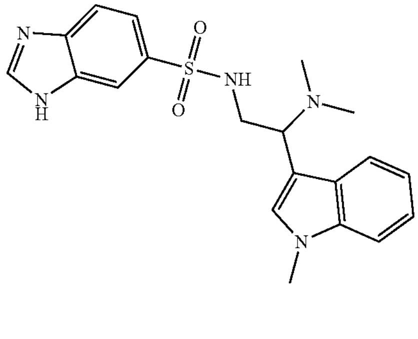
,
-continued
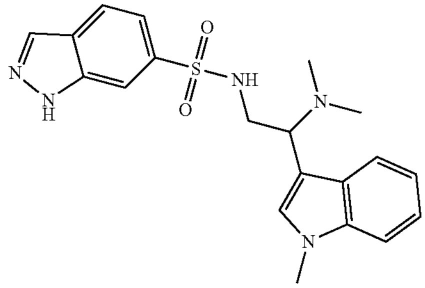
,
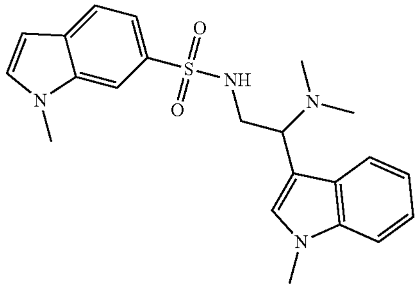
,
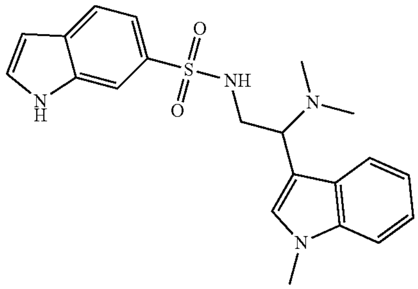
,
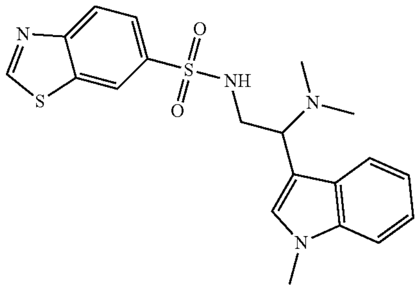
,
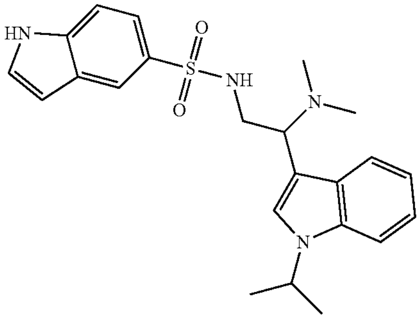
, -continued
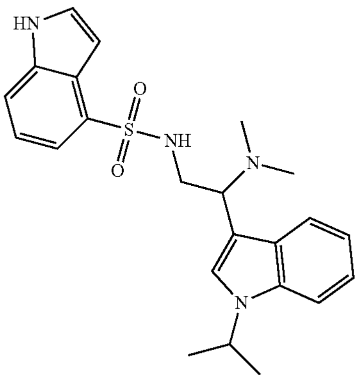
,
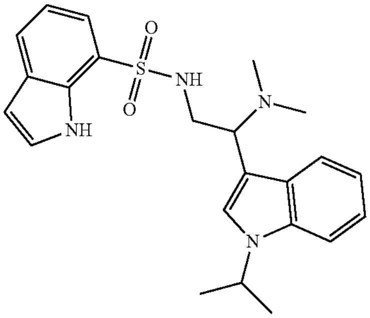
,
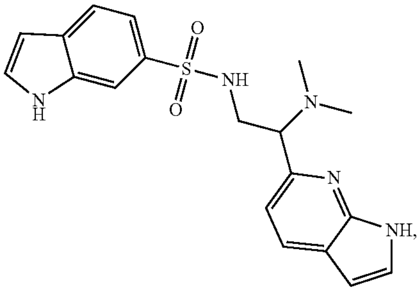
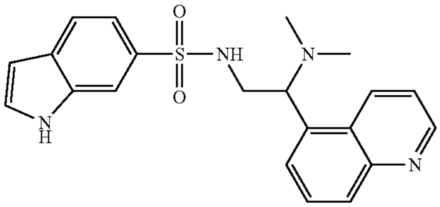
,
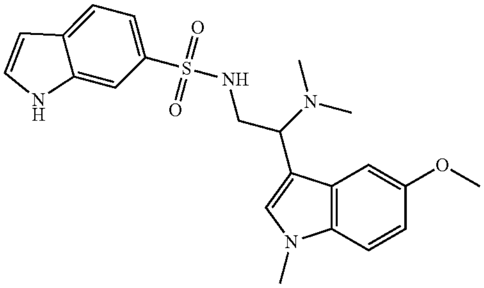
,
-continued
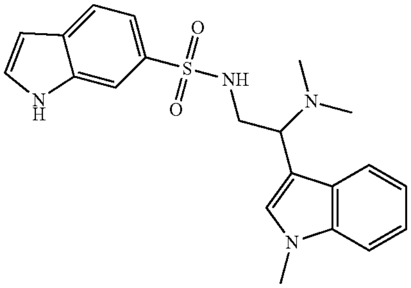
,
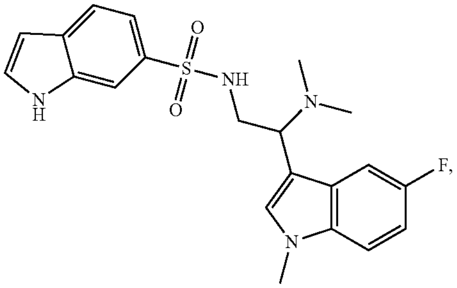
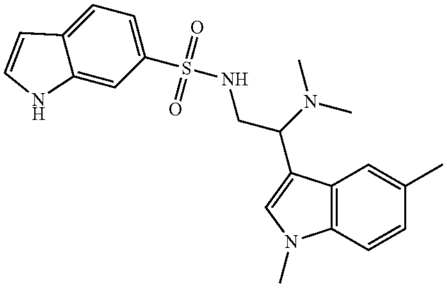
,
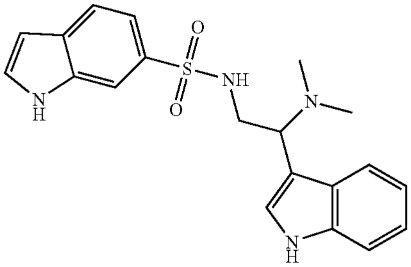
,
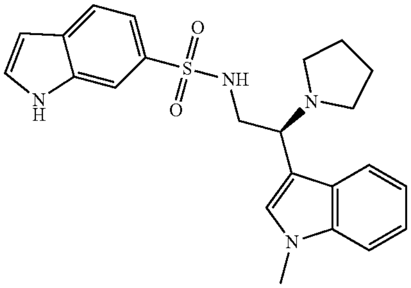
,
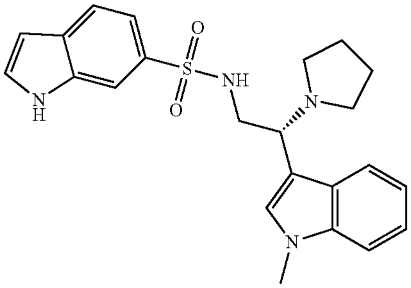
, -continued
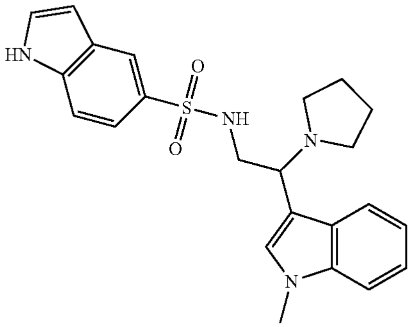
,
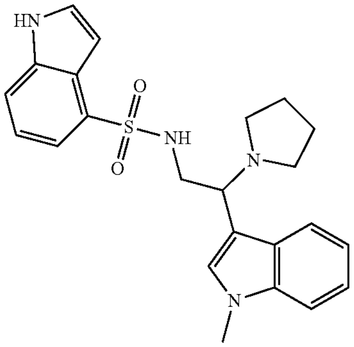
,
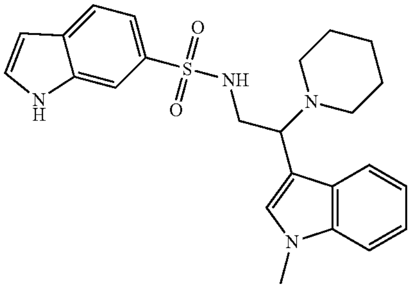
,
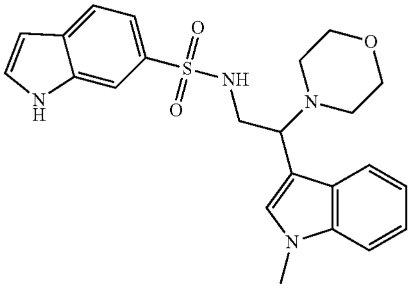
,
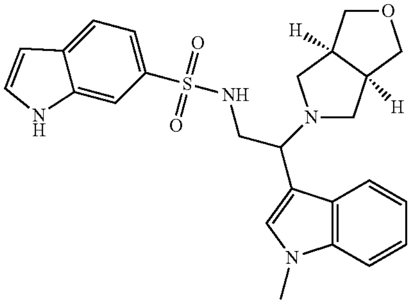
,
-continued
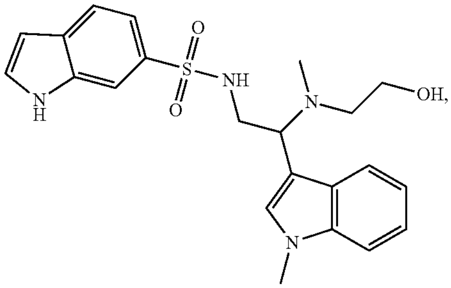
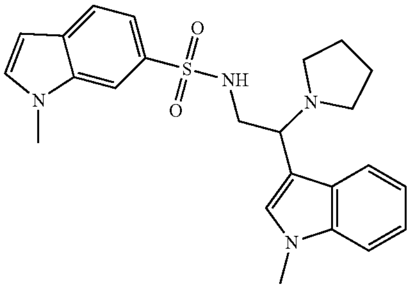
,
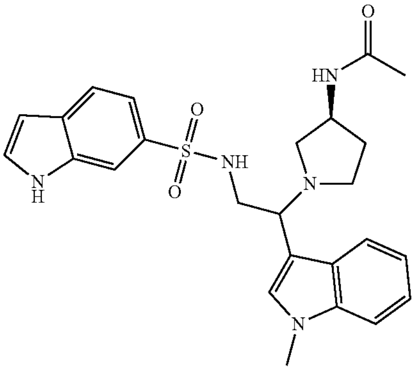
,
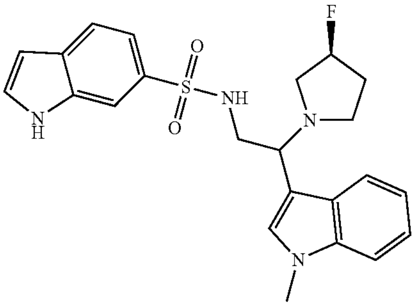
,
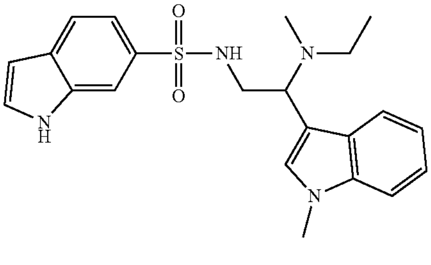
, -continued
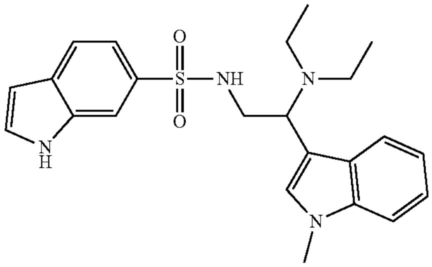
,
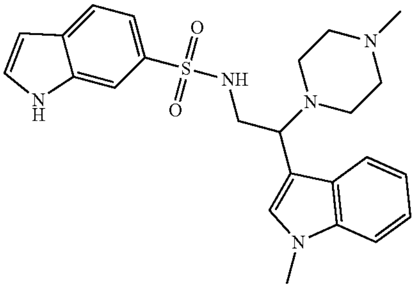
,
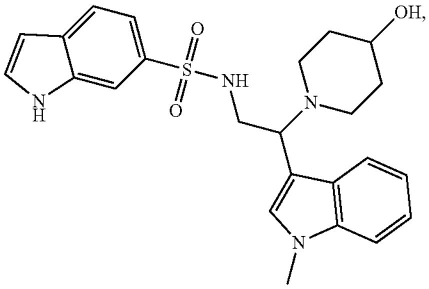
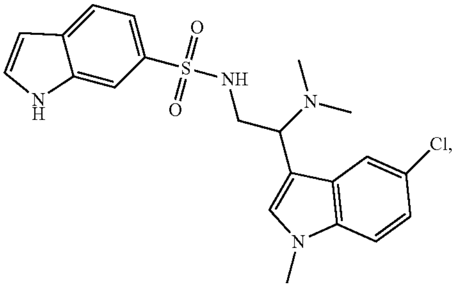
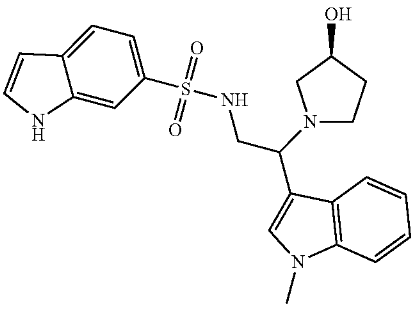
,
-continued
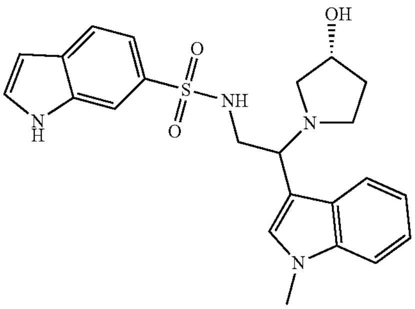
,
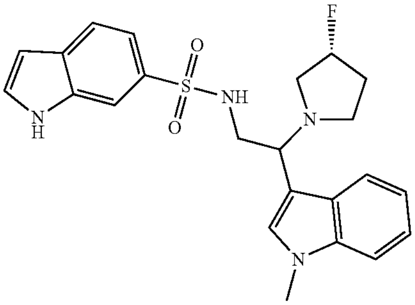
,
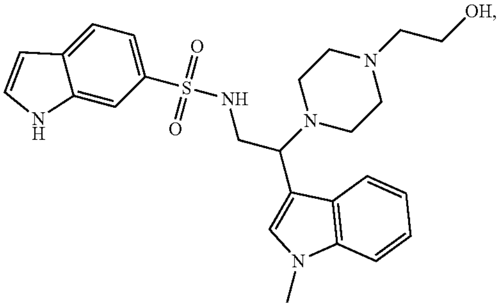
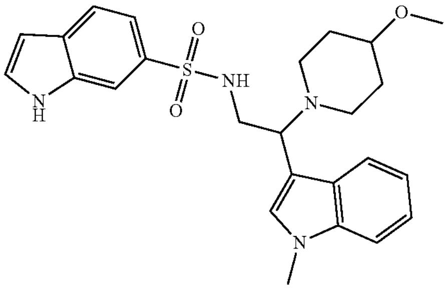
,
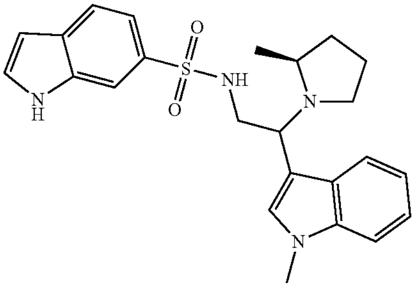
, -continued
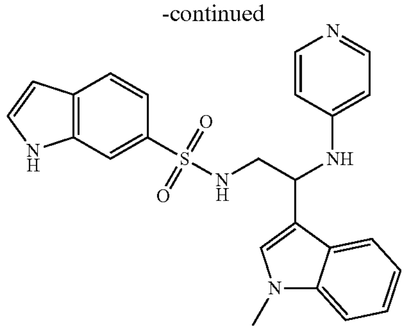
,
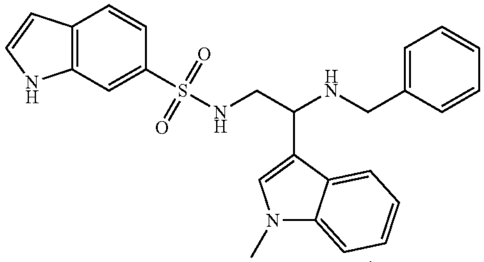
,
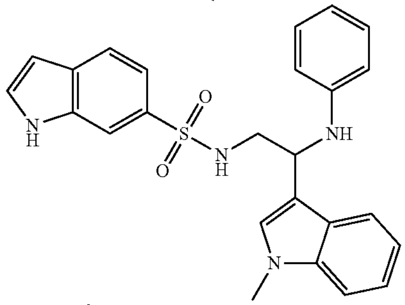
,
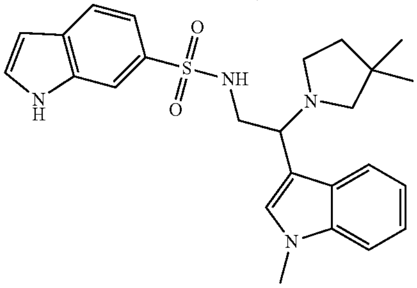
,
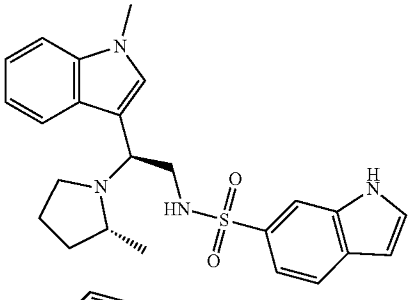
,
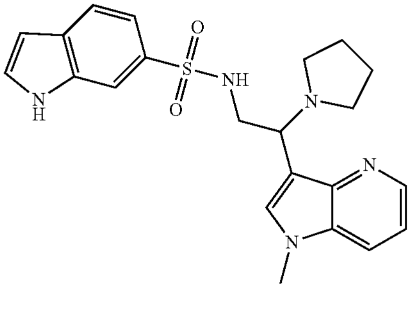
,
-continued
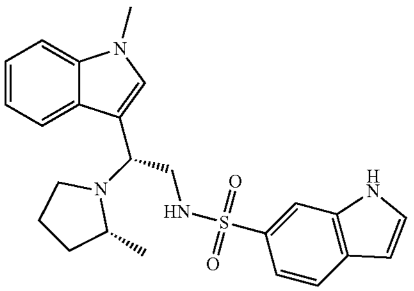
,
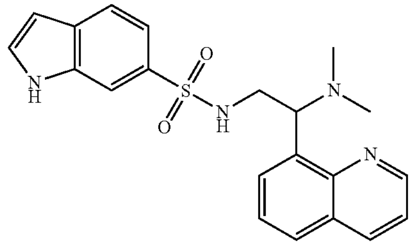
,
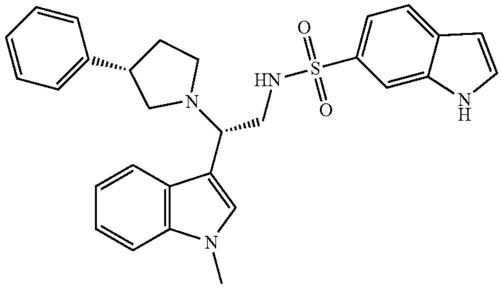
,
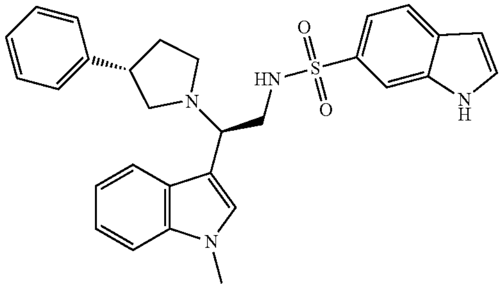
,
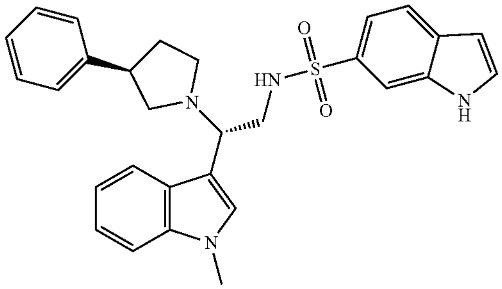
,
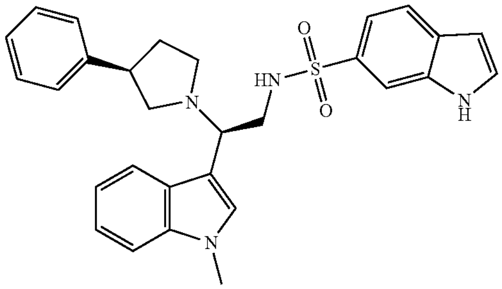
, -continued
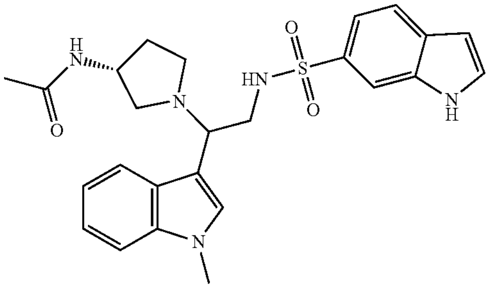
,
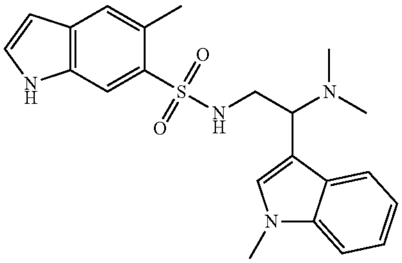
,
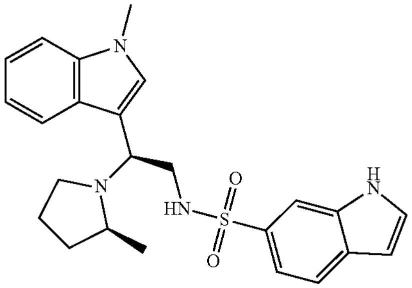
,
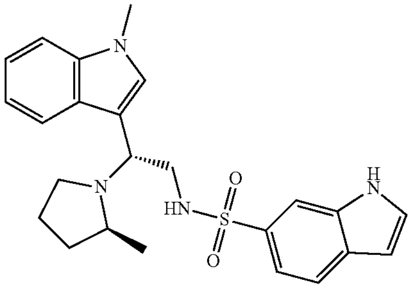
,
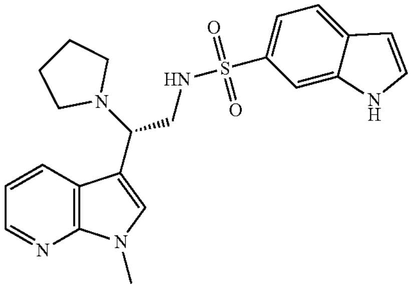
,
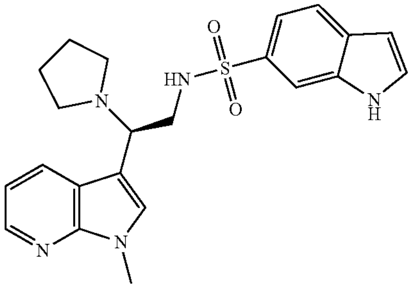
,
-continued
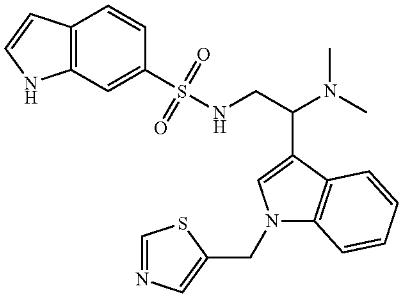
,
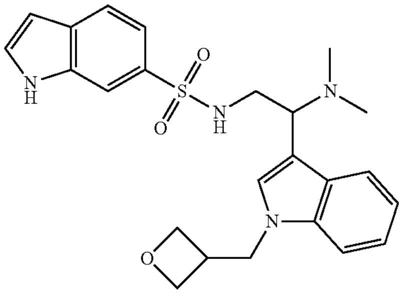
,
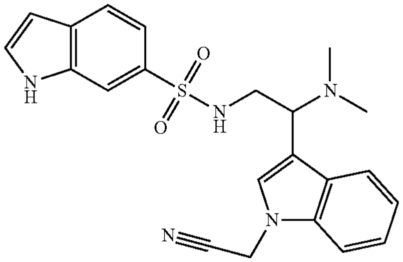
,
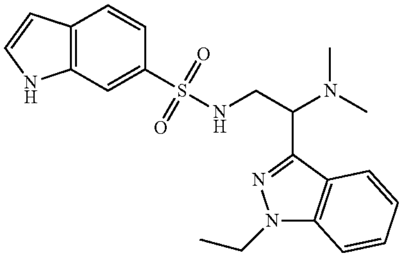
,
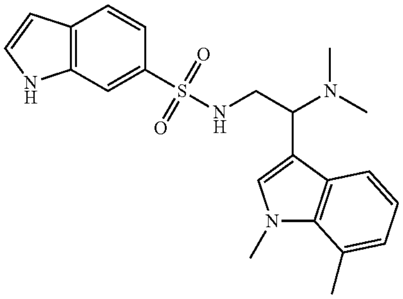
,
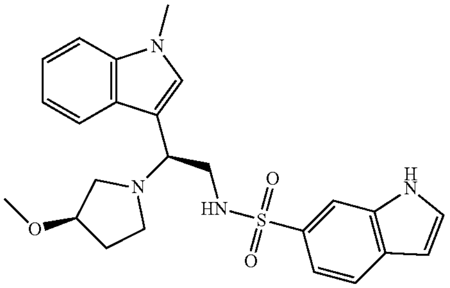
, -continued
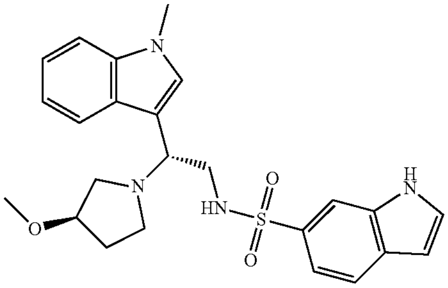
,
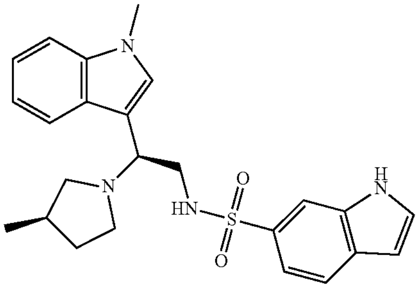
,
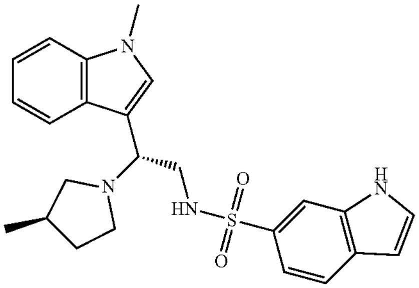
,
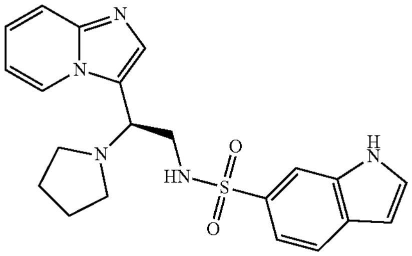
,
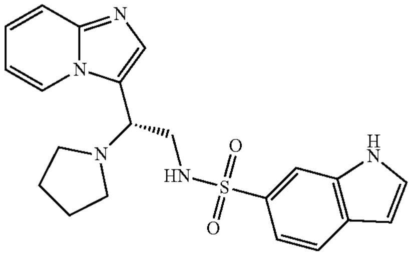
,
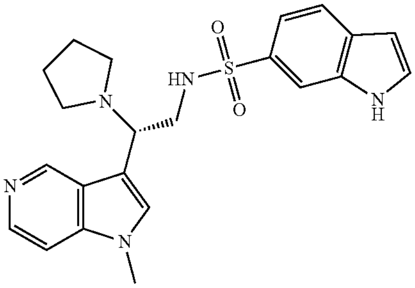
,
-continued
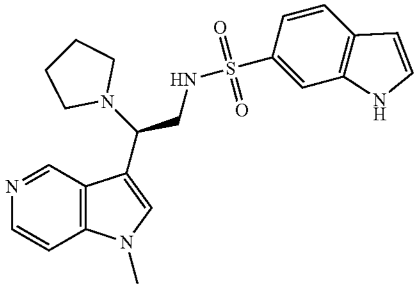
,
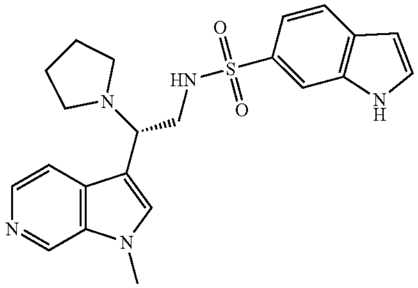
,
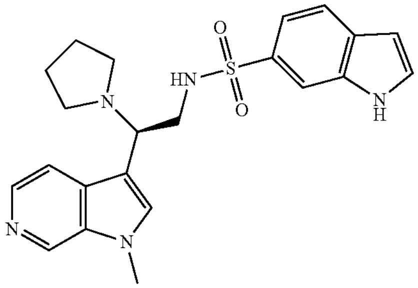
,
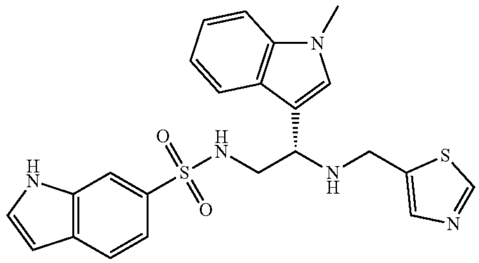
,
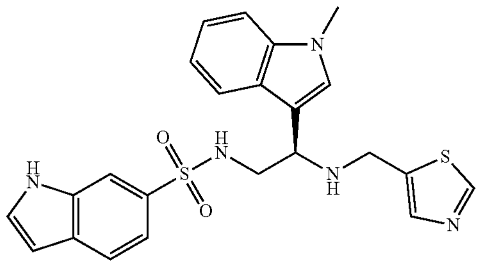
,
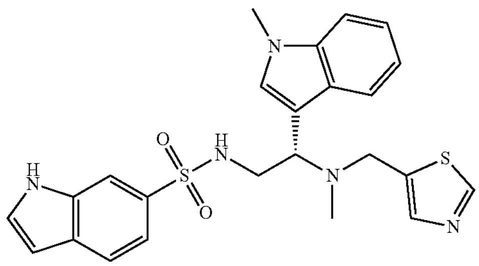
, -continued
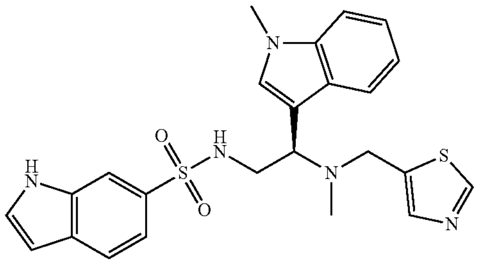
,
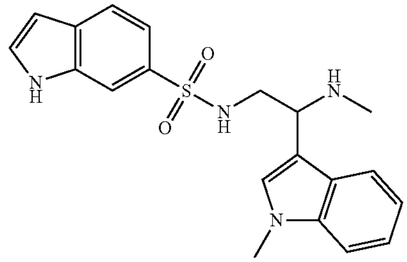
,
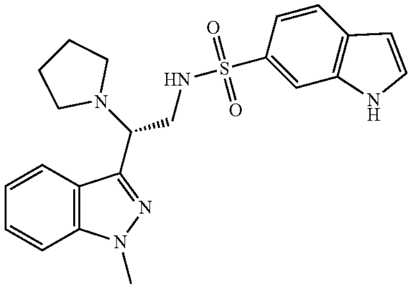
,
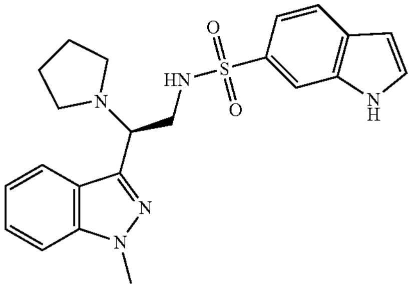
,
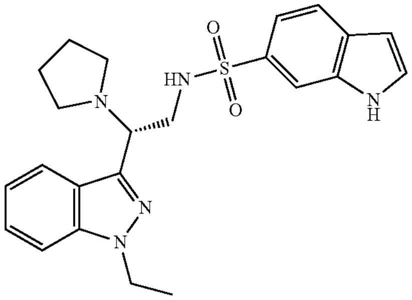
,
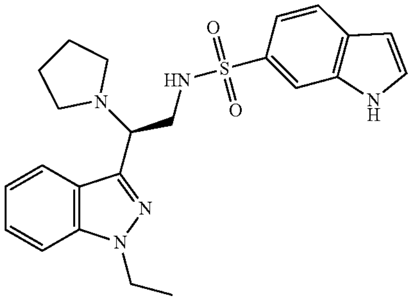
,
-continued
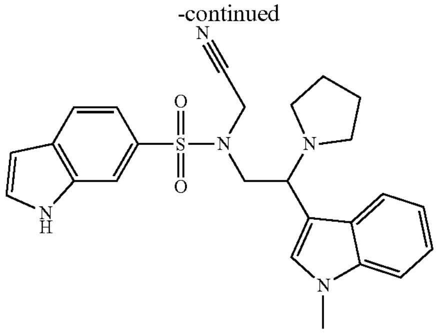
,
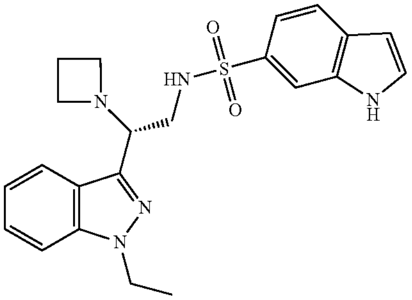
,
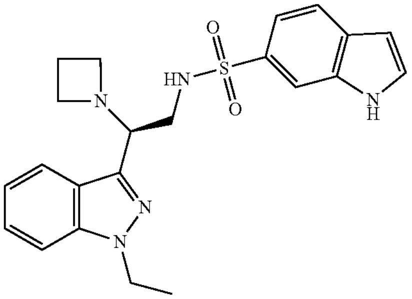
,
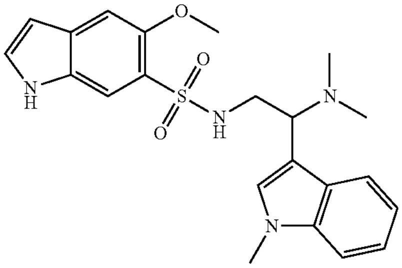
,
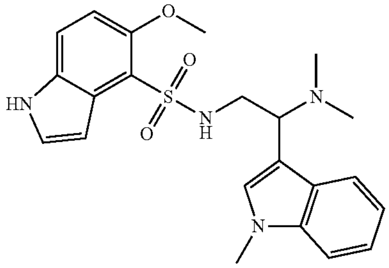
,
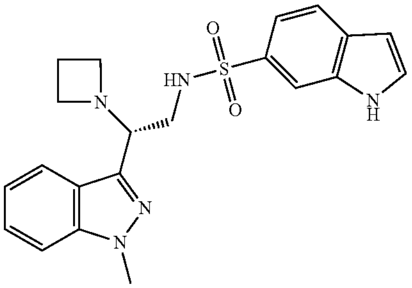
, -continued
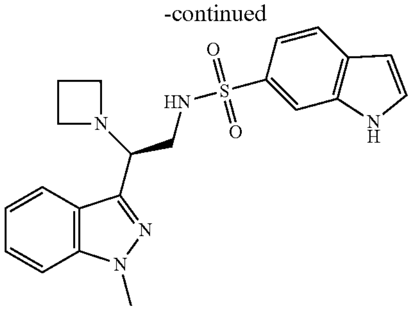
,
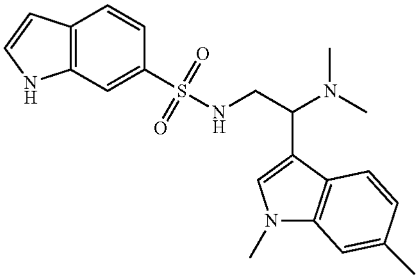
,
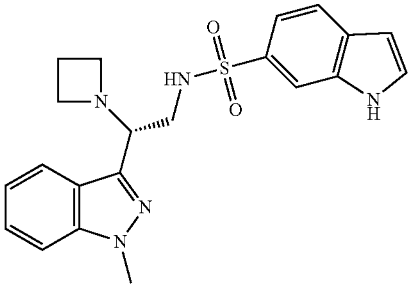
,
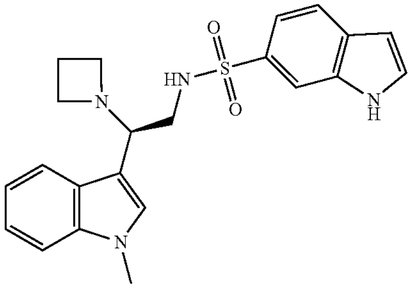
, and
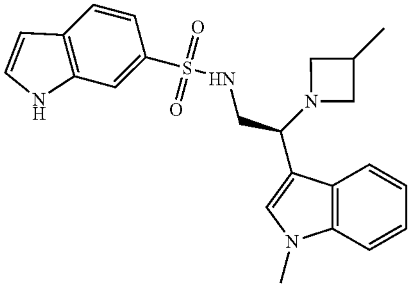
;
or a pharmaceutically acceptable salt thereof.
11. The compound or salt of claim 10, wherein the compound is selected from:
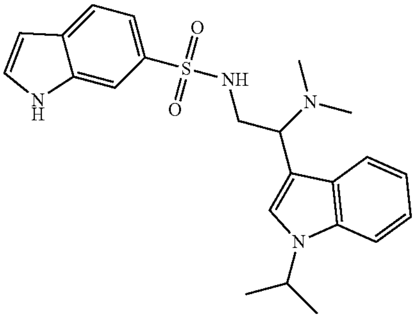
,
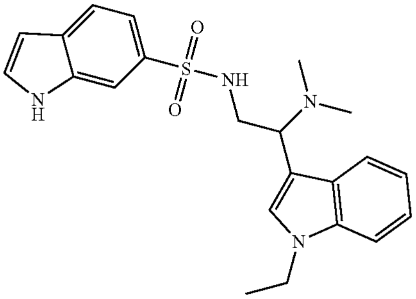
,
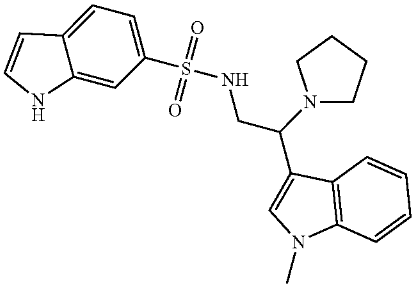
,
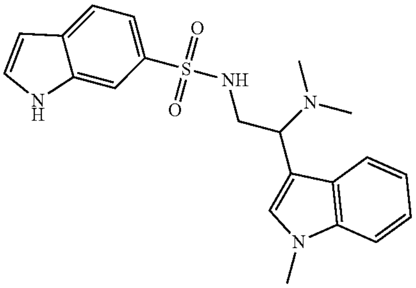
,
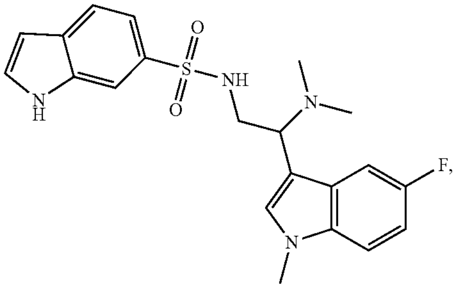
, -continued
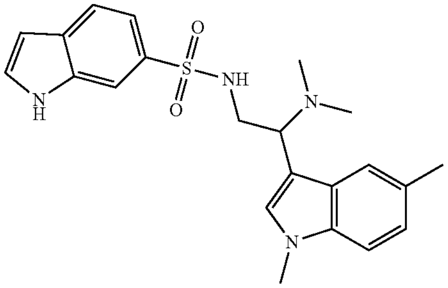
,
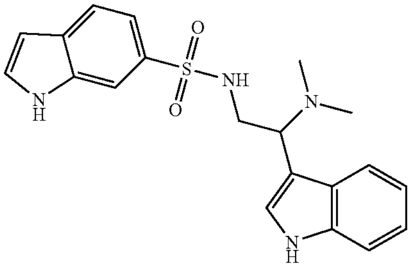
,
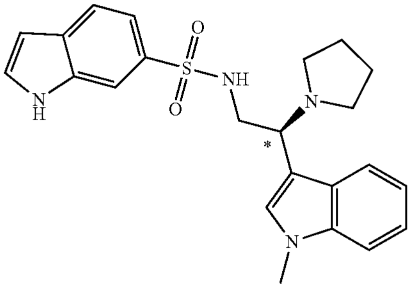
,
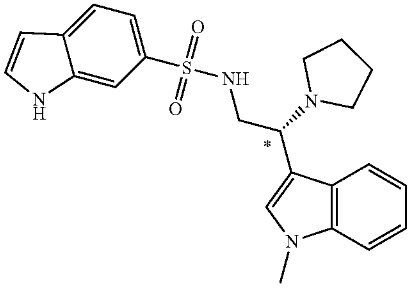
,
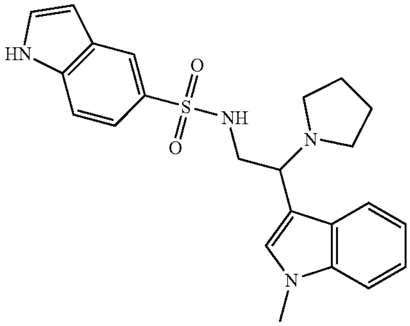
,
-continued
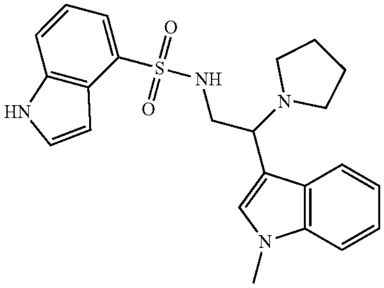
,
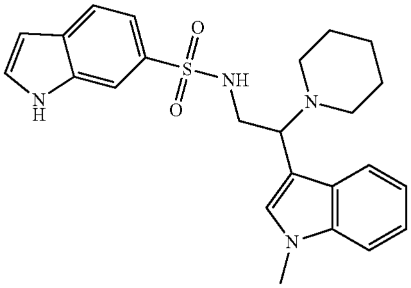
,
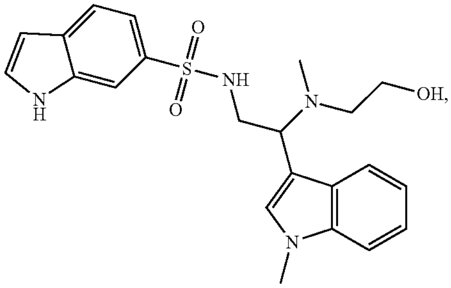
,
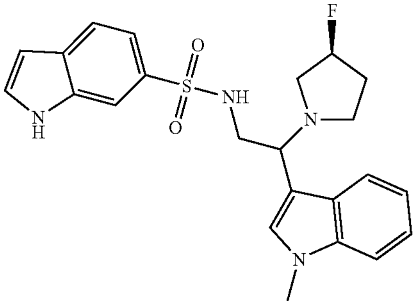
,
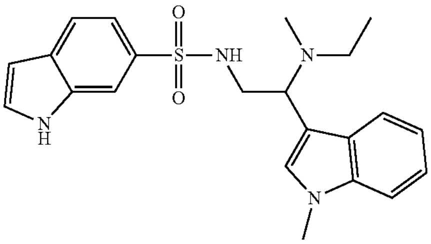
,
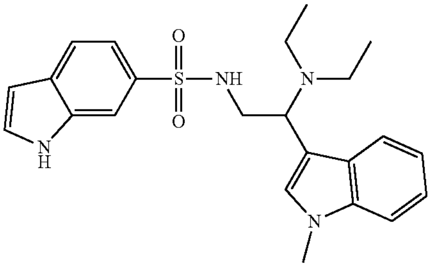
, -continued
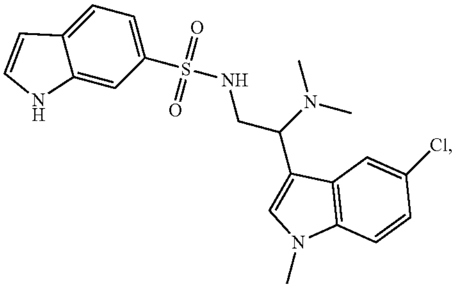
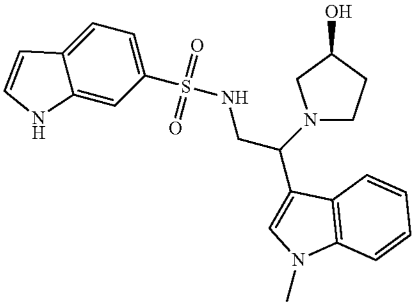
,
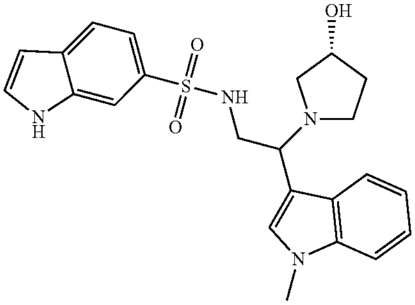
,
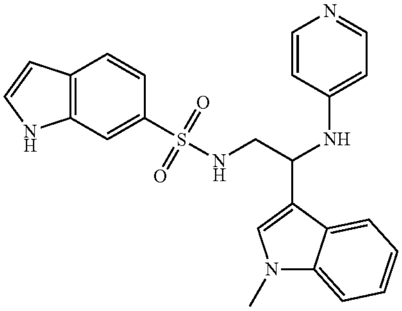
,
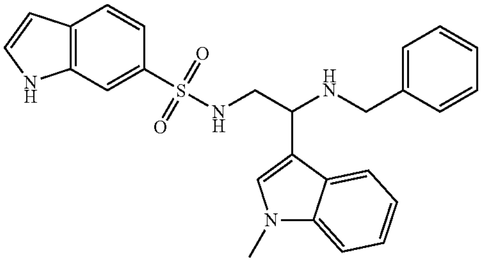
,
-continued
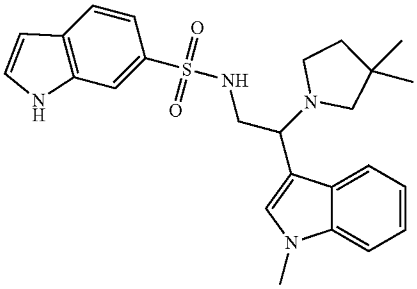
,
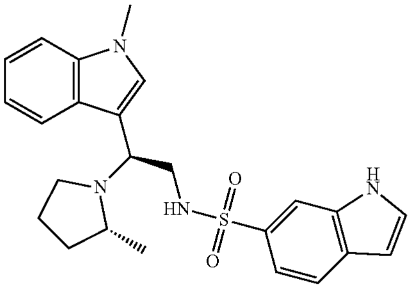
,
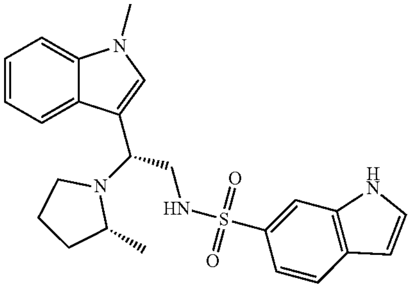
,
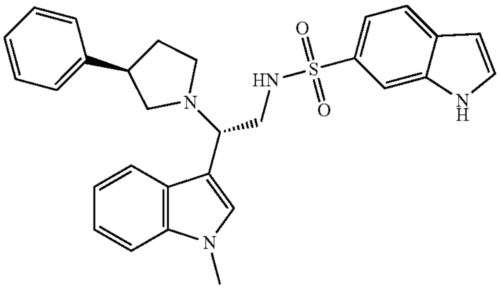
,
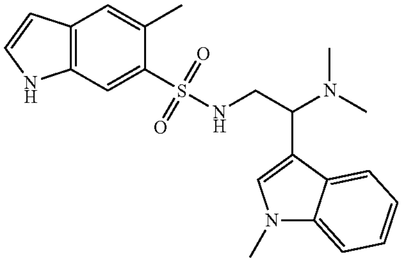
,
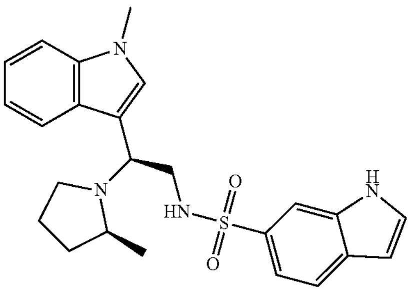
, -continued
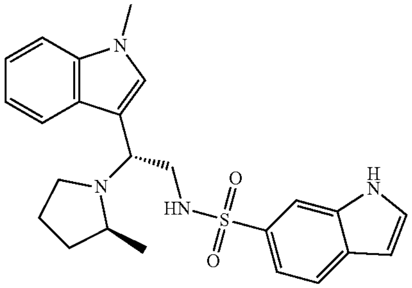
,
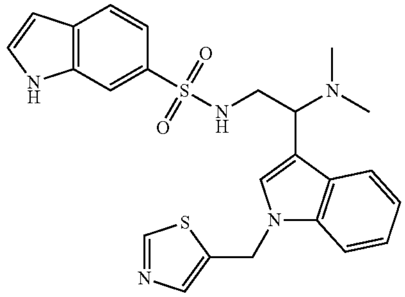
,
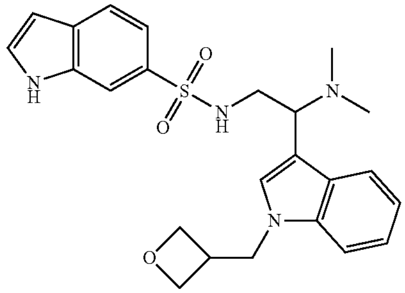
,
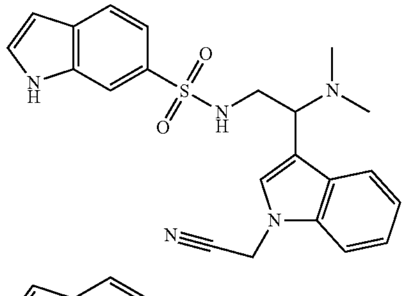
,
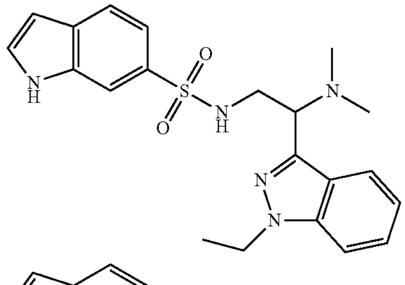
,
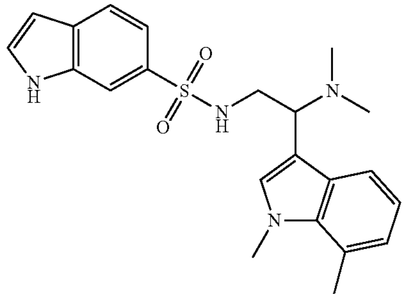
,
-continued
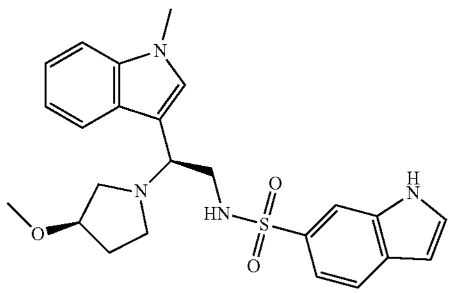
,
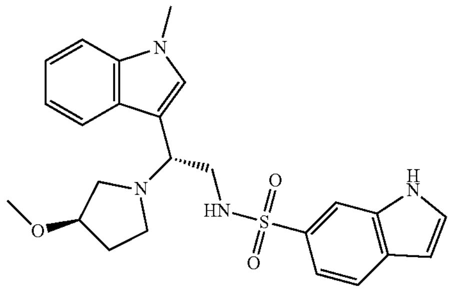
,
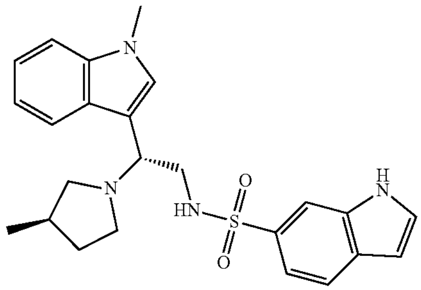
,
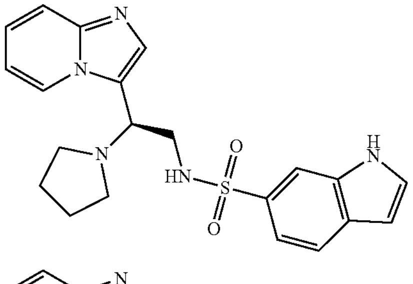
,
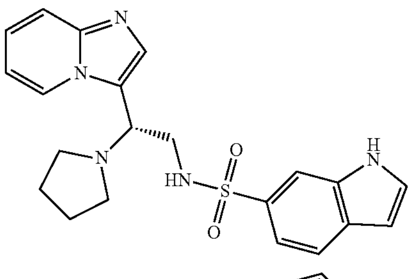
,
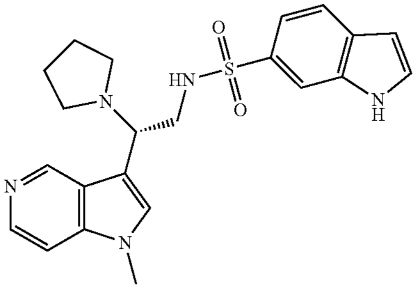
, -continued
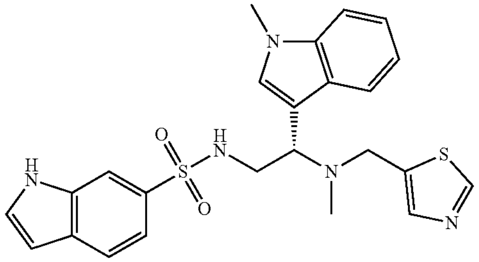
,
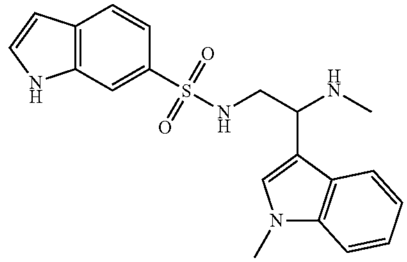
,
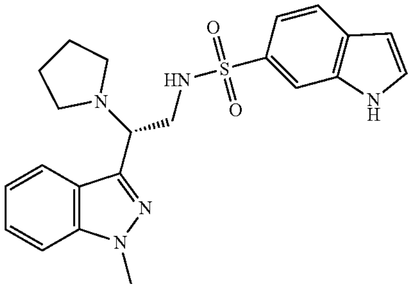
,
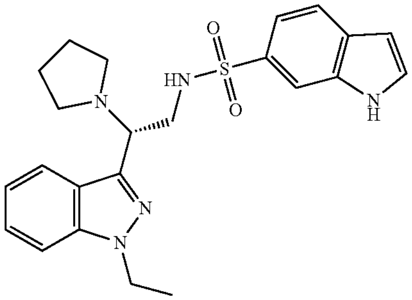
,
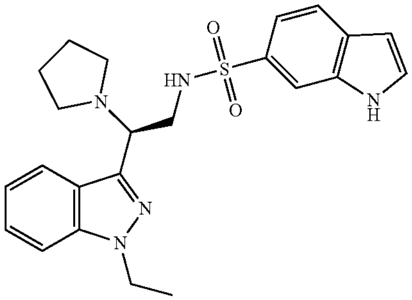
,
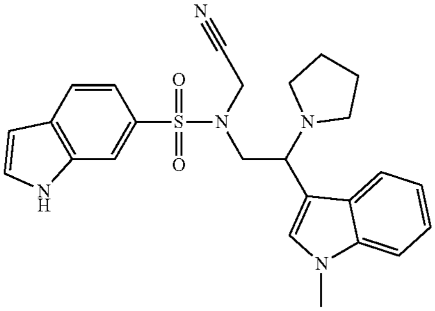
,
-continued
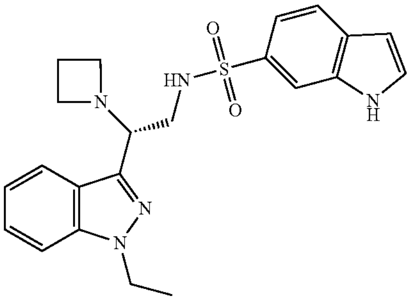
,
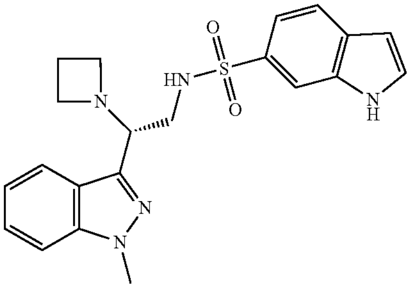
,
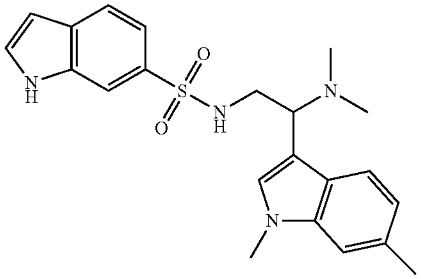
,
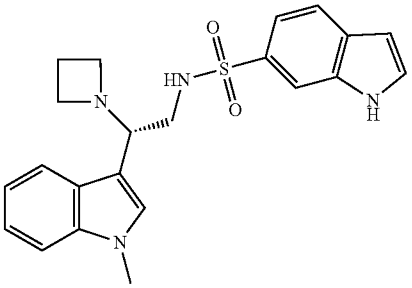
,
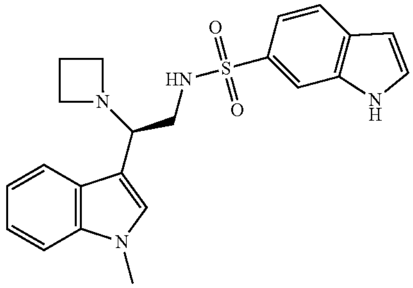
, and

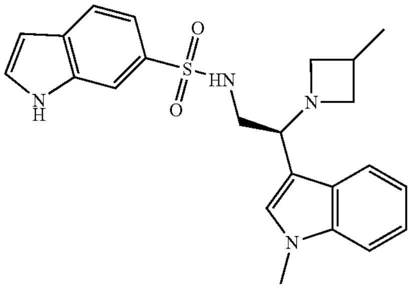
;
or a pharmaceutically acceptable salt thereof.
12. The compound or salt of claim 10, wherein the compound is selected from:
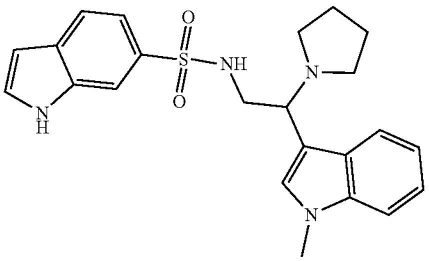
,
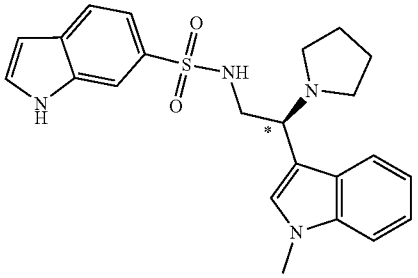
,
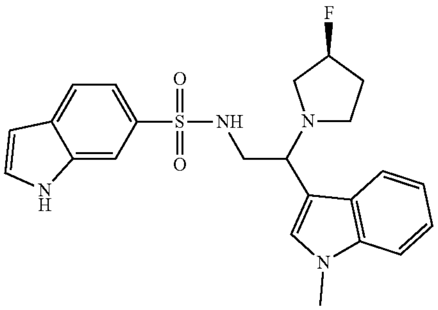
,
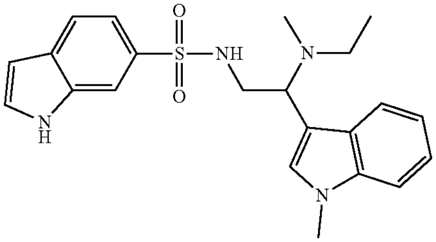
,
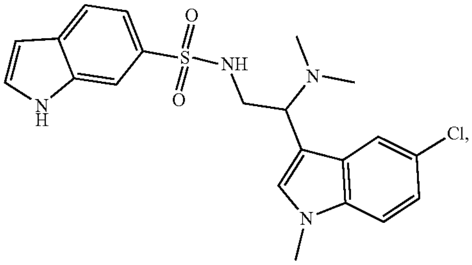
,
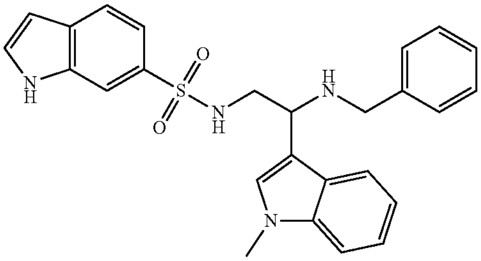
,
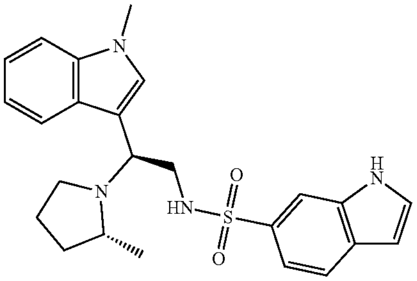
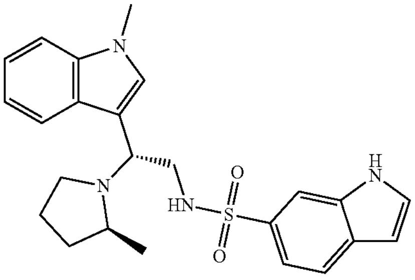
,
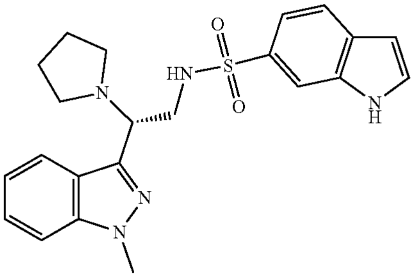
,
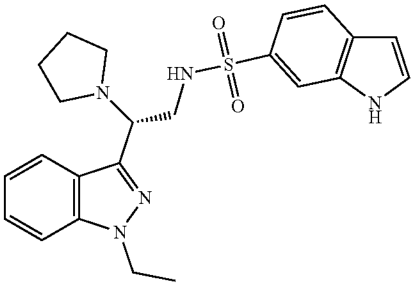
, -continued
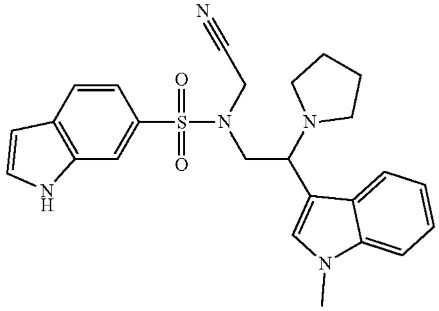
,
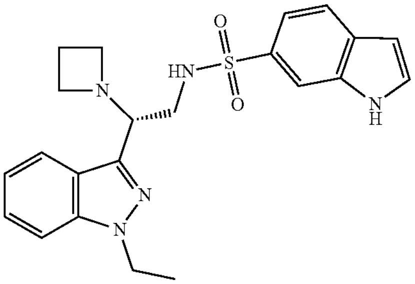
,
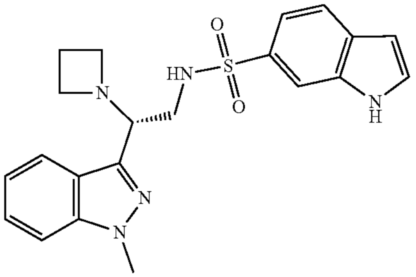
, and
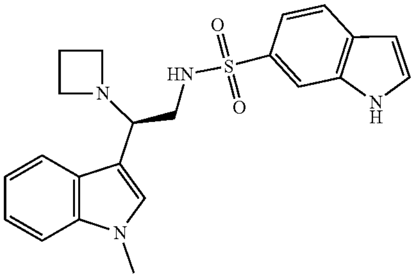
;
or a pharmaceutically acceptable salt thereof.
13. The compound or salt of claim 10, wherein the compound is selected from:
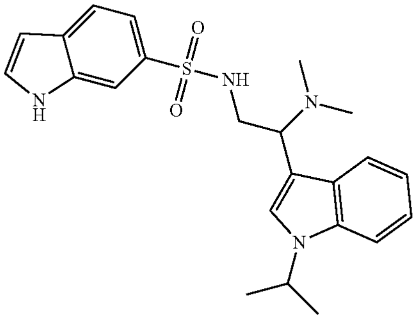
,
-continued
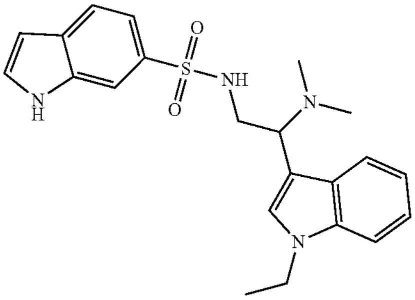
,
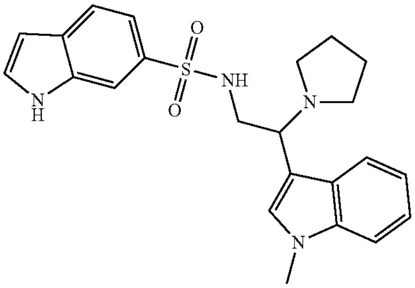
,
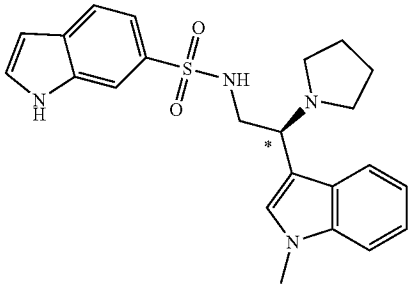
,
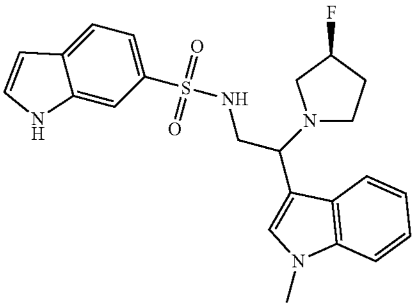
,
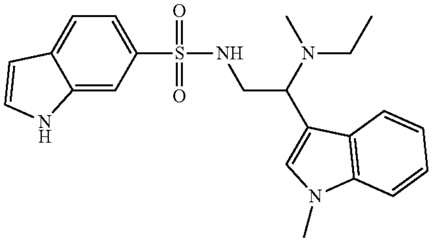
,
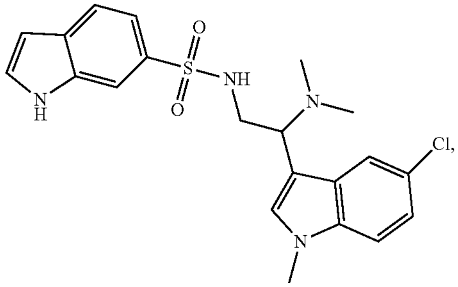
, -continued

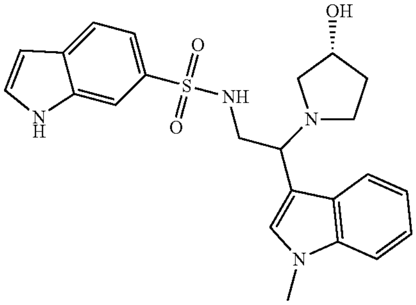

,

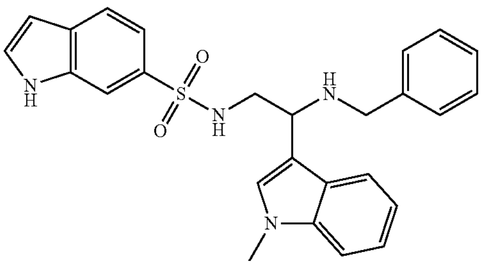

,

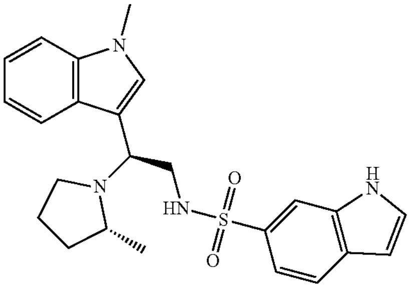

,

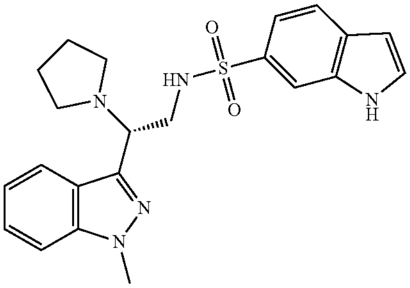

,

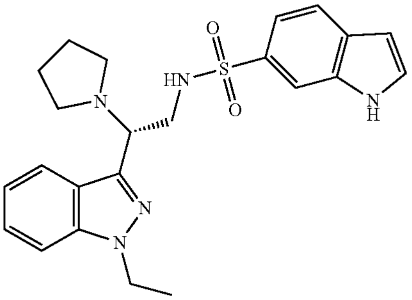

, and

-continued

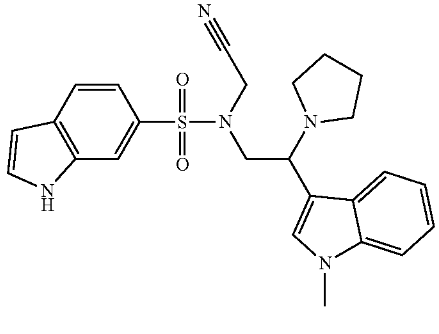

;

or a pharmaceutically acceptable salt thereof.

14. A pharmaceutical composition comprising a compound of claim 1, or a pharmaceutically acceptable salt thereof, and a pharmaceutically acceptable excipient.

15. A method for treating or preventing an ophthalmic disease in a subject, the method comprising administering to the eye of a subject in need thereof a compound of claim 1, or a pharmaceutically acceptable salt thereof.

16. The method of claim 15, wherein the ophthalmic disease is a near vision disorder.

17. The method of claim 16, wherein the near vision disorder is cataract or presbyopia.

18. A method of reducing aggregation of an α-crystallin protein by at least 5% in a subject in need thereof, the method comprising administering to the subject in need thereof an effective amount of a compound of claim 1, or a pharmaceutically acceptable salt thereof.

19. The method of claim 18, wherein aggregation of an a-crystallin protein is reduced by at least 10%.

20. The compound of claim 1, wherein the compound is selected from:

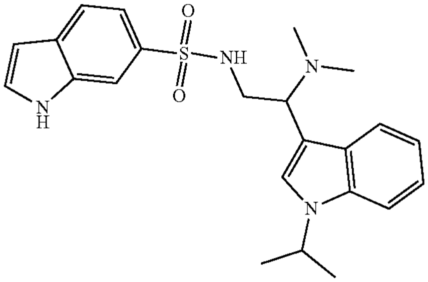

,

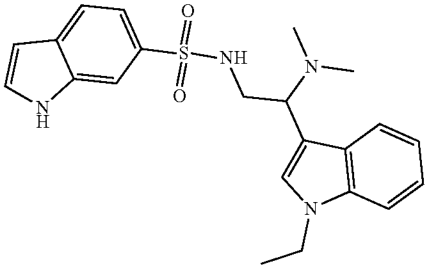

,

-continued
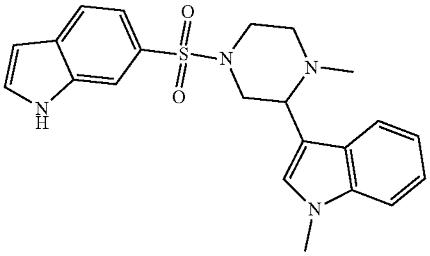
,
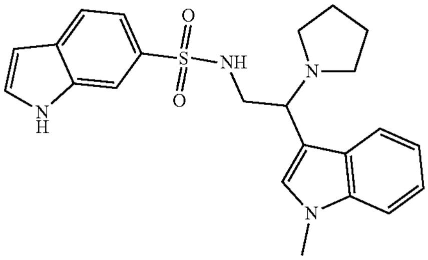
,
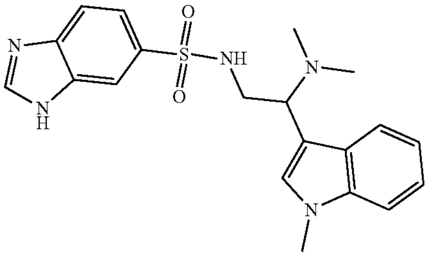
,
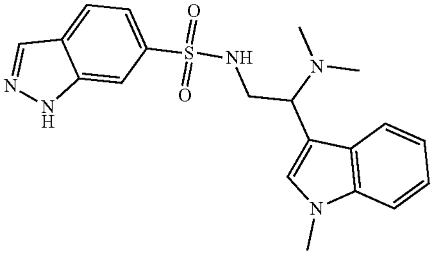
,
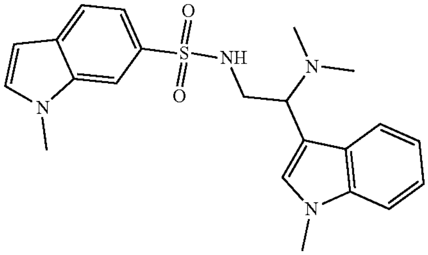
,
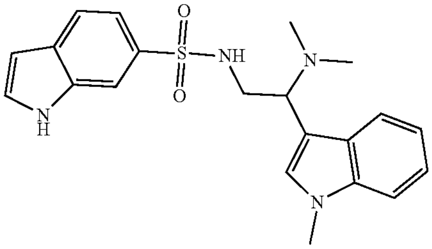
,
-continued
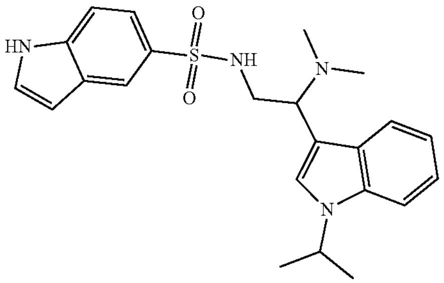
,
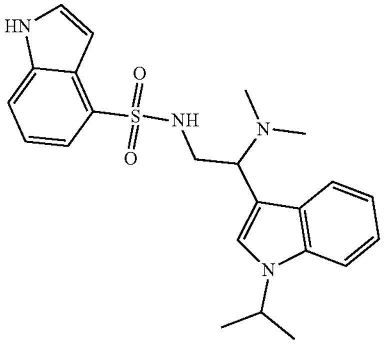
,
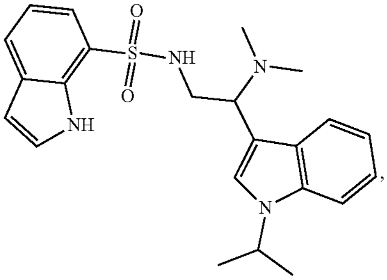
,
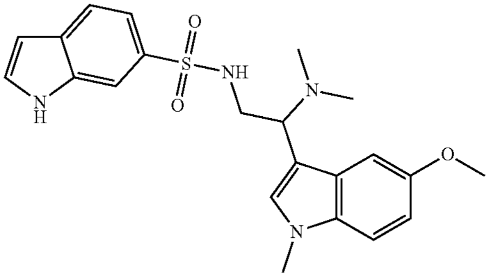
,
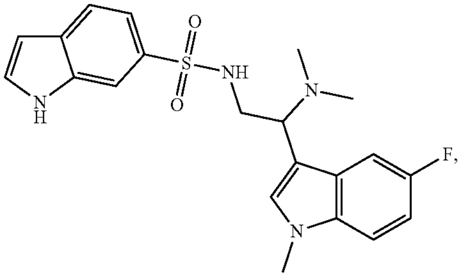
, -continued
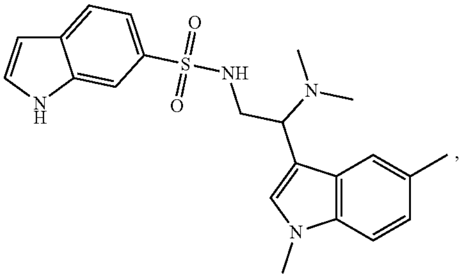
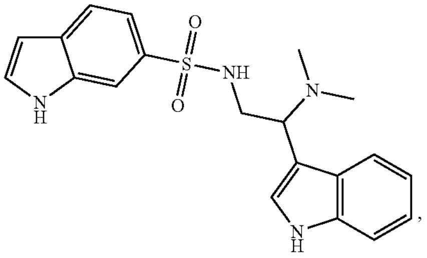
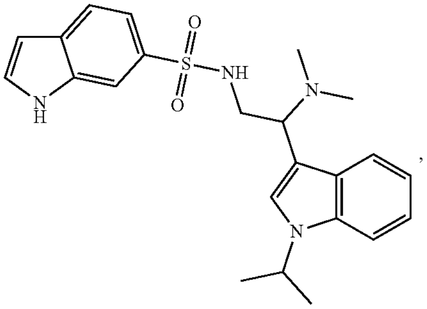
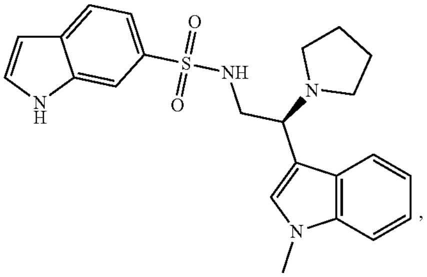
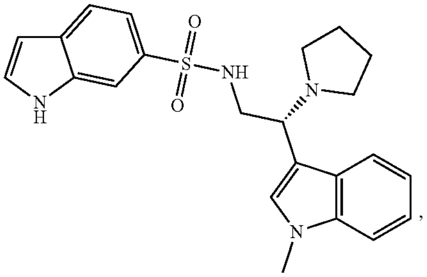
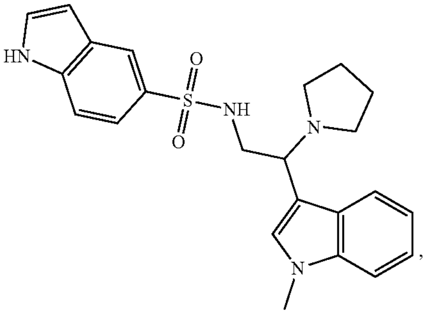
-continued
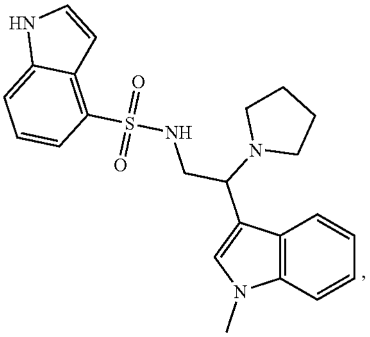
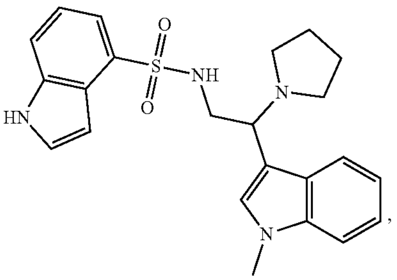
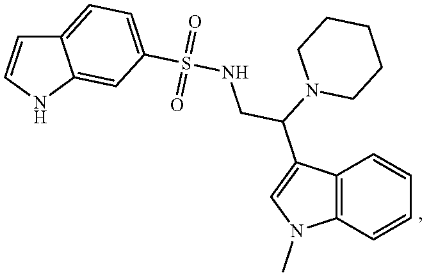
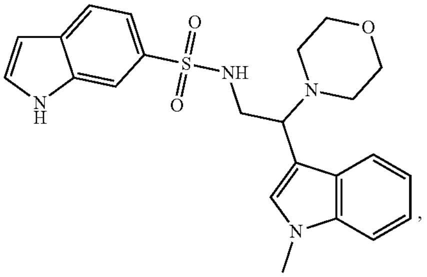
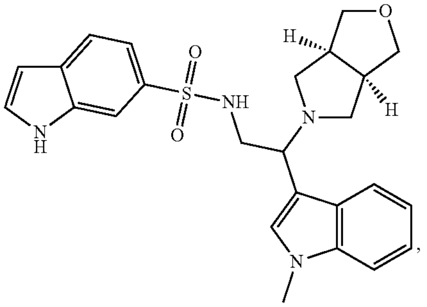

-continued
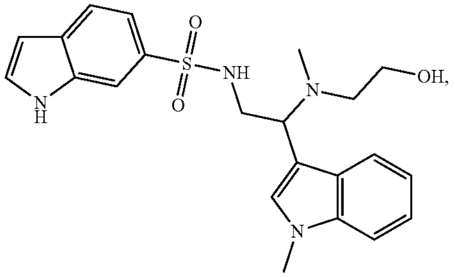
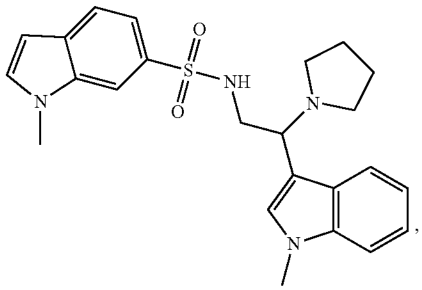
,
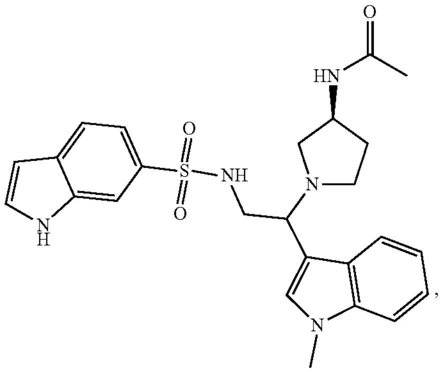
,
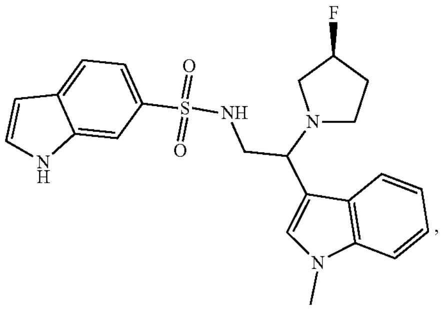
,
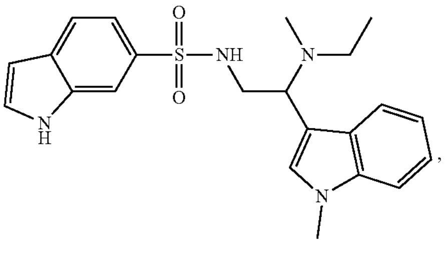
,
-continued
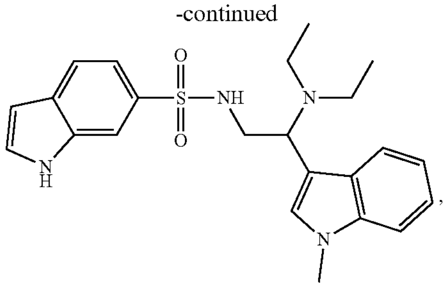
,
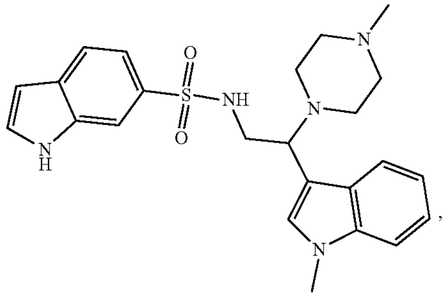
,
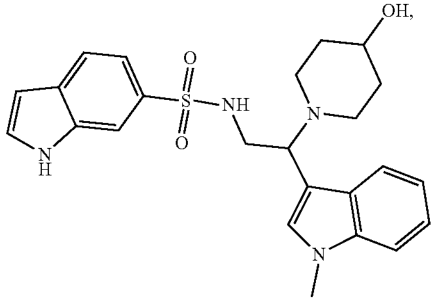
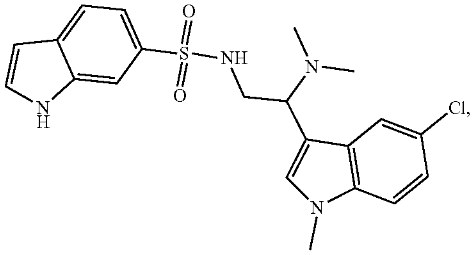
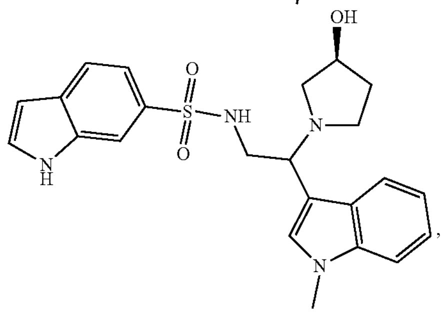
,
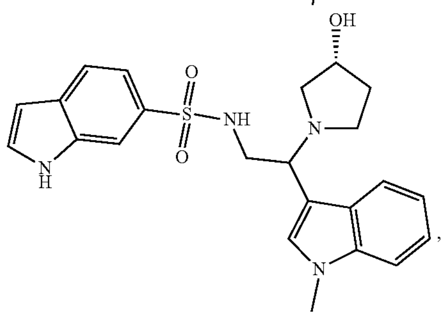
, -continued
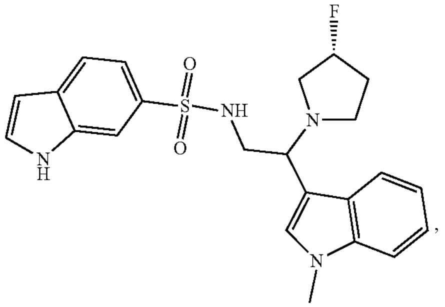,
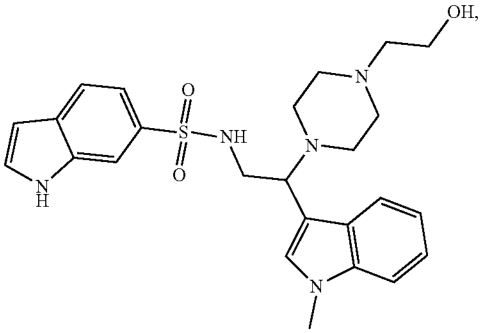,
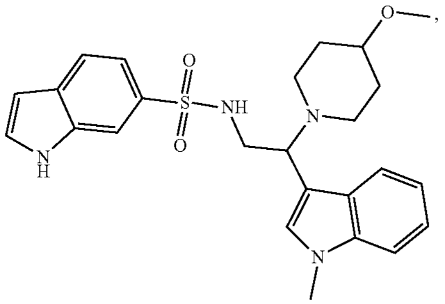,
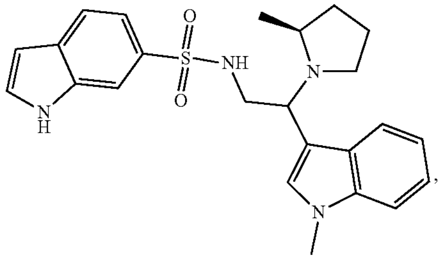,
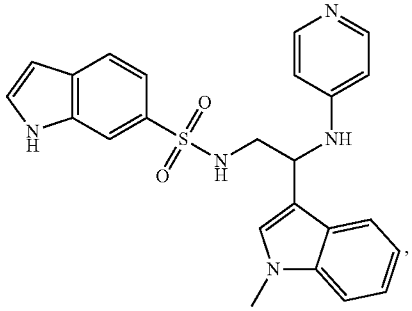,
-continued
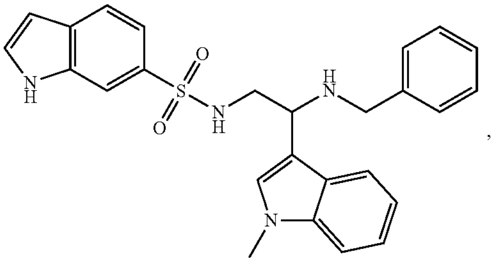,
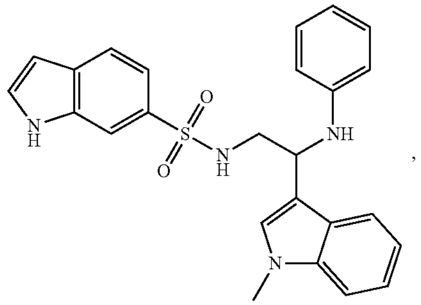,
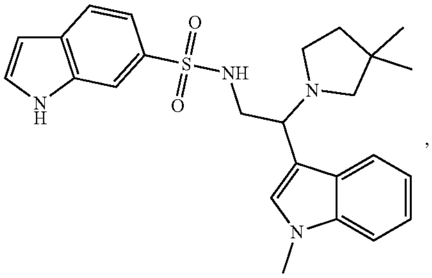,
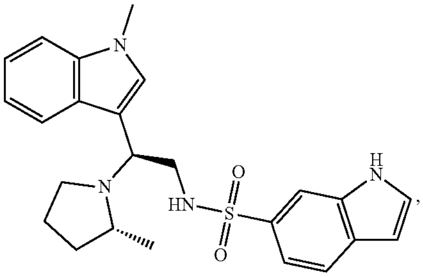,
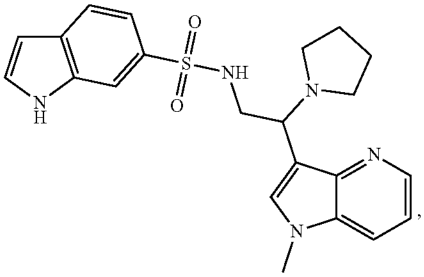,
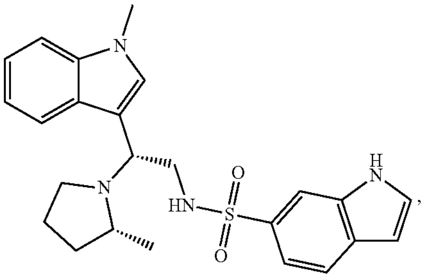, -continued
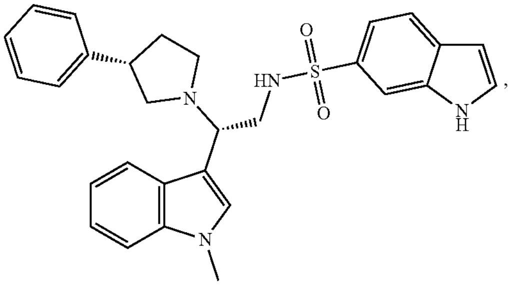,
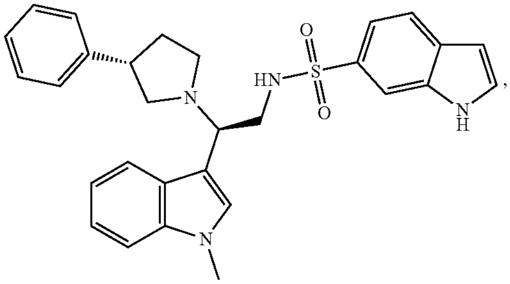,
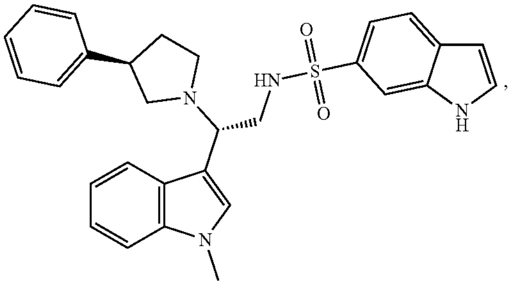,
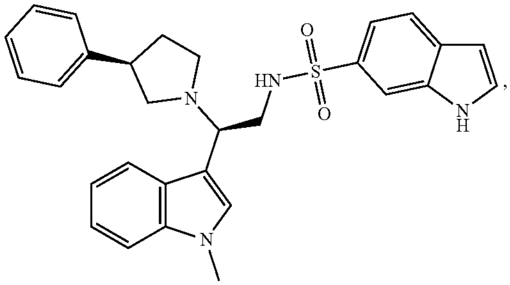,
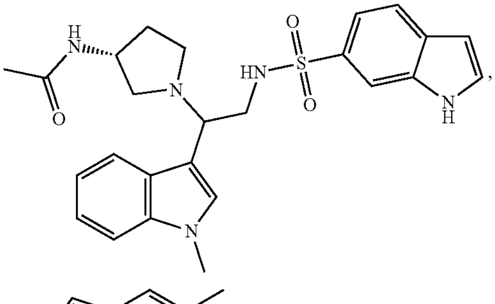,
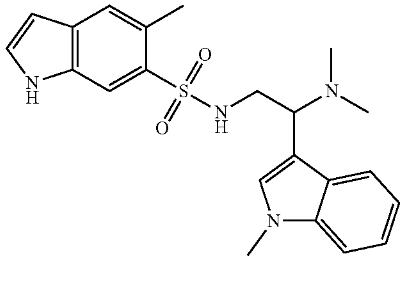,
-continued
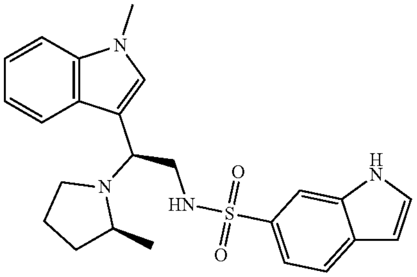,
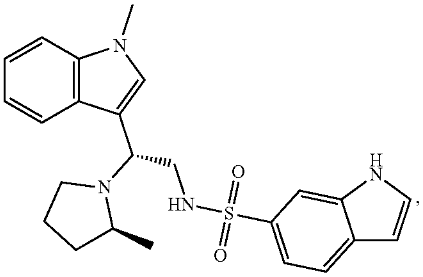,
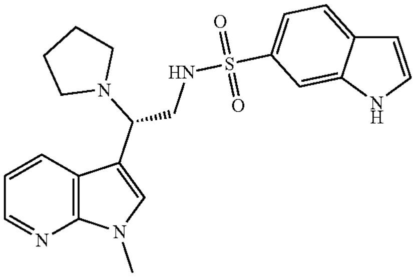,
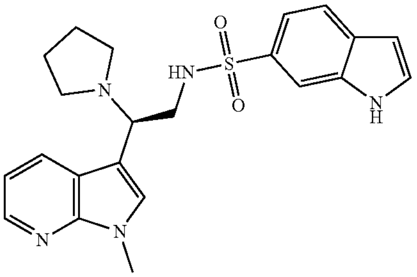,
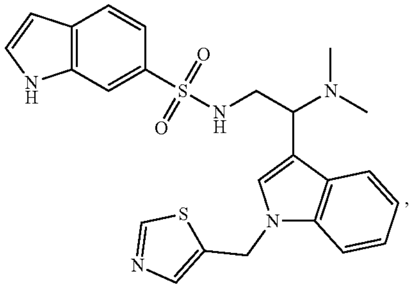,
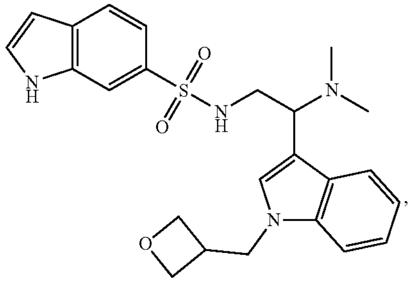, -continued
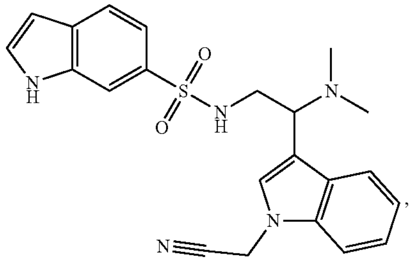
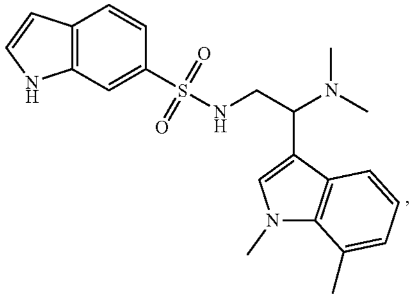
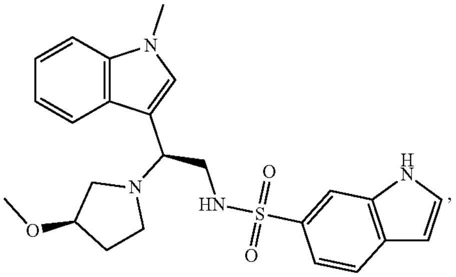
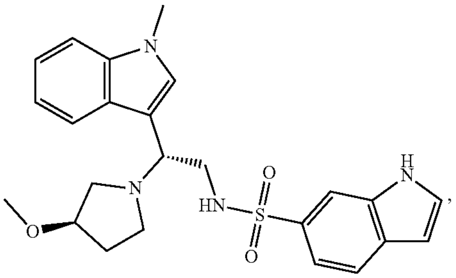
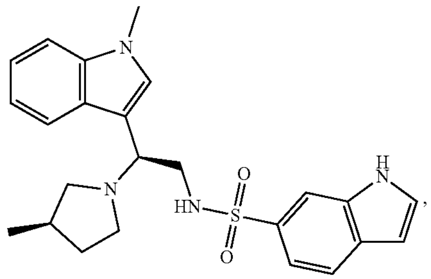
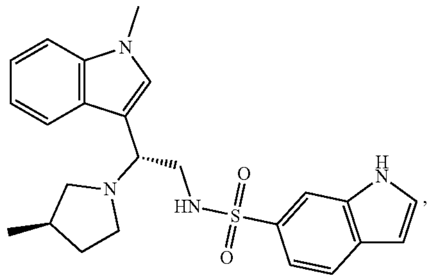
-continued
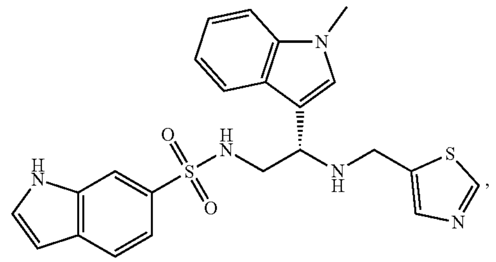
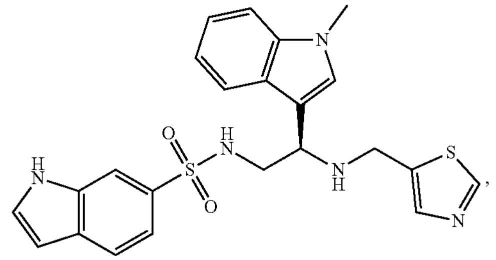
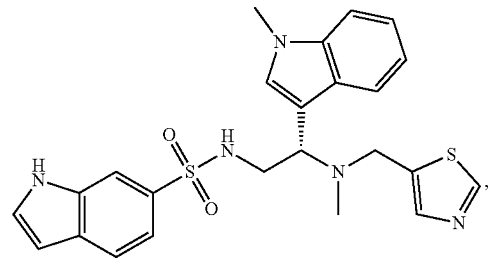
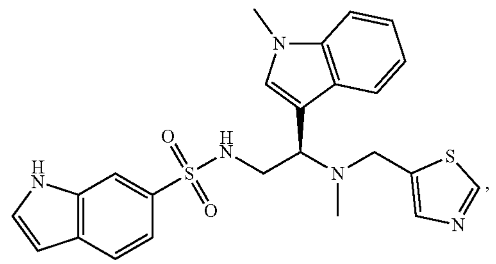
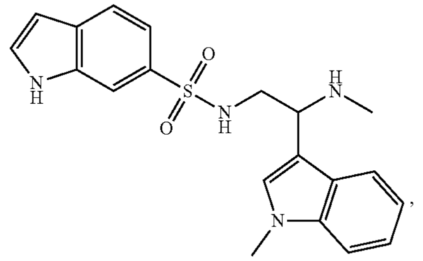
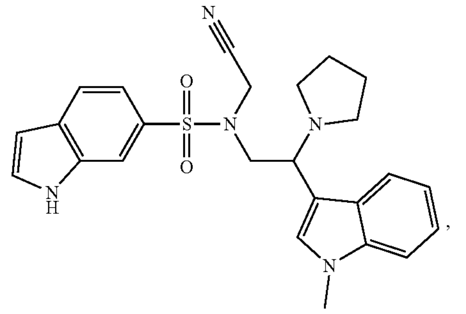

-continued
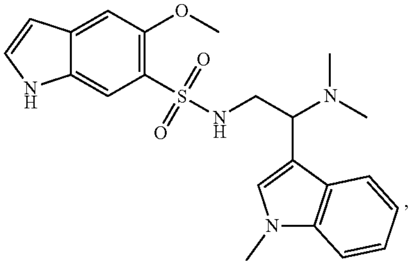
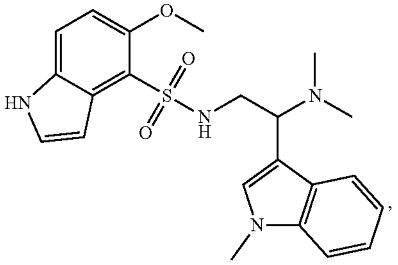
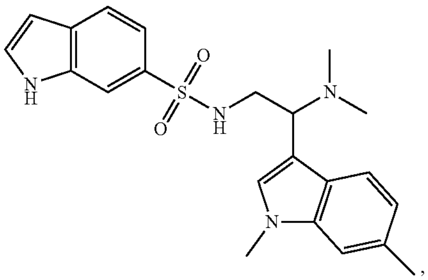
-continued
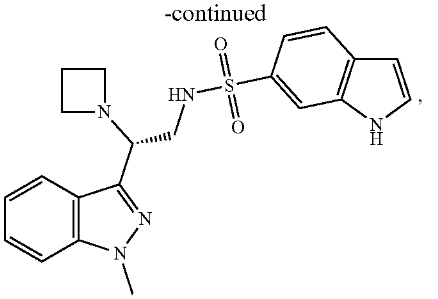
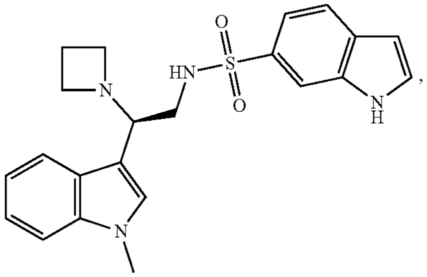
and
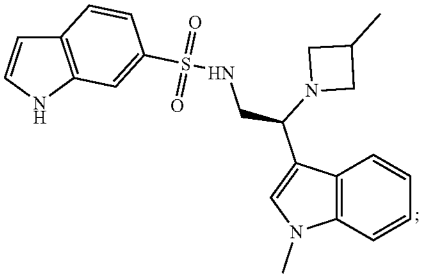
or a pharmaceutically acceptable salt thereof.
* * * * *